United States Patent
Zimmerman et al.

(10) Patent No.: US 10,559,827 B2
(45) Date of Patent: Feb. 11, 2020

(54) ELECTROCHEMICAL CELL HAVING SOLID IONICALLY CONDUCTING POLYMER MATERIAL

(71) Applicant: IONIC MATERIALS, INC., Woburn, MA (US)

(72) Inventors: Michael A. Zimmerman, No. Andover, MA (US); Alexei B. Gavrilov, Woburn, MA (US); Ting Liu, Wilmington, MA (US)

(73) Assignee: Ionic Materials, Inc., Woburn, MA (US)

( * ) Notice: Subject to any disclaimer, the term of this patent is extended or adjusted under 35 U.S.C. 154(b) by 78 days.

(21) Appl. No.: 15/605,425

(22) Filed: May 25, 2017

(65) Prior Publication Data

US 2018/0006308 A1 Jan. 4, 2018

Related U.S. Application Data

(63) Continuation-in-part of application No. 14/559,430, filed on Dec. 3, 2014, now Pat. No. 9,742,008.
(Continued)

(51) Int. Cl.
*H01M 4/62* (2006.01)
*H01M 4/131* (2010.01)
(Continued)

(52) U.S. Cl.
CPC ........ *H01M 4/622* (2013.01); *C08G 75/0209* (2013.01); *H01M 4/131* (2013.01);
(Continued)

(58) Field of Classification Search
CPC ........... H01M 10/054; H01M 10/0565; H01M 10/26; H01M 2004/027; H01M 2004/028; H01M 2300/0082; H01M 4/0411; H01M 4/06; H01M 4/131; H01M 4/24; H01M 4/364; H01M 4/38; H01M 4/42; H01M 4/48; H01M 4/50; H01M 4/502;
(Continued)

(56) References Cited

U.S. PATENT DOCUMENTS

| 2,638,489 A | 5/1953 | Ruben |
| 3,336,279 A | 8/1967 | Scott |

(Continued)

FOREIGN PATENT DOCUMENTS

| CN | 1285086 A | 2/2001 |
| CN | 1326596 A | 12/2001 |

(Continued)

OTHER PUBLICATIONS

Candlin, J. "Polymers" within "The Chemical Industry: Second Edition." Edited by Alan Heaton. 1994. Spring Science+Business Media Dordrecht, pp. 116-121.
(Continued)

*Primary Examiner* — Carlos Barcena
(74) *Attorney, Agent, or Firm* — Preti Flaherty Beliveau & Pachios LLP

(57) ABSTRACT

The invention features an electrochemical cell having an anode and a cathode; wherein at least one of the anode and cathode includes a solid ionically conducting polymer material that can ionically conduct hydroxyl ions.

6 Claims, 23 Drawing Sheets

Related U.S. Application Data

(60) Provisional application No. 61/911,049, filed on Dec. 3, 2013, provisional application No. 62/342,432, filed on May 27, 2016.

(51) Int. Cl.
| | |
|---|---|
| *H01M 4/02* | (2006.01) |
| *C08G 75/0209* | (2016.01) |
| *C01F 5/00* | (2006.01) |
| *G01N 25/48* | (2006.01) |

(52) U.S. Cl.
CPC .............. *C01F 5/00* (2013.01); *G01N 25/4866* (2013.01); *H01M 2004/027* (2013.01); *H01M 2004/028* (2013.01)

(58) Field of Classification Search
CPC .......... H01M 4/58; H01M 4/62; H01M 4/622; H01M 4/624; H01M 6/181
See application file for complete search history.

(56) References Cited

U.S. PATENT DOCUMENTS

| | | | |
|---|---|---|---|
| 3,502,606 | A | 3/1970 | Conciatori et al. |
| 4,243,732 | A | 1/1981 | Powers et al. |
| 4,465,744 | A | 8/1984 | Susman et al. |
| 4,720,910 | A | 1/1988 | Rourke et al. |
| 4,804,594 | A | 2/1989 | Jow et al. |
| 4,925,751 | A | 5/1990 | Shackle et al. |
| 5,147,739 | A | 9/1992 | Beard |
| 5,270,137 | A | 12/1993 | Kubota |
| 5,403,675 | A | 4/1995 | Ogata et al. |
| 5,462,566 | A | 10/1995 | Skotheim |
| 5,506,073 | A | 4/1996 | Angell et al. |
| 5,582,937 | A | 12/1996 | LaFollette |
| 5,599,355 | A | 2/1997 | Nagasubramanian et al. |
| 5,620,811 | A | 4/1997 | Zhang et al. |
| 5,648,187 | A | 7/1997 | Skotheim |
| 5,688,613 | A | 11/1997 | Li et al. |
| 5,888,672 | A | 3/1999 | Gustafson et al. |
| 6,110,619 | A | 8/2000 | Zhang et al. |
| 6,183,914 | B1 | 2/2001 | Yao et al. |
| 6,248,474 | B1 | 6/2001 | Nishiyama et al. |
| 6,274,681 | B1 | 8/2001 | Inagaki et al. |
| 6,376,123 | B1 | 4/2002 | Chu |
| 6,451,487 | B1 | 9/2002 | Besner et al. |
| 6,645,675 | B1 | 11/2003 | Munshi |
| 6,652,440 | B1 | 11/2003 | Kovalev et al. |
| 7,651,647 | B1 | 1/2010 | Strange et al. |
| 8,945,432 | B2 | 2/2015 | Towns |
| 9,819,053 | B1 | 11/2017 | Zimmerman |
| 2001/0003863 | A1 | 6/2001 | Thibault et al. |
| 2002/0010261 | A1* | 1/2002 | Callahan ............ B01D 67/0006 524/832 |
| 2002/0177043 | A1 | 11/2002 | Ndzebet et al. |
| 2003/0069343 | A1 | 4/2003 | Smith et al. |
| 2003/0162087 | A1 | 8/2003 | Clarke et al. |
| 2003/0209692 | A1 | 11/2003 | Farrand et al. |
| 2004/0229118 | A1 | 11/2004 | Wensley et al. |
| 2005/0019661 | A1 | 1/2005 | Han et al. |
| 2005/0112471 | A1 | 5/2005 | Chen |
| 2005/0181280 | A1 | 8/2005 | Ceder et al. |
| 2005/0244696 | A1 | 11/2005 | Kuromatsu |
| 2006/0166085 | A1 | 7/2006 | Hennige et al. |
| 2006/0269834 | A1 | 11/2006 | West et al. |
| 2007/0020525 | A1 | 1/2007 | Kim et al. |
| 2007/0051366 | A1 | 3/2007 | Hansmann et al. |
| 2007/0166618 | A1 | 7/2007 | Armand et al. |
| 2007/0250036 | A1 | 10/2007 | Volk et al. |
| 2008/0066297 | A1 | 3/2008 | Lin et al. |
| 2008/0090138 | A1 | 4/2008 | Vu et al. |
| 2008/0248356 | A1 | 10/2008 | Kimura et al. |
| 2008/0292953 | A1 | 11/2008 | Hosaka et al. |
| 2008/0300380 | A1 | 12/2008 | Bai et al. |
| 2009/0272731 | A1 | 11/2009 | Olding et al. |
| 2010/0227224 | A1 | 9/2010 | Eitouni et al. |
| 2011/0070487 | A1 | 3/2011 | Padhi et al. |
| 2011/0104511 | A1 | 5/2011 | Okumura et al. |
| 2011/0104571 | A1 | 5/2011 | Zhamu et al. |
| 2011/0274983 | A1 | 11/2011 | Yontz et al. |
| 2011/0274990 | A1 | 11/2011 | Xu |
| 2011/0281158 | A1 | 11/2011 | Tazoe |
| 2011/0281159 | A1 | 11/2011 | Farmer |
| 2011/0318646 | A1 | 12/2011 | Babinec |
| 2012/0107690 | A1 | 5/2012 | Wakizaka et al. |
| 2012/0129045 | A1 | 5/2012 | Gin et al. |
| 2012/0164526 | A1 | 6/2012 | Adamson et al. |
| 2012/0231355 | A1 | 9/2012 | Lee et al. |
| 2012/0321970 | A1 | 12/2012 | Friesen et al. |
| 2013/0136981 | A1 | 5/2013 | Peuchert et al. |
| 2014/0057153 | A1 | 2/2014 | Visco et al. |
| 2014/0059820 | A1 | 3/2014 | Wright et al. |
| 2014/0088207 | A1 | 3/2014 | Elabd et al. |
| 2014/0377621 | A1 | 12/2014 | Hanyu et al. |
| 2015/0064574 | A1 | 3/2015 | He et al. |
| 2015/0155559 | A1 | 6/2015 | Zimmerman et al. |
| 2015/0280218 | A1 | 10/2015 | Zimmerman et al. |
| 2016/0233461 | A1 | 8/2016 | Young et al. |
| 2017/0018781 | A1 | 1/2017 | Zimmerman |
| 2017/0338492 | A1 | 11/2017 | Zimmerman |
| 2018/0006308 | A1 | 1/2018 | Zimmerman et al. |

FOREIGN PATENT DOCUMENTS

| | | |
|---|---|---|
| CN | 1326596 C | 12/2001 |
| CN | 1354529 C | 6/2002 |
| CN | 1372705 A | 10/2002 |
| CN | 1457518 C | 11/2003 |
| JP | 59-157151 | 9/1984 |
| JP | 59-157151 A | 9/1984 |
| JP | 9-219197 | 8/1997 |
| JP | 9-219197 A | 8/1997 |
| JP | 2002-358959 | 12/2002 |
| JP | 2002/358959 A | 12/2002 |
| JP | 2012-517519 | 8/2012 |
| JP | 2012/517519 B2 | 8/2012 |
| WO | 1998/42037 A1 | 9/1998 |
| WO | 1999/33127 A1 | 7/1999 |
| WO | 2001/17051 A1 | 3/2001 |
| WO | 2004/027909 | 4/2004 |
| WO | 2004/027909 A1 | 4/2004 |
| WO | 2011/146670 A1 | 11/2011 |
| WO | 2015/084940 A1 | 6/2015 |
| WO | 2015/153729 A1 | 10/2015 |

OTHER PUBLICATIONS

Dang, T.D. et al., "Ionic Conductivity of Conjugated Water-Soluble Rigid-Rod Polymers," Journal of Polymer Science: Part B: Polymer Physics, vol. 31 pp. 1941-1950, 1993.

Definition of Dopant. http://www.merriam-webster.com/dictionary/dopant. Downloaded Feb. 4, 2019.

Definition of Nonflammable. http://www.dictionary.com/browse/nonflammable?s=t. As viewed on Jun. 7, 2016.

Edman, L. et al., "Transport properties of the Solid Polymer Electrolyte System P(EO)nLiTFSI," Journal of Physical Chemistry B, 2000; vol. 104, No. 15, pp. 3476-3480.

Ferrando, W.A., "Development of a Novel Composite Aluminum Anode," Journal of Power Sources, vol. 130, Issues 102, pp. 309-314, May 2004. Abstract only.

Florjanczyk, Z. et al., "Polymer-in-Salt Electrolytes Based on Acrylonitrile/Butyl Acrylate Copolymers and Lithium Salts," Journal of Physical Chemistry B, 2004, vol. 108, pp. 14907-14914.

Kösters, J. et al., "Ion Transport Effects in a Solid Polymer Electrolyte Due to Salt Substitution and Addition Using an Ionic Liquid," Journal of Physical Chemistry B, 2013, vol. 117, pp. 2527-2534.

Lefrou, C. et al., "Electrochemistry: The Basics, With Examples." Springer-Verlag Berlin Heidelberg, pp. 22-25, 2012.

(56) References Cited

OTHER PUBLICATIONS

Lesch, V. et al., "A Combined theoretical and experimental study of the Influence of Different anion ratios on lithium ion dynamics in ionic liquids," Journal of Physical Chemistry B, 2014, vol. 118, No. 26, pp. 7367-7375.

Liew, C.-W. et al., "Characterization of ionic liquid added poly(vinyl alcohol)-based proton conducting polymer electrolytes and electrochemical studies on the supercapacitors," International Journal of Hydrogen Energy, vol. 40, pp. 852-862, 2015.

Miyatake, K. et al., "Synthesis of poly(phenylene sulfide sulfonic acid) via poly(sulfoniumcation) as a thermostable proton-conducting polymer," Macromolecules, vol. 29, pp. 6969-6971, 1996.

OPI Online Courses, "Insulator, Semiconductor Conductor," (online), Jul. 1, 2012.

Polyphenylene Sulfide Information. DIC Corporation. http://www.dic-global.com/us/en/products/pps/about.html. Downloaded on Jun. 8, 2016.

Polystyrene, Wikipedia. https://en.wikipedia.org/wiki/Polystyrene. Downloaded Feb. 4, 2019.

Sandor, R.B., "PBI (Polybenzimidazole): Synthesis, Properties and Applications," High Performance Polymers, vol. 2, No. 1, pp. 25-37, 1990.

Sannigrahi, A. et al., "Tuning the Molecular Properties of Polybenzimidazole by Copolymerization," Journal of Physical Chemistry B, vol. 111, pp. 12124-12132, 2007.

Santhosh, P. et al., "Preparation and properties of new cross-linked polyurethane acrylate electrolytes for lithium batteries," Journal of Power Sources 160, pp. 609-620, 2006.

Teng, H., "Overview of the development of the fluoropolymer Industry," Applied Sciences, 2012, vol. 2, pp. 496-512.

Wikipedia entry of Electrolyte. https://en.wikipedia.org/wiki/Electrolyte. Downloaded Feb. 1, 2019.

Yang, Y. et al., "Effect of Lithium Iodide Addition on Poly(ethylene oxide)-Poly(vinylidene fluoride) Polymer-Blend Electrolyte for dye-Sensitized Nanocrystalline Solar Cell," Journal of Physical Chemistry B, vol. 112, pp. 6594-6602, 2008.

Translated Text of the First Office Action, dated Aug. 7, 2018, from related Chinese Patent Application No. 2015/80018411.6.

Supplementary European Search Report, dated Apr. 5, 2017, from related European Patent Application No. 14868257, filed on Dec. 3, 2014.

Extended European Search Report, dated Oct. 8, 2018, from related European Patent Application No. 16804487.3, filed on Jan. 4, 2018.

Extended European Search Report, dated Oct. 5, 2018, from related European Patent Application No. 16804636.5, filed on Jan. 4, 2018.

Extended European Search Report, dated Dec. 13, 2018, from related European Patent Application No. 16808115.6, filed on Jun. 7, 2016.

International Search Report and the Written Opinion of the International Searching Authority, dated Apr. 5, 2018 from related PCT/US2018/015146 filed on Jan. 25, 2018.

Written Opinion of the Singapore Intellectual Property Office, dated Jul. 31, 2018, from related Singapore Patent Application No. SG2018/4525517527Y.

K. Miyatake, H. Iyotani, K. Yamamoto , E. Tsuchida. Synthesis of poly (phenylene sulfide sulfonic acid) via poly(sulfonium cation) as a thermostable proton-conducting polymer, Macromolecule 1996, 29, 6969-6971.

\* cited by examiner

Dynamic Scanning Calorimetry Curve of Semicrystalline Polymer

| Compounds | A | B | C | D |
|---|---|---|---|---|
| Base Resin | | | | |
| Phillips-Chevron Ryton QC160N PPS | 80 wt% | 50 wt% | 67 wt% | 50 wt% |
| | | | | |
| Ion Source Fillers | | | | |
| Zinc Oxide, 20nm spheres | 20 wt% | 50 wt% | | |
| Lithium Oxide, milled to <2 micron | | | 33 wt% | 50 wt% |

FIG. 3

Table 1
Exemplary formulations investigated.

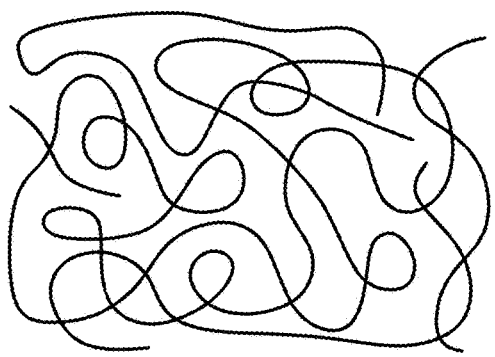

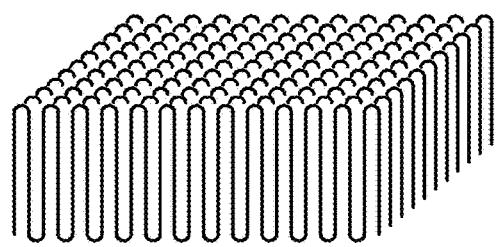

They can fold, and they can stack. A stack of polymer chains folded back on themselves like this is called a lamella.

Amorphous and Crystalline Polymers

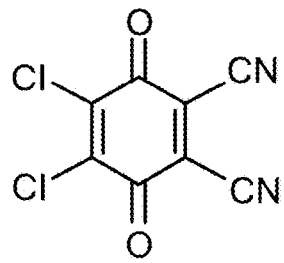

2,3-dicyano-5,6-dichlorodicyanoquinone

Ionic Film Passes UL-VO Flammability Test

Flame Applied to Ionic Film          Flame Self Extinguished in 2 sec.

UL94 Flammability test

Cyclic Voltammetry of Ionically Conductive Polymer versus Lithium Metal

Ionically conductive electrolyte and electrode components

Solid State Battery-Electrode and electrolyte bonded together

Flexible Form of Battery

Extrusion Process

ELECTROCHEMICAL CELL HAVING SOLID IONICALLY CONDUCTING POLYMER MATERIAL

This application is a continuation-in-part of U.S. application Ser. No. 14/559,430, filed Dec. 3, 2014. U.S. Provisional application Ser. No. 62/342,432, filed May 27, 2016 is hereby incorporated by reference for all purposes.

STATEMENT REGARDING FEDERALLY SPONSORED RESEARCH OR DEVELOPMENT (Not applicable)

BACKGROUND OF THE INVENTION

Batteries have become increasingly important in modern society, both in powering a multitude of portable electronic devices, as well as being key components in new green technologies. These new technologies offer the promise of removing the dependence on current energy sources such as coal, petroleum products, and natural gas which contribute to the production of by-product green-house gases. Furthermore, the ability to store energy in both stationary and mobile applications is critical to the success of new energy sources, and is likely to sharply increase the demand for all sizes of advanced batteries. Especially for batteries for large applications, a low base cost of the battery will be key to the introduction and overall success of these applications.

Conventional batteries have limitations, however. For example, lithium ion and other batteries generally employ a liquid electrolyte which is hazardous to humans and to the environment and which can be subject to fire or explosion. Liquid electrolyte batteries are hermetically sealed in a steel or other strong packaging material which adds to the weight and bulk of the packaged battery. Conventional liquid electrolyte suffers from the build-up of a solid interface layer at the electrode/electrolyte interface which causes eventual failure of the battery. Conventional lithium ion batteries also exhibit slow charge times and suffer from a limited number of recharges since the chemical reaction within the battery reaches completion and limits the rechargeability because of corrosion and dendrite formation. The liquid electrolyte also limits the maximum energy density which starts to break down at about 4.2 volts while often 4.8 volts and higher are required in the new industry applications. Conventional lithium ion batteries require a liquid electrolyte separator to allow ion flow but block electron flow, a vent to relieve pressure in the housing, and in addition, safety circuitry to minimize potentially dangerous over-currents and over-temperatures.

With respect to alkaline batteries which rely on the transport of $OH^-$ ions to conduct electricity, the electrolyte becomes saturated with ions (e.g., zincate ions during discharge of $Zn/MnO_2$ batteries) at a certain point and eventually the anode becomes depleted of water. In rechargeable alkaline batteries, the reactions are reversed during charge. Formation of the same ions which saturated the electrolyte may hinder discharging, however. The cathode reaction results in the release of the $OH^-$ ions. The formation of soluble low valent species (e.g., Mn species during discharge of $Zn/MnO_2$ batteries) can adversely affect the utilization of active material however. Although $MnO_2$ can theoretically experience 2-electron reduction with a theoretical capacity of 616 mAh/g, in practice a specific capacity close to theoretical 2-electron discharge has not been demonstrated. Crystalline structure rearrangement with formation of inactive phases and out-diffusion of soluble products limits cathode capacity.

U.S. Pat. No. 7,972,726 describes the use of pentavalent bismuth metal oxides to enhance overall discharge performance of alkaline cells. Cathode containing 10% $AgBiO_3$ and 90% electrolytic $MnO_2$ was shown to deliver 351 mAh/g to 0.8V cut-off at 10 mA/g discharge rate, compared to 287 mAh/g for 100% $MnO_2$ and 200 mAh/g for 100% $AgBiO_3$. The 351 mAh/g specific capacity corresponds to 1.13 electron discharge of $MnO_2$ and represents the highest specific capacity delivered at practically useful discharge rates and voltage range. Bismuth- or lead-modified $MnO_2$ materials, disclosed in U.S. Pat. Nos. 5,156,934 and 5,660,953, were claimed to be capable of delivering about 80% of the theoretical 2-electron discharge capacity for many cycles. It was theorized in literature [Y. F. Yao, N. Gupta, H. S. Wroblowa, J. Electroanal. Chem., 223 (1987), 107; H. S. Wroblowa, N. Gupta, J. Electroanal. Chem., 238 (1987) 93; D. Y. Qu, L. Bai, C. G. Castledine, B. E. Conway, J. Electroanal. Chem., 365 (1994), 247] that bismuth or lead cations can stabilize crystalline structure of $MnO_2$ during discharge and/or allow for 2-electron reduction to proceed via heterogeneous mechanism involving soluble $Mn^{2+}$ species. Containing said $Mn^{2+}$ species seems to be the key for attaining high $MnO_2$ utilization and reversibility. In high carbon content (30-70%) cathodes per U.S. Pat. Nos. 5,156,934 and 5,660,953, the resulting highly porous structure was able to absorb soluble species. However, there is no data to suggest that a complete cell utilizing these cathodes was built or that this worked using a Zn anode.

Accordingly, polymer electrolyte which prevents 1) the dissolution of ions which would otherwise saturate the electrolyte and 2) the dissolution and transport of low-valent species, would improve utilization and rechargeability of alkaline batteries. In addition, it has been suggested [M. Minakshi, P. Singh, J. Solid State Electrochem, 16 (2012), 1487] that Li insertion can stabilize the $MnO_2$ structure upon reduction and enable recharegeablity. A polymer engineered to conduct $Li^+$ and $OH^+$ ions, opens the possibility to tune $MnO_2$ discharge mechanism in favor of either proton or lithium insertion, which can serve as an additional tool to improve life cycle.

Further, while the battery technology for many advanced applications is Lithium Ion (Li-ion), increased demands for higher energy density, both in terms of volumetric (Wh/L) for portable devices, and gravimetric (Wh/kg) for electric vehicles and other large applications have shown the necessity for accessing technologies well beyond the current capabilities of Li-ion cells. One such promising technology is Li/sulfur batteries. A sulfur based cathode is enticing because of the high theoretical energy density (1672 mAh/g) which is ~10× better than the current Li-ion metal oxide cathode active materials. Sulfur is also exciting because it is a very abundant, low cost, environmentally friendly material, unlike many current Li-ion battery materials, such as $LiCoO_2$.

Recently, there has been a great amount of activity in Li/sulfur battery research, with advances in the capacity and cycle life of rechargeable Li/sulfur cells. Activity has included modifications to the cathode, anode, electrolyte and separator, all with the goal of reducing the polysulfide shuttle and thereby improving cell performance. Applications of this research to sulfur cathodes has focused in two main areas: 1) the use of engineered materials to surround and contain the sulfur and soluble lithiated products, for example see: U.S. Patent Application 2013/0065128, and 2)

the use of conductive polymers which react with sulfur to produce a "sulfurized" composite cathode material. Examples of "sulfurized-polymer" include reaction products from high temperature exposure of sulfur with polyacrylonitrile (PAN) [see: Jeddi, K., et. al. *J. Power Sources* 2014, 245, 656-662 and Li, L., et. al. *J. Power Sources* 2014, 252, 107-112]. Other conductive polymer systems used in sulfur cathodes include polyvinylpyrrolidone (PVP) [see: Zheng, G., et. al. *Nano Lett.* 2013, 13, 1265-1270] and polypyrrole (PPY) [see: Ma, G., et. al. *J. Power Sources* 2014, 254, 353-359]. While these methods have met with various degrees of success in limiting the polysulfide shuttle mechanism, they all rely on the use of expensive materials which are not well suited to large scale manufacturing.

BRIEF SUMMARY OF THE INVENTION

A solid, ionically conducting polymer material is provided having very high ionic diffusivity and conductivity at room temperature and over a wide temperature range. The solid ionic polymer material is useful as a solid electrolyte for alkaline batteries and is also is useful as a component to make electrodes for alkaline batteries. The material is not limited to battery applications but is more broadly applicable for other purposes such as alkaline fuel cells, supercapacitors, electrochromic devices, sensors and the like. The polymer material is non-flammable and self-extinguishes, which is especially attractive for applications which otherwise might be flammable. In addition the material is mechanically strong and can be manufactured using high volume polymer processing techniques and equipment which themselves are known in the art.

In one aspect of the invention the solid ionically conducting polymer material serves as an electrolyte to transmit $OH^-$ ions in an alkaline battery. The alkaline battery may comprise various battery chemistries including, but not limited, $Zn/MnO_2$, Zn/Ni, FE/NI, Zn/AIR, Ni/Metal Hydride, Silver Oxide, Metal/Air and others known in the art. The zinc/manganese oxide ($Zn/MnNO_2$) chemistry is the most widely used for consumer alkaline batteries.

A solid ionic polymer electrolyte for lithium ion batteries including the solid, ionically conducting polymer material is disclosed in co-pending U.S. patent application Ser. No. 13/861,170 filed Apr. 11, 2013 and assigned to the same Assignee as the present invention.

In another aspect of the invention, the solid, ionically conducting polymer material is employed to form the cathode, electrolyte and anode of an alkaline battery. The three layers of the battery are solid and can be co-extruded to efficiently form the battery structure. The individual layers may also be or may alternatively be separately extruded or otherwise formed and layered together to form the battery structure.

The solid, ionically conducting polymer material includes a base polymer, a dopant and at least one compound including an ion source. The dopant includes an electron donor, an electron acceptor or an oxidant. In one embodiment for batteries with $OH^-$ chemistry, the base polymer can be a polyphenylene sulfide, a polyether ether ketone also known as PEEK, or a liquid crystal polymer. In this embodiment, the dopant is an electron acceptor such as, for non-limiting examples, 2,3, dicloro-5,6-dicyano-1,4-benzoquinone, TCNE, sulfur trioxide or chloranil. Other dopants acting as electron acceptors or containing functional groups capable to accept electrons can be employed. The compound including an ion source includes compounds containing hydroxyl ions or materials chemically convertible to compounds containing hydroxyl ions including, but not limited to, hydroxides, oxides, salts or mixtures thereof, and more specifically $Li_2O$, $Na_2O$, MgO, CaO, ZnO, LiOH, KOH, NaOH, $CaCl_2$, $AlCl_3$, $MgCl_2$, LiTFSI (lithium bis-trifluoromethanesulfonimide), LiBOB (Lithium bis(oxalate)borate) or a mixture of the preceding two components.

The solid ionically conducting polymer material exhibits carbon 13 NMR (detection at 500 MHz) chemical shift peaks at about 172.5 ppm, 143.6 ppm, 127.7 ppm, and 115.3 ppm. A similar carbon 13 NMR scan of the electron acceptor shows chemical shift peaks at about 195 ppm, and 107.6 ppm in addition to the chemical shift peaks at about 172.5 ppm, 143.6 ppm, 127.7 ppm, and 115.3 ppm. In other words, the reaction between the base polymer and the electron acceptor appears to eliminate the chemical shift peaks at about 195 ppm, and 107.6 ppm. In addition, the $^{13}C$ NMR spectrum of the solid ionically conducting polymer movement in the main peak (dominated by the aromatic carbon) in going from the base polymer to the solid ionically conducting polymer. The chemical shift of the dominant peak in the solid ionically conducting polymer is greater than the chemical shift of the dominant peak in the base polymer.

The material has crystallinity index of at least or greater than about 30%.

The compound including the ion source is in a range of 10 wt. % to 60 wt. %.

The dopant molar ratio is in the range of about 1-16.

The material has an ionic conductivity of at least $1 \times 10^{-4}$ S/cm at room temperature of between 20° C. to 26° C.

The materials have a tensile strength in the range of 5-100 MPa, a Modulus of Elasticity in the range of 0.5-3.0 GPa, and Elongation in the range of 0.5-30%

The material has an OH-diffusivity of greater than $10^{-11}$ $cm^2/S$ at room temperature of between 20° C. to 26° C.

The batteries with $OH^-$ chemistry may be rechargeable or non-rechargeable.

In another aspect, the invention provides a rechargeable alkaline battery including an anode; a cathode; and an electrolyte; wherein at least one of anode, the cathode and the electrolyte include a solid, ionically conducting polymer material.

In one embodiment of said battery, the battery comprises an anode; a cathode; and wherein at least one of the anode, and the cathode comprise a solid, ionically conducting polymer material. The battery can be rechargeable or primary. The battery further comprises an electrolyte, and the electrolyte can comprise the solid, ionically conducting polymer material. The battery can alternatively or additionally further comprise an electrolyte, and said electrolyte can be alkaline. As the solid, ionically conducting polymer can conduct a plurality of $OH^-$ ions and has an $OH^-$ diffusivity of greater than 10-11 $cm^2/sec$ at a temperature in a range of 20° C. to 26° C. it is particularly well suited for use on alkaline battery electrodes.

The solid, ionically conducting polymer material is formed from a reactant product comprising a base polymer, an electron acceptor, and a compound including a source of ions. The solid, ionically conducting polymer material can be used as an electrolyte in either the anode or cathode. If used in a battery the cathode of said battery can comprise an active material selected from the group comprising ferrate, iron oxide, cuprous oxide, iodate, cupric oxide, mercuric oxide, cobaltic oxide, manganese oxide, lead dioxide, silver oxide, oxygen, nickel oxyhydroxide, nickel dioxide, silver peroxide, permanganate, bromate, silver vanadium oxide, carbon monofluoride, iron disulfide, iodine, vanadium oxide, copper sulfide, sulfur or carbon and combinations thereof. The anode of said battery can comprise an active material selected from the group comprising lithium, magnesium, aluminum, zinc, chromium, iron, nickel, tin, lead, hydrogen, copper, silver, palladium, mercury, platinum or gold, and combinations thereof, and alloyed materials thereof.

In an alkaline battery where the cathode comprises manganese dioxide, and the anode comprises zinc. The manganese dioxide can take the form of a β-MnO$_2$ (pyrolusite), a ramsdellite, a γ-MnO$_2$, a ε-MnO$_2$, a λ-MnO$_2$, an electrolytic manganese dioxide (EMD), and a chemical manganese dioxide (CMD) and a combination of the proceeding forms. Further, at least one of the anode and cathode can comprise particles of active material and the solid, ionically conductive polymer material can encapsulate at least one particle of the active material or all of the active material. Such cathodes have shown specific capacity greater than 400 mAh/g, 450 mAh/g, and 500 mAh/g.

The battery can alternatively further comprise an electrically conductive additive and/or a functional additive in either the anode or cathode. The electrically conductive additive can be selected from the group comprising a carbon black, a natural graphite, a synthetic graphite, a graphene, a conductive polymer, a metal particle, and a combination of at least two of the preceding components. The functional additive can be selected from the group comprising bismuth, ZnO, MgO, CaO, SnO$_2$, Na$_2$SnO$_3$, and ZnSO$_4$.

The battery electrodes (anode or cathode) can composite structure which can be formed by a process such as injection molding, tube extrusion and compression molding. In one embodiment of making the solid, ionically conductive polymer material the base polymer is oxidatively doped in the presence of an ion source. The ion source is a compound including at least one hydroxyl group or convertible to a compound containing at least one hydroxyl group, or alternatively selected from the group consisting of a LiOH, a Li$_2$O or a mixture of the preceding two components. The base polymer is selected from the group comprising a liquid crystal polymer, a polyether ether ketone (PEEK), and a polyphenylene sulphide (PPS), or a semicrystalline polymer with a crystallinity index of greater than 30%, and combinations thereof. The electron acceptor which reacts with the base polymer in the presence of the ion source can be selected from the group comprising 2,3, dicloro-5,6-dicyano-1,4-benzoquinone, TCNE, sulfur trioxide or chloranil and combinations thereof. The method can additionally include a heating step to further the reaction. An electrochemically active material can be added to the mixing step and if so added is encapsulated by the reacted ionically conductive polymer. Such a battery with a MnO$_2$ cathode, zinc anode and an alkaline electrolyte wherein the alkaline battery is characterized by a flat discharge curve above 1 V, and having a voltage drop less than 0.3V between 5 and 95% depth of discharge.

The solid, ionically conductive polymer material can also be useful as a separator film, as it is electrically non-conductive, and ionically conductive. Therefore the solid, ionically conductive polymer material cast or otherwise rendered as a film can be used as a separator positioned between an anode and cathode. In addition, the solid, ionically conductive polymer material can be coated onto an electrode to function as a separator or alternatively to isolate the electrode or an electrode component from another battery component such as an aqueous electrolyte. The solid, ionically conductive polymer material enables ionic communication between such an isolated component despite it being physically separated, and electrically segmented from the rest of the battery component. The material can also comprise an aggregated or cast agglomeration of small particles of the solid, ionically conductive polymer material. Such an aggregation can take any shape but include an engineered porosity while possessing an engineered surface area. Fillers, such as hydrophobic materials can be mixed in the material to provide desirable physical properties such as low effective aqueous porosity. Catalysts can be added to the solid, ionically conductive polymer material to enable a combination of catalysis and ionic conductivity, such as required in an air electrode for a metal/air battery. Thus the solid, ionically conductive polymer material can include a low or very high surface area, and or a low or very high porosity. Shapes such as an annulus and other moldable shapes can be engineering with desired physical properties with the ionic conductivity of the solid, ionically conductive polymer material are enabled by the invention.

According to an aspect, an electrochemical comprises a solid ionically conducting polymer material, which is used in either its anode or cathode or both.

In an aspect, the electrochemical cell producing electrical energy via an electrochemical reaction comprising an anode and a cathode; wherein the solid ionically conducting polymer material can ionically conduct hydroxyl ion, whereby the solid ionically conducting polymer material can conduct hydroxyl ion during said electrochemical reaction.

Further aspects of the electrochemical cell can include one or more of the following either individually or in combination:

The cathode can produce hydroxyl ions during the electrochemical reaction.

The solid ionically conducting polymer material has a crystallinity index of at least or greater that about 30%, The solid ionically conducting polymer material comprises at least one hydroxyl ion and has an OH— diffusivity greater that $10^{-11}$ at a temperature in the range of 20° C. to 26° C.

The cathode comprises an active material that generates a hydroxyl ion during electrochemical reaction.

The anode comprises the solid ionically conducting polymer material and further comprises an anode electrochemically active material, wherein the solid ionically conducting polymer material and anode electrochemically active material are mixed, whereby the solid ionically conducting polymer material can ionically conduct hydroxyl ion to the anode electrochemically active material.

The cathode comprises the solid ionically conducting polymer material and further comprises a cathode electrochemically active material, wherein the solid ionically conducting polymer material and cathode electrochemically active material are mixed, whereby the solid ionically conducting polymer material can ionically conduct hydroxyl ion to the cathode electrochemically active material.

Wherein at least a portion of the solid ionically conducting polymer material is in contact with the anode electrochemically active material.

Wherein at least a portion of the solid ionically conducting polymer material is in contact with the cathode electrochemically active material.

The cathode comprises manganese dioxide, and wherein the cell has a specific capacity greater than 308 mAh/g manganese dioxide.

The solid ionically conducting polymer material is positioned interposed between the anode and cathode whereby the solid ionically conducting polymer material conducts hydroxyl ions between the anode and cathode.

The cathode comprises the solid ionically conducting polymer material, and wherein the amount of the solid ionically conducting polymer material ranges between 1 and 40 weight percent of the cathode.

The cell is rechargeable, and wherein the cathode comprises the manganese dioxide, and wherein the amount of manganese dioxide ranges between 20 and 90 weight percent of the cathode.

The cell is primary, and wherein the cathode comprises the manganese dioxide, and wherein the amount of manganese dioxide ranges between 50 and 95 weight percent of the cathode.

The cell further comprises a liquid electrolyte, wherein the liquid electrolyte comprises hydroxyl ions.

The anode and cathode both comprise the solid ionically conducting polymer material, wherein the cell is solid state and does not contain any liquid electrolyte, whereby ionic conductivity of the cell is enabled via the solid ionically conducting polymer material.

The anode comprises zinc, and the cathode comprises manganese dioxide, wherein the cell is primary.

The anode comprises zinc, and the cathode comprises manganese dioxide, wherein the cell is secondary.

The anode comprises aluminum, and the cathode comprises manganese dioxide, wherein the cell is primary.

The anode comprises zinc, and the cathode is fluidly connected or simply exposed to oxygen, whereby the oxygen acts as a cathode electrochemically active material.

BRIEF DESCRIPTION OF THE SEVERAL VIEWS OF THE DRAWINGS

FIG. 3 exemplarily illustrates formulations which were investigated for use with the invention;

FIG. 4 shows a schematic illustration of amorphous and crystalline polymers;

FIG. 5 exemplarily illustrates a chemical diagram of 2,3-dicyano-5,6-dichlorodicyanoquinone (DDQ) as a typical electron acceptor dopant for use in the invention;

DETAILED DESCRIPTION OF THE INVENTION

The invention comprises a solid, ionically conductive polymer material including a base polymer, a dopant, and at least one compound including an ion source. The polymer material has a capacity for ionic conduction over a wide temperature range including room temperature. It is believed that ion "hopping" occurs from a high density of atomic sites. Thus, the polymer material can function as a means for supplying ions and has significant material strength.

For the purposes of this application, the term "polymer" refers to a polymer having a crystalline or semi-crystalline structure. In some applications, the solid, ionically conductive polymer material can be molded into shapes which can be folded back on itself allowing for new physical formats depending on the application. The base polymer is selected depending upon the desired properties of the composition in relation to the desired application.

For purposes of the application, the term "dopant" refers to electron acceptors or oxidants or electron donors. The dopant is selected depending upon the desired properties of the composition in relation to the desired application.

Similarly, the compound including an ion source is selected depending upon the desired properties of the composition in relation to the desired application.

I. $Li^+$ Chemistries

In one aspect, the invention relates to a solid polymer electrolyte including the solid, ionically conductive polymer material in a lithium ion battery.

Figure 1:
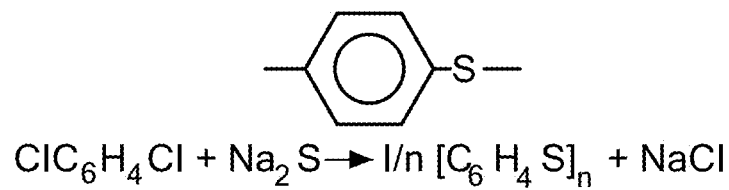
FIG. 1 exemplarily shows a resulting formula for the crystalline polymer of the present invention.
Figure 2:
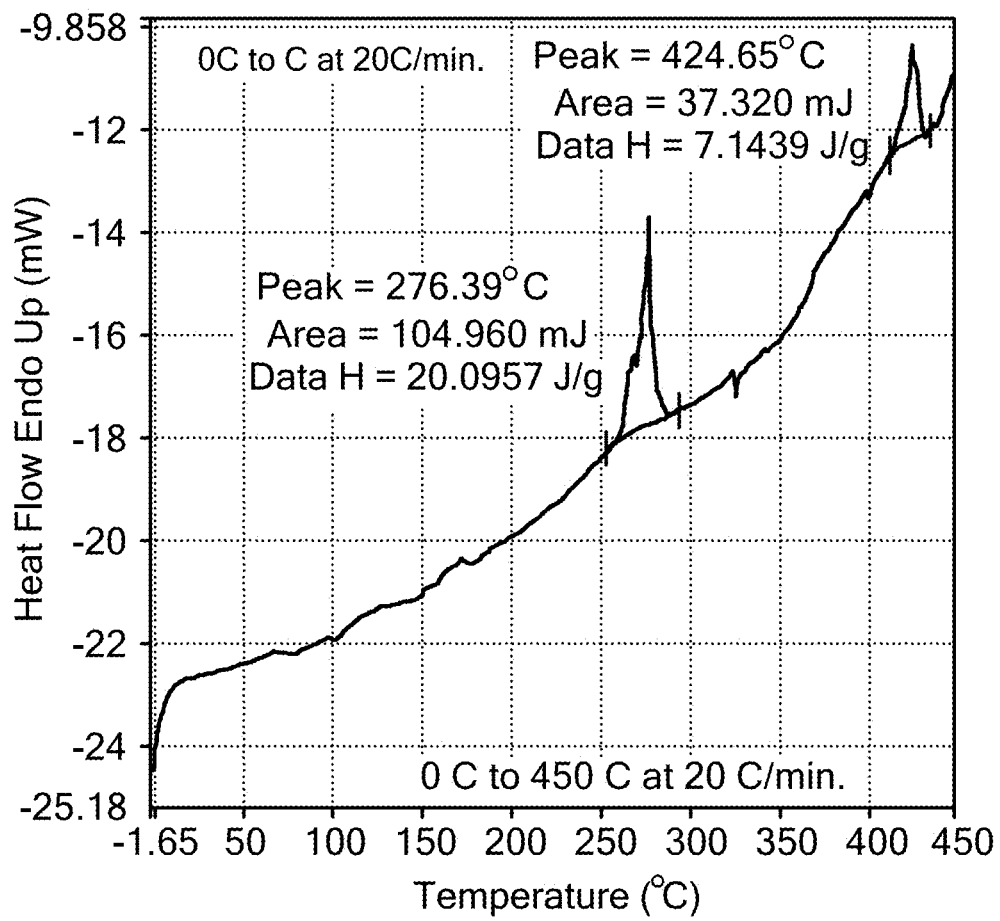
FIG. 2 exemplarily illustrates a dynamic scanning calorimeter curve of a semicrystalline polymer.

In this aspect, the base polymer is characterized as having a crystallinity value of between 30% and 100%, and preferably between 50% and 100%. The base polymer has a glass transition temperature of above 80° C., and preferably above 120° C., and more preferably above 150° C., and most preferably above 200° C. The base polymer has a melting temperature of above 250° C., and preferably above 280° C., and more preferably above 320° C. The molecular weight of the monomeric unit of the base polymer of the invention is in the 100-200 gm/mol range and can be greater than 200 gm/mol. FIG. 1 shows the molecular structure of an exemplary base polymer, wherein the monomeric unit of the base polymer has a molecular weight of 108.16 g/mol. FIG. 2 exemplarily illustrates a dynamic scanning calorimeter curve of an exemplary semicrystalline base polymer. FIG. 3 illustrates exemplary formulations for the solid, ionically conducting polymer material in this aspect of the invention where DDQ is the dopant. Typical materials that can be used for the base polymer include liquid crystal polymers and polyphenylene sulfide also known as PPS, or any semi-crystalline polymer with a crystallinity index greater than 30%, and preferably greater than 50%. In one embodiment, the invention uses a "crystalline or semi-crystalline polymer", exemplarily illustrated in FIG. 4, which typically is above a crystallinity value of 30%, and has a glass transition temperature above 200° C., and a melting temperature above 250° C.

In this aspect, the dopant is an electron acceptor, such as, for non-limiting examples, 2,3-dicyano-5,6-dichlorodicyanoquinone ($C_8Cl_2N_2O_2$) also known as DDQ, Tetracyanoethylene($C_6N_4$) known as TCNE, and sulfur trioxide ($SO_3$). A preferred dopant is DDQ. FIG. 5 provides a chemical diagram of this preferred dopant. It is believed that the purpose of the electron acceptor is two-fold: to release ions for transport mobility, and to create polar high density sites within the polymer to allow for ionic conductivity. The electron acceptor can be "pre-mixed" with the initial ingredients and extruded without post-processing or alternatively, a doping procedure such as vapor doping can be used to add the electron acceptor to the composition after the material is created.

Typical compounds including an ion source for use in this aspect of the invention include, but are not limited to, $Li_2O$, LiOH, ZnO, $TiO_2$, $Al_3O_2$, and the like. The compounds containing appropriate ions which are in stable form can be modified after creation of the solid, polymer electrolytic film.

Other additives, such as carbon particles nanotubes and the like, can be added to the solid, polymer electrolyte including the solid, ionically conducting material to further enhance electrical conductivity or current density.

The novel solid polymer electrolyte enables a lighter weight and much safer architecture by eliminating the need for heavy and bulky metal hermetic packaging and protection circuitry. A novel solid polymer battery including the solid polymer electrolyte can be of smaller size, lighter weight and higher energy density than liquid electrolyte batteries of the same capacity. The novel solid polymer battery also benefits from less complex manufacturing processes, lower cost and reduced safety hazard, as the electrolyte material is non-flammable. The novel solid polymer battery is capable of cell voltages greater than 4.2 volts and is stable against higher and lower voltages. The novel solid polymer electrolyte can be formed into various shapes by extrusion (and co-extrusion), molding and other techniques such that different form factors can be provided for the battery. Particular shapes can be made to fit into differently shaped enclosures in devices or equipment being powered. In addition, the novel solid polymer battery does not require a separator, as with liquid electrolyte batteries, between the electrolyte and electrodes. The weight of the novel solid polymer battery is substantially less than a battery of conventional construction having similar capacity. In some embodiments, the weight of the novel solid polymer battery can be less than half the weight of a conventional battery.

In another aspect of the invention, a solid polymer electrolyte including the solid, ionically conducting polymer material is in the form of an ionic polymer film. An electrode material is directly applied to each surface of the ionic polymer film and a foil charge collector or terminal is applied over each electrode surface. A light weight protective polymer covering can be applied over the terminals to complete the film based structure. The film based structure forms a thin film battery which is flexible and can be rolled or folded into intended shapes to suit installation requirements.

In yet another aspect of the invention, a solid polymer electrolyte including the solid, ionically conducting polymer material is in the form of an ionic polymer hollow monofilament. Electrode materials and charge collectors are directly applied (co-extruded) to each surface of the solid, ionically conductive polymer material and a terminal is applied at each electrode surface. A light weight protective polymer covering can be applied over the terminals to complete the structure. The structure forms a battery which is thin, flexible, and can be coiled into intended shapes to suit installation requirements, including very small applications.

In still another aspect of the invention, a solid polymer electrolyte including the solid, ionically conducting polymer material has a desired molded shape. Anode and cathode electrode materials can be disposed on respective opposite surfaces of the solid polymer electrolyte to form a cell unit. Electrical terminals can be provided on the anode and cathode electrodes of each cell unit for interconnection with other cell units to provide a multi cell battery or for connection to a utilization device.

In aspects of the invention relating to batteries, the electrode materials (cathode and anode) can be combined with a form of the novel solid, ionically conductive polymer material to further facilitate ionic movement between the two electrodes. This is analogous to a conventional liquid electrolyte soaked into each electrode material in a convention lithium-ion battery.

Figure 6:
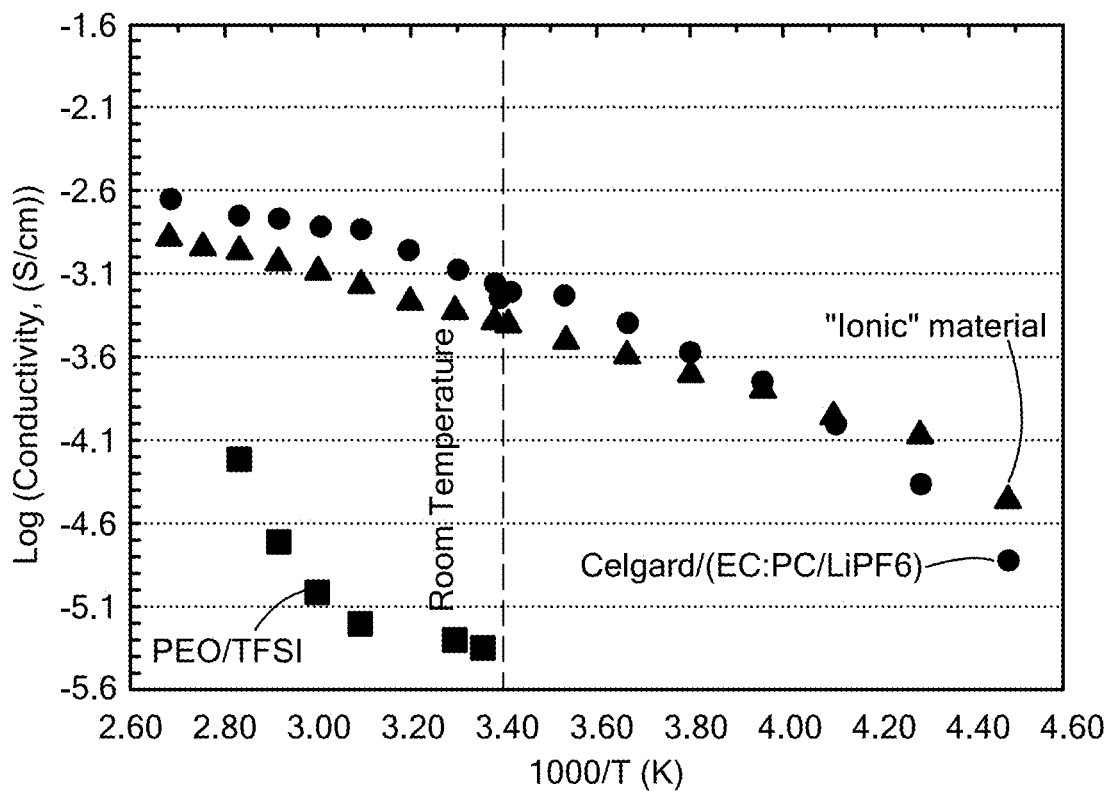
FIG. 6 exemplarily illustrates a plot of the conductivity of the ionically conductive polymer according to the invention in comparison with a liquid electrolyte and a polyethylene oxide lithium salt compound.

Films of solid, ionically conducting polymer materials of the present invention have been extruded in thickness ranging upwards from 0.0003 inches. The ionic surface conductivity of the films has been measured using a standard test of AC-Electrochemical Impedance Spectroscopy (EIS) known to those of ordinary skill in the art. Samples of the solid, ionically conducting polymer material film were sandwiched between stainless steel blocking electrodes and placed in a test fixture. AC-impedance was recorded in the range from 800 KHz to 100 Hz using a Biologic VSP test system to determine the electrolyte conductivity. The results of the surface conductivity measurements are illustrated in FIG. 6. The conductivity of solid, ionically conductive polymer material film according to the invention (Δ) is compared with that of trifluoromethane sulfonate PEO (□) and a liquid electrolyte made up of a Li salt solute and a EC:PC combination solvent using a Celgard separator (O). The conductivity of the solid, ionically conducting polymer material film according to the invention tracks the conductivity of the liquid electrolyte and far surpasses that of trifluoromethane sulfonate PEO at the lower temperatures. Further, unlike PEO electrolytes, the temperature dependence of the conductivity for inventive polymer material does not display a sharp increase above its glass transition temperature, associated with chain mobility, as described by Vogel-Tamman-Fulcher behavior activated by temperature. Therefore, segmental movement as the ion-conduction mechanism in the inventive polymer material is unlikely. Furthermore, this demonstrates that the inventive polymer material has similar ionic conductivity to liquid electrolytes.

Figure 7:
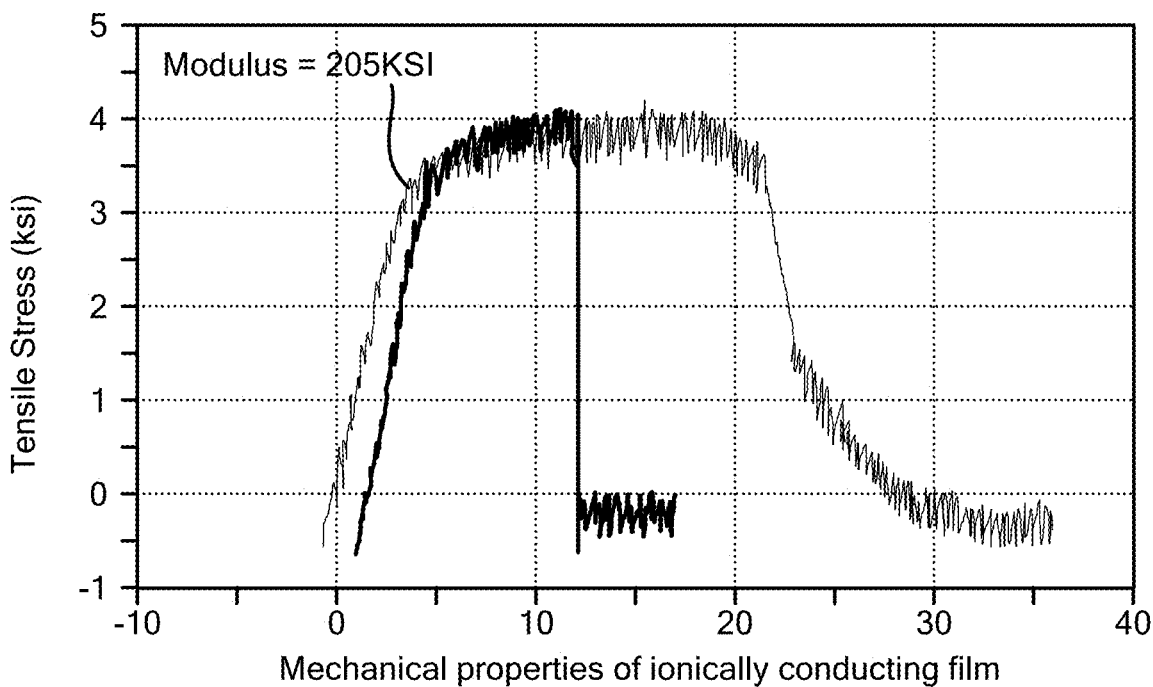
FIG. 7 exemplarily illustrates the mechanical properties of the ionically conducting film according to the invention.

FIG. 7 shows the mechanical properties of the solid, ionically conductive polymer material films of the invention. The mechanical properties were evaluated using the Institute for Interconnecting and Packaging Electronic Circuits IPC-TM-650 Test Methods Manual 2.4.18.3. In the tensile strength versus elongation curve of FIG. 7, the "ductile failure" mode indicates that the material can be very robust.

The solid, ionically conductive polymer material of the invention offers three key advantages in its polymer performance characteristics: (1) It has an expansive temperature range. In lab-scale testing, the crystalline polymer has shown high ionic conductivity both at room temperature and over a wide temperature range. (2) It is non-flammable. The polymer self-extinguishes, passing the UL-V0 Flammability Test. The ability to operate at room temperature and the non-flammable characteristics demonstrate a transformative safety improvement that eliminates expensive thermal management systems. (3) It offers low-cost bulk manufacturing.

Rather than spraying the polymer onto electrodes, the polymer material can be extruded into a thin film via a roll-to-roll process, an industry standard for plastics manufacturing. After the film is extruded, it can be coated with the electrode and charge collector materials to build a battery "from the inside out." This enables thin, flexible form factors without the need for hermetic packaging, resulting in easy integration into vehicle and storage applications at low cost.

It is believed that the solid, ionically conducting polymer material of the present invention creates a new ionic conduction mechanism that provides a higher density of sites for ionic transport and allows the conducting material to maintain higher voltages without risk of thermal runaway or damage to ion transport sites from, for example, lithiation. This characteristic enables the solid, ionically conducting polymer material to be durable for anode materials and higher voltage cathode thin-film applications, resulting in higher energy densities for batteries which may be used in vehicle and stationary storage applications. The ability to maintain high voltages within a solid, ionically conductive polymer material which is mechanically robust, chemical and moisture resistant, and nonflammable not only at room temperature, but over a wide range of temperatures, allows integration with high performance electrodes without costly thermal and safety mechanisms employed by the industry today.

Batteries employing the solid polymer electrolyte including the solid, ionically conductive polymer material of the invention are characterized by an energy density improvement over current commercially available electrolytes, as well as a performance range of $-40°$ C. to $150°$ C. with minimal conductivity degradation. The solid polymer electrolyte can be extruded by a process that produces polymers of a thickness of 6 microns, which enables thin-film formats under commercial manufacturing conditions at batch scale. Further, such extrusion processes enables high throughput, low-cost manufacturing lines for the production of the solid polymer electrolyte, and the processes can be integrated into a variety of product lines, including lithium and zinc battery manufacture. Battery costs can be reduced by up to 50%.

Figure 8:
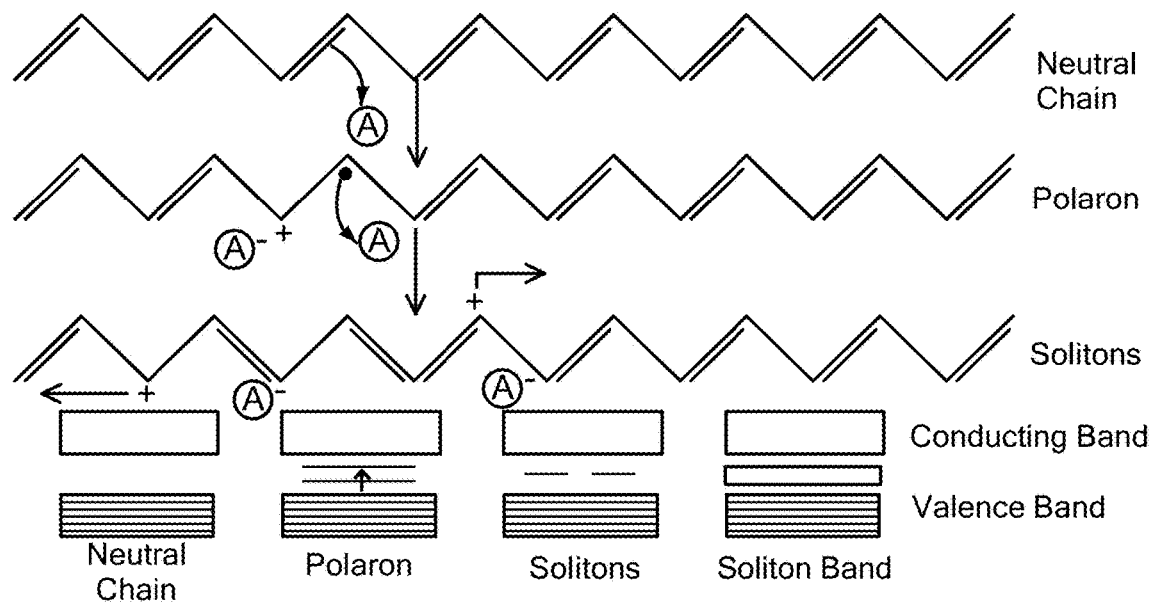
FIG. 8 exemplarily illustrates possible mechanisms of conduction of the solid electrolyte polymer according to the invention.

In addition, the solid, ionically conductive polymer material is not limited to use in batteries, but can be used in any device or composition that includes an electrolyte material. For example, the novel solid, ionically conductive polymer material can be used in electrochromic devices, electrochemical sensors, supercapacitors and fuel cells. FIG. 8 shows possible mechanisms of conduction of the solid, ionically conducting polymer material in a solid polymer electrolyte aspect of the invention. Charge carrier complexes are set up in the polymer as a result of the doping process.

Figure 9:
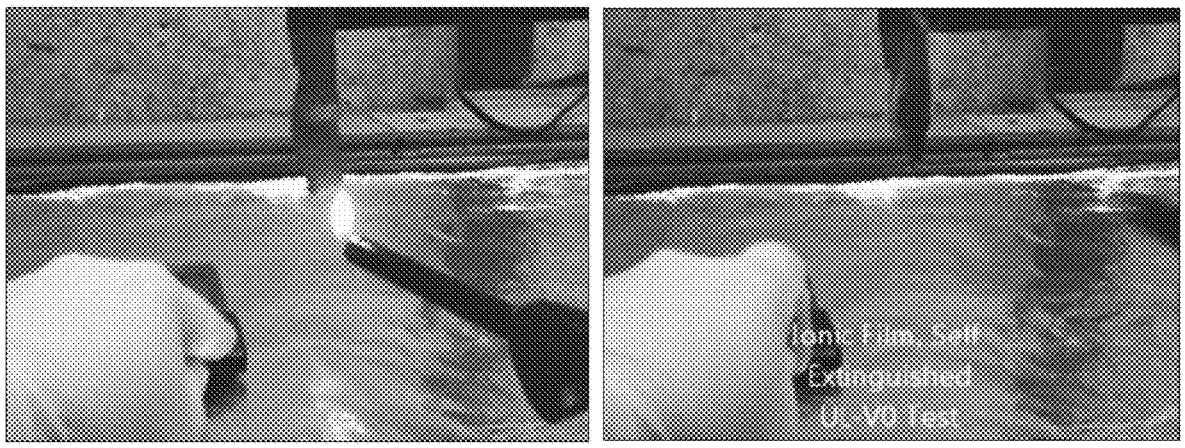
FIG. 9 exemplarily shows a UL94 flammability test conducted on a polymer according to the invention.

Flammability of the solid polymer electrolyte including the solid, ionically conductive polymer material of the invention was tested using a UL94 flame test. For a polymer to be rated UL94-V0, it must "self-extinguish" within 10 seconds and 'not drip". The solid polymer electrolyte was tested for this property and it was determined that it self-extinguished with 2 seconds, did not drip, and therefore easily passed the V0 rating. FIG. 9 shows pictures of the result.

Figure 10:
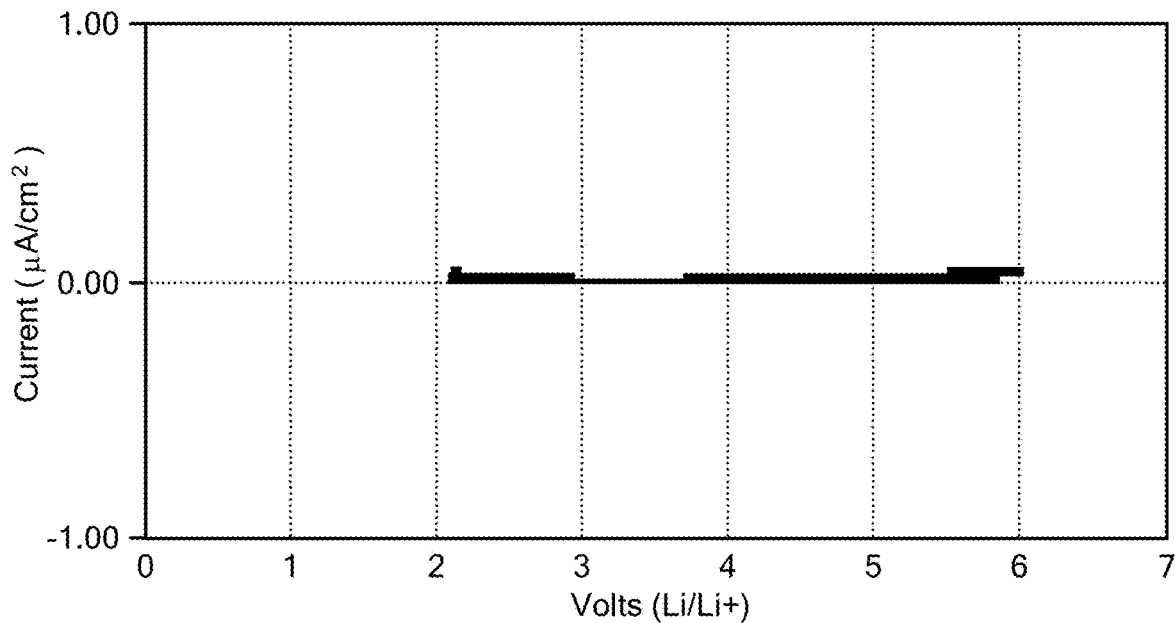
FIG. 10 exemplarily shows a plot of volts versus current of an ionically conductive polymer according to the invention versus lithium metal.

In addition to the properties of ionic conductivity, flame resistance, high temperature behavior, and good mechanical properties, it is preferable that the solid polymer electrolyte including the solid, ionically conductive polymer material of the invention is electrochemically stable at low and high potentials. The traditional test for the electrochemical stability is cyclic voltammetry, when working electrode potential is ramped linearly versus time. In this test, the polymer is sandwiched between a lithium metal anode and blocking stainless steel electrode. A voltage is applied and it is swept positively to a high value (greater than 4 volts vs. Li) for stability towards oxidation and negatively to a low value (0V vs. Li or less) for stability towards reduction. The current output is measured to determine if any significant reaction occurs at the electrode interface. High current output at high positive potential would signify oxidation reaction taking place, suggesting instability with cathode materials operating at these or more positive potentials (such as many metal oxides). High current output at low potentials would signify that a reduction reaction takes place, suggesting instability with anodes operating at these or more negative potentials (such as metal Li or lithiated carbon). FIG. 10 shows a plot of voltage versus current for a solid polymer electrolyte including the solid, ionically conductive polymer material according to the invention versus lithium metal. The study shows that the solid polymer electrolyte is stable up to about 4.4 volts. These results indicate that the solid polymer electrolyte could be stable with cathodes including LCO, LMO, NMC and similar cathodes, along with low voltage cathodes such as, for non-limiting examples iron phosphate and sulfur cathodes.

The solid polymer electrolyte including the solid, ionically conductive polymer material of the invention is able to achieve the following properties: A) high ionic conductivity at room temperature and over a wide temperature range (at least −10° C. to +60° C.); B) non-flammability; C) extrudability into thin films allowing for reel-reel processing and a new way of manufacturing; D) compatibility with Lithium metal and other active materials. Accordingly, this invention allows for the fabrication of a true solid state battery. The invention allows for a new generation of batteries having the following properties:

No safety issues;
New form factors;
Large increases in energy density; and
large improvements in cost of energy storage.

Figure 11:
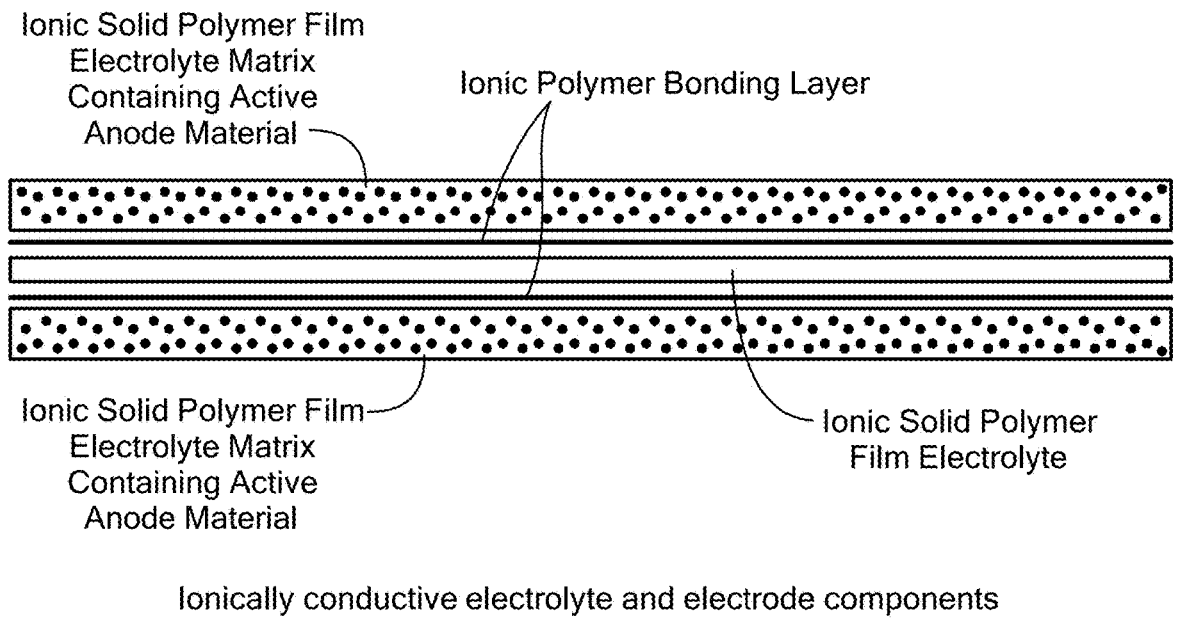
FIG. 11 exemplarily illustrates a schematic of extruded ionically conductive electrolyte and electrode components according to the invention.
Figure 12:
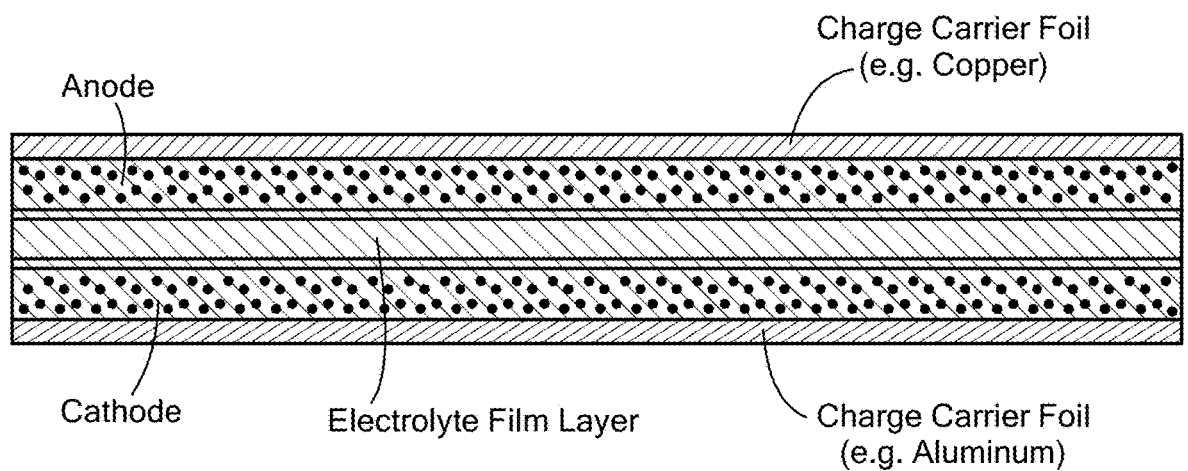
FIG. 12 exemplarily illustrates the solid state battery according to the invention where electrode and electrolyte are bonded together.
Figure 13:
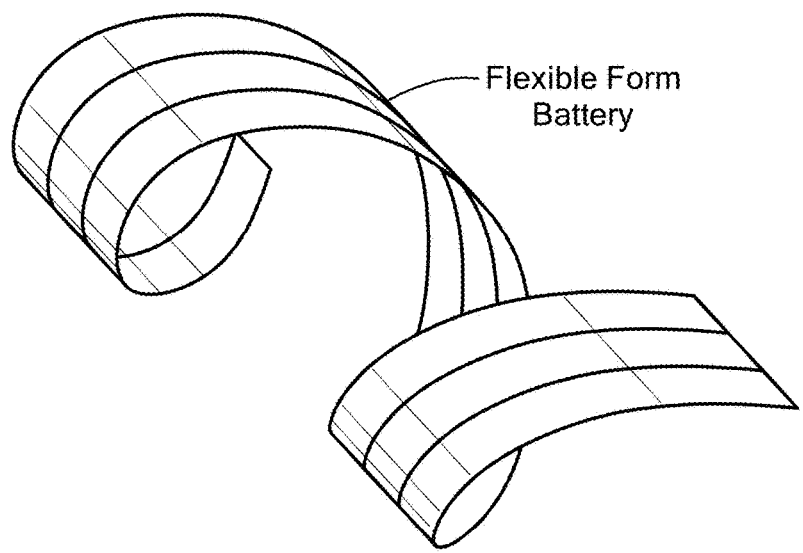
FIG. 13 exemplarily illustrates a final solid state battery according to the invention having a new and flexible form.

FIGS. 11, 12 and 13 show several elements of the solid state battery including the solid, ionically conductive polymer material of the invention which are, respectively: A) an extruded electrolyte; B) extruded anodes and cathodes; and C) a final solid state battery allowing for new form factors and flexibility.

Figure 14:
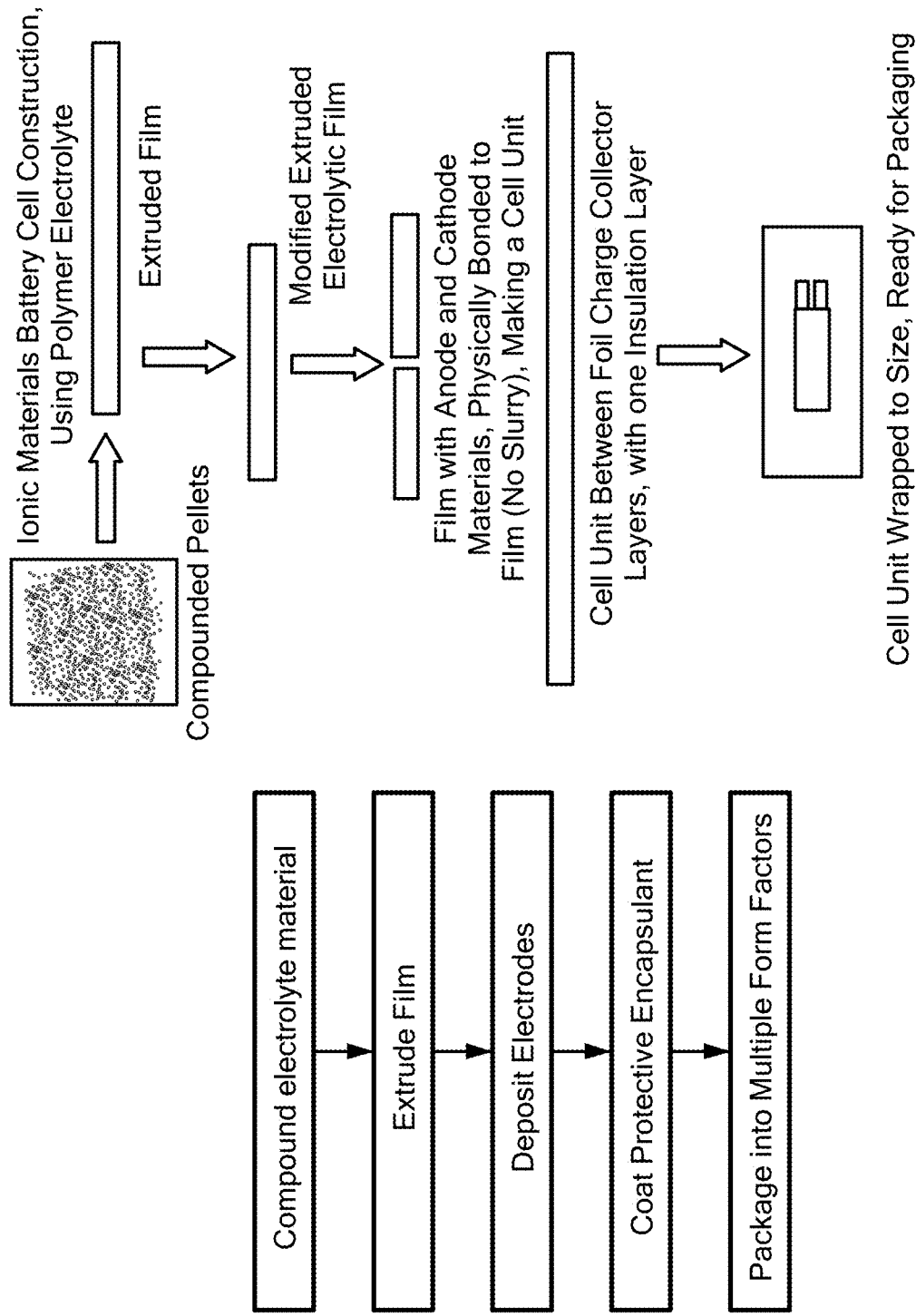
FIG. 14 exemplarily illustrates a method of the invention including steps for manufacturing a solid state battery using an extruded polymer.

In other aspects, the invention provides methods for making Li batteries including the solid, ionically conducting polymer material of the invention. FIG. 14 shows a method of manufacturing a solid state lithium ion battery using an extruded solid, ionically conducting polymer material according to the invention. The material is compounded into pellets, and then extruded through a die to make films of variable thicknesses. The electrodes can be applied to the film using several techniques, such as sputtering or conventional casting in a slurry.

Figure 15:
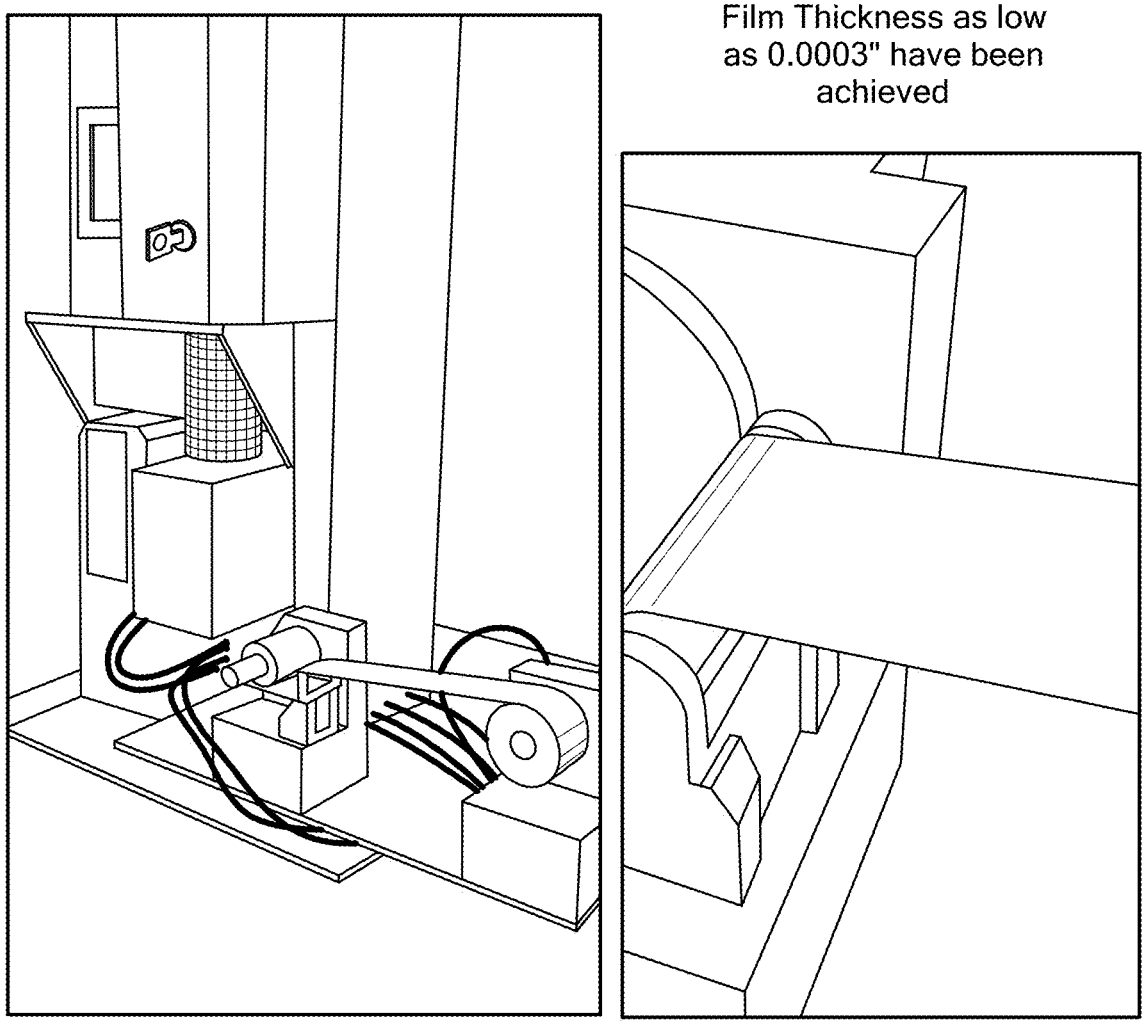
FIG. 15 exemplarily illustrates the extrusion process according to the invention.
Figure 16:
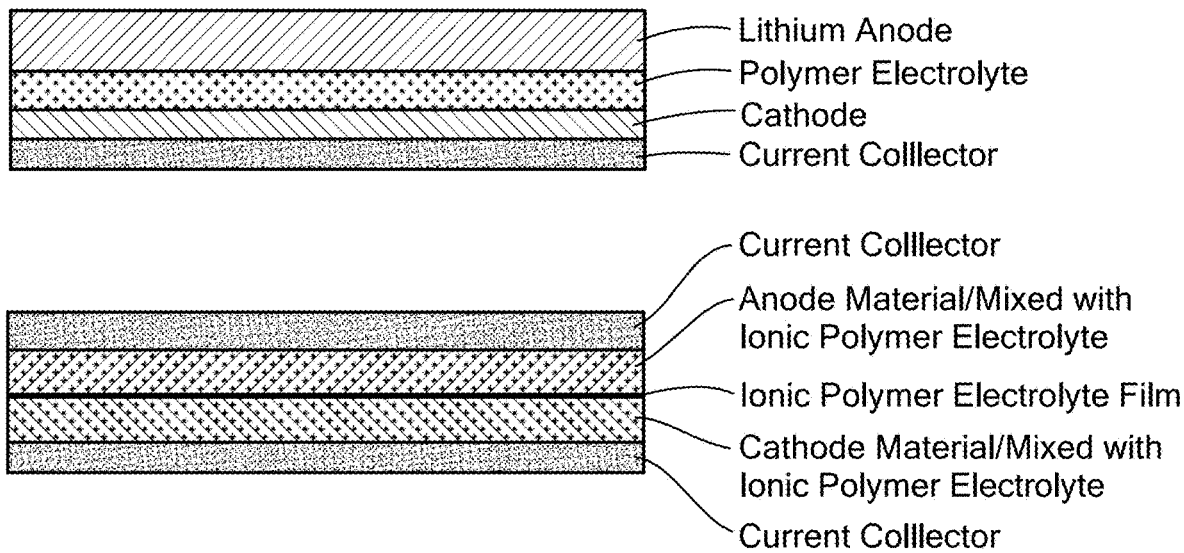
FIG. 16 exemplarily illustrates a schematic representation of an embodiment according to the invention.

In yet another aspect, the invention provides a method of manufacturing of an ionic polymer film including the solid, ionically conductive polymer material of the invention which involves heating the film to a temperature around 295° C., and then casting the film onto a chill roll which solidies the plastic. This extrusion method is shown in FIG. 15. The resulting film can be very thin, in the range of 10 microns thick or less. FIG. 16 shows a schematic representation of the architecture of an embodiment according to the invention.

II. OH⁻ Chemistries

The invention also relates to a solid, ionically conducting polymer material which is engineered to transmit OH⁻ ions, thereby making it applicable for alkaline batteries. For the purposes of present invention, the term "alkaline battery or alkaline batteries" refers to a battery or batteries utilizing alkaline (OFF containing) electrolyte. Such battery chemistries include, but not limited to, $Zn/MnO_2$, Zn/Ni, Fe/Ni, Zn/air, Al/air, Ni/metal hydride, silver oxide and others. $Zn/MnO_2$ chemistry is probably the most widely used and is the main choice for consumer batteries. Although many of the embodiments described herein are related to $Zn/MnO_2$ chemistry, a person of ordinary skill in the art would understand that the same principles are applicable broadly to other alkaline systems.

Alkaline batteries rely on the transport of OH⁻ ions to conduct electricity. In most cases, the OH⁻ ion is also a participant in the electrochemical process. For instance, during the discharge of a $Zn/MnO_2$ battery, the zinc anode releases 2 electrons and consumes OH⁻ ions:

$$Zn+4OH^- \rightarrow Zn(OH)_4^{2-}+2e^- \qquad (1)$$

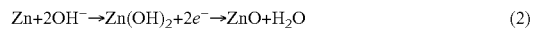

$$Zn+2OH^- \rightarrow Zn(OH)_2+2e^- \rightarrow ZnO+H_2O \qquad (2)$$

$$Zn(OH)_2 \rightarrow ZnO+H_2O \qquad (3)$$

During early stages of discharge of the battery, reaction (1) produces soluble zincate ions, which can be found in the separator and cathode [Linden's Handbook of Batteries, Fourth Edition]. At a certain point, the electrolyte will become saturated with zincates and the reaction product will change to insoluble $Zn(OH)_2$ (2). Eventually, the anode will become depleted of water and the zinc hydroxide dehydrates by equation (3). In rechargeable batteries, the reactions are reversed during charging of the battery. Formation of soluble zincate ions during the initial step of the Zn discharge may hinder recharging.

The cathode reaction involves a reduction of $Mn^{4+}$ to $Mn^{3+}$ by a proton insertion mechanism, resulting in the release of OH⁻ ions (4). The theoretical specific $MnO_2$ capacity for such 1-electron reduction is 308 mAh/g. Slow rate discharge to lower voltages may lead to further discharge of MnOOH as depicted by equation (5), which results in 410 mAh/g total specific capacity (1.33 e). In most prior art applications, the $MnO_2$ discharge is limited to the 1-electron process. Utilization of the active is further adversely affected by the formation of soluble low-valent Mn species.

$$MnO_2+e^-+H_2O \rightarrow MnOOH+OH^- \qquad (4)$$

$$3MnOOH+e^- \rightarrow Mn_3O_4+H_2O+OH^- \qquad (5)$$

$$MnO_2+2e^-+2H_2O \rightarrow Mn(OH)_2+2OH^- \qquad (6)$$

Although $MnO_2$ can theoretically experience a 2-electron reduction according to equation (6) with a theoretical specific capacity of 616 mAh/g, in practice with prior art batteries, it is not demonstrated. The crystalline structure rearrangement with the formation of inactive phases, such as Hausmanite $Mn_3O_4$, and out-diffusion of soluble products are among the factors limiting cathode capacity.

U.S. Pat. No. 7,972,726 describes the use of pentavalent bismuth metal oxides to enhance the overall discharge performance of alkaline cells. Cathode containing 10% $AgBiO_3$ and 90% electrolytic $MnO_2$ was shown to deliver 351 mAh/g to 0.8V cut-off at 10 mA/g discharge rate, compared to 287 mAh/g for 100% $MnO_2$ and 200 mAh/g for 100% $AgBiO_3$. The 351 mAh/g specific capacity corresponds to a 1.13 electron discharge of $MnO_2$ and represents the highest specific capacity delivered at practically useful discharge rates and voltage ranges.

In principle, reaction (4) can be reversible, opening the possibility for a rechargeable $Zn/MnO_2$ battery. In practice, the crystalline structure collapse and formation of soluble products allow only for shallow cycling.

Bismuth- or lead-modified $MnO_2$ materials, disclosed in U.S. Pat. Nos. 5,156,934 and 5,660,953, were claimed to be capable of delivering about 80% of the theoretical 2-electron discharge capacity for many cycles. It was theorized in literature [Y. F. Yao, N. Gupta, H. S. Wroblowa, J. Electroanal. Chem., 223 (1987), 107; H. S. Wroblowa, N. Gupta, J. Electroanal. Chem., 238 (1987) 93; D. Y. Qu, L. Bai, C. G. Castledine, B. E. Conway, J. Electroanal. Chem., 365 (1994), 247] that bismuth or lead cations can stabilize crystalline structure of $MnO_2$ during discharge and/or allow for reaction (6) to proceed via heterogeneous mechanism involving soluble $Mn^{2+}$ species. Containing said $Mn^{2+}$ species seems to be the key for attaining high $MnO_2$ utilization and reversibility. In high carbon content (30-70%) cathodes per U.S. Pat. Nos. 5,156,934 and 5,660,953, the resulting highly porous structure was able to absorb soluble species. However, there is no data to suggest that a complete cell utilizing these cathodes was built or that this worked using a Zn anode.

Thus, a polymer electrolyte which prevents dissolution and transport of low-valent manganese species and zincate ions, would be highly beneficial to improve $MnO_2$ utilization and achieve rechargeability of $Zn/MnO_2$ cells.

In addition to proton insertion, $MnO_2$ can undergo reduction by Li intercalation. It has been suggested [M. Minakshi, P. Singh, J. Solid State Electrochem, 16 (2012), 1487] that the Li insertion can stabilize $MnO_2$ structure upon reduction and enable rechargeability.

The solid, ionically conductive polymer material of the invention, engineered to conduct $Li+$ and $OH^-$ ions, opens the possibility to tune $MnO_2$ discharge mechanism in favor of either proton or lithium insertion, which can serve as an additional tool to improve cycle life.

Accordingly, in one aspect, the invention provides a polymer material including a base polymer, a dopant and at least one compound including an ion source, wherein the polymer material is a solid, ionically conducting polymer material having mobility for $OH^-$ ions. For the purposes of the application, the term "mobility for $OH^-$ ions" refers to a diffusivity of greater than $10^{-11}$ cm$^2$/sec or a conductivity of $10^{-4}$ S/cm, at a room temperature of between 20° C. and 26° C. The solid, ionically conducting polymer material is suitable for use in alkaline cells.

In different aspects, the invention provides an electrolyte including the solid, ionically conductive polymer material having mobility for $OH^-$ ions, wherein the electrolyte is a solid polymer electrolyte for use in alkaline batteries; an electrode or electrodes including said solid polymer electrolyte; and/or a cell or cells including said electrode or electrodes.

Figure 17:
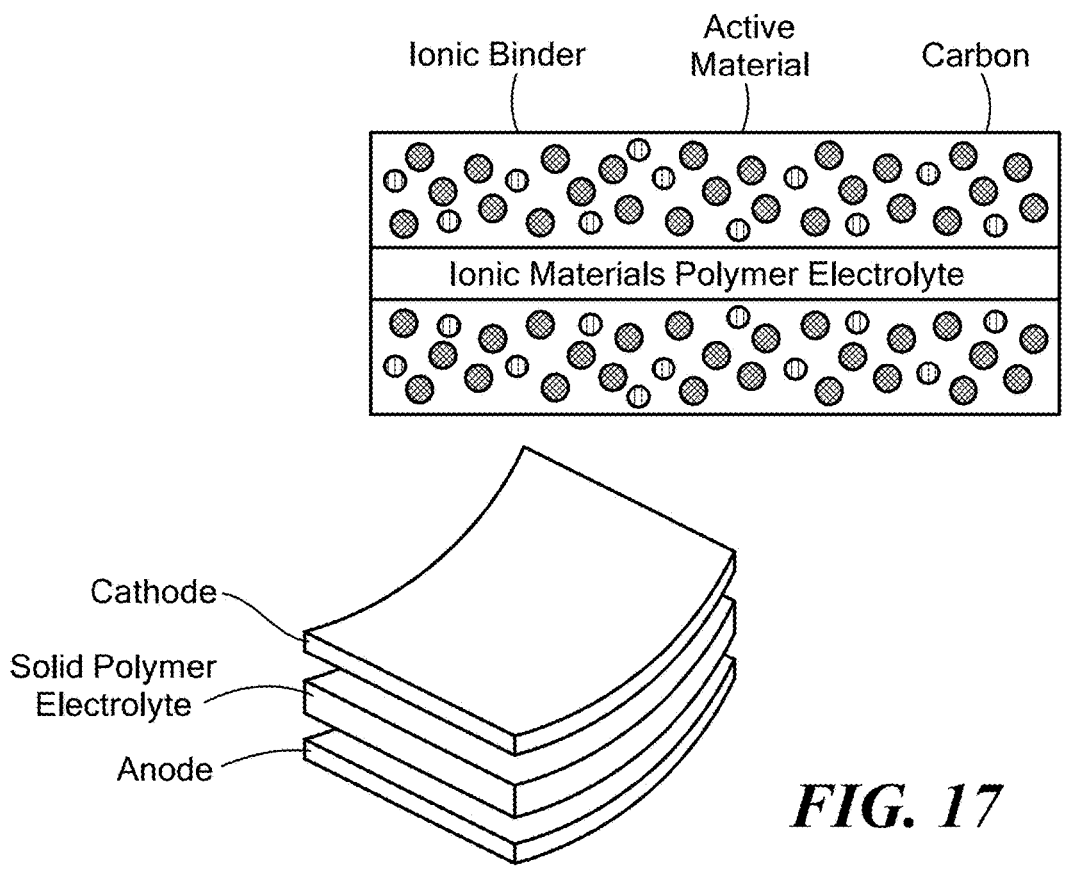
FIG. 17 exemplarily illustrates an alkaline battery having three layers of the invention.

In another aspect, the invention provides electrodes, cathodes and anodes including a solid polymer electrolyte for use in alkaline cells, wherein the solid polymer electrolyte includes a solid, ionically conducting polymer material having mobility for $OH^-$ ions. In yet another aspect, the invention provides an electrolyte interposed between cathode and anode, where at least one of the electrolyte, cathode and anode includes the solid, ionically conductive polymer material having mobility for $OH^-$ ions. In another aspect, the invention provides an alkaline battery including a cathode layer, an electrolyte layer and an anode layer, wherein at least one of the layers includes a solid, ionically conducting polymer material having mobility for $OH^-$ ions. The latter aspect is exemplarily illustrated in FIG. 17.

The base polymer of the solid, ionically conducting polymer material having mobility for $OH^-$ ions is a crystalline or semi-crystalline polymer, which typically has a crystallinity value between 30% and 100%, and preferably between 50% and 100%. The base polymer of this aspect of the invention has a glass transition temperature above 80° C., and preferably above 120° C., and more preferably above 150° C., and most preferably above 200° C. The base polymer has a melting temperature of above 250° C., and preferably above 280° C., and more preferably above 280° C., and most preferably above 300° C.

The dopant of the solid, ionically conducting polymer material having mobility for $OH^-$ ions is an electron acceptor or oxidant. Typical dopants for use in this aspect of the invention are DDQ, TCNE, $SO_3$, etc.

The compound including an ion source of the solid, ionically conducting polymer material having mobility for $OH^-$ ions includes a salt, a hydroxide, an oxide or other material containing hydroxyl ions or convertible to such materials, including, but not limited to, LiOH, NaOH, KOH, $Li_2O$, $LiNO_3$, etc.

The solid, ionically conductive material having mobility for $OH^-$ ions is characterized by a minimum conductivity of $1\times10^{-4}$ S/cm at room temperature and/or a diffusivity of $OH^-$ ions at room temperature of greater than $10^{-11}$ cm$^2$/sec.

The cathode of the present invention relating to $OH^-$ chemistries includes $MnO_2$, NiOOH, AgO, air ($O_2$) or similar active materials. $MnO_2$ is a preferred material and can be in the form of β-$MnO_2$ (pyrolusite), ramsdellite, γ-$MnO_2$, ε-$MnO_2$, λ-$MnO_2$ and other $MnO_2$ phases or mixtures thereof, including, but not limited to, EMD and CMD.

The cathode of the present invention relating to $OH^-$ chemistries is prepared by mixing cathode active material with the components of the solid, ionically conducting polymer material of the invention including the base polymer, the dopant and a compound including a source of ions prior to formation of the solid, ionically conducting polymer material to form a mixture. Alternatively, the cathode active material is mixed with the solid, ionically conducting polymer material already formed.

The mixture is molded and/or extruded at temperatures between 180° C. and 350° C., and preferably between 190° C. and 350° C., and more preferably between 280° C. and 350° C., and most preferably between 290° C. and 325° C. The cathode active material can include various forms such as, for non-limiting examples, a powder form, a particle form, a fiber form, and/or a sheet form. The cathode of the present invention includes active material in an amount of between 10 w. % and 90 wt. %, and preferably in an amount of between 25 wt. % and 90 wt. %, and more preferably in an amount of between 50 wt. % and 90 wt. %, relative to the total cathode weight. The cathode can further include an electrically conductive additive, such as a carbon black component, a natural graphite component, a synthetic graphite component, a graphene component, a conductive polymer component, a metal particles component, and/or other like electrically conductive additives. The cathode can include the electrically conductive additives in an amount of between 0 wt. % and 25 wt. %, and preferably in an amount of between 10 wt. % and 15 wt. % relative to the total cathode weight. The cathode of the present invention relating to $OH^-$ chemistries can further include one or more functional additives for improving performance. The cathode active material can be encapsulated by the solid, ionically conducting polymer material of the invention.

The anode of the present invention relating to OH⁻ chemistries can include an active material of Zn, in the form of zinc powder, zinc flakes and other shapes, zinc sheets, and other shapes. All such forms of zinc can be alloyed to minimize zinc corrosion.

The anode of the present invention relating to OH⁻ chemistries is prepared by mixing anode active material with the components of the solid, ionically conducting polymer material of the invention including the base polymer, the dopant and a compound including a source of ions prior to formation of the solid, ionically conducting polymer material to form a mixture. Alternatively, the anode active material is mixed with the solid, ionically conducting polymer material already formed. The mixture is molded and/or extruded at temperatures between 180° C. and 350° C. The anode of the present invention includes active material in an amount of between 10 w. % and 90 wt. %, and preferably in an amount of between 25 wt. % and 90 wt. %, and more preferably in an amount of between 50 wt. % and 90 wt. %, relative to the total anode weight. The anode can further include an electrically conductive additive, such as a carbon black component, a natural graphite component, a synthetic graphite component, a graphene component, a conductive polymer component, a metal particles component, and/or other like electrically conductive additives. The anode can include the electrically conductive additives in an amount of between 0 wt. % and 25 wt. %, and preferably in an amount of between 10 wt. % and 15 wt. % relative to the total anode weight. The anode of the present invention relating to OH⁻ chemistries can further include one or more functional additives for improving performance. The anode active material can be encapsulated by the solid, ionically conducting polymer material of the invention.

In another aspect, the invention provides a Zn/MnO₂ battery including an electrolyte interposed between a MnO₂ cathode and a Zn anode. The electrolyte in this aspect can include the solid, ionically conducting material of the invention having mobility for OH⁻ ions or can include a traditional separator filled with liquid electrolyte. The cathode can include the solid, ionically conducting material having mobility for OH⁻ ions of the invention or can include a commercial MnO₂ cathode. The anode in this aspect can include the solid, ionically conducting material of the invention having mobility for OH⁻ ions or can include a Zn foil, a Zn mesh or a Zn anode manufactured by other methods. In the Zn/MnO₂ battery of the invention, the solid, electronically conducting polymer material of the invention having mobility for OH⁻ ions is included in at least one of the cathode, the anode and the electrolyte.

III. Polymer-MnO₂ Composite Cathode

The invention further relates to a polymer-MnO₂ composite cathode with a high specific capacity and a primary alkaline cell including the cathode. More specifically, the invention further relates to a polymer-MnO₂ composite cathode with a specific capacity close to theoretical 2-electron discharge and a primary alkaline cell comprising the cathode. The alkaline cell can be discharged at current densities comparable to that of commercial alkaline cells, while useful capacity is delivered to typical 0.8V voltage cut-off.

In different aspects, the invention features a cathode that is made of a MnO₂ active material including a plurality of active MnO₂ particles intermixed with a solid, ionically conductive polymer material including a base polymer, a dopant, and a compound including an ion source and a method of making said cathode. In other aspects, the invention features an electrochemical cell including a cathode, an anode and a separator disposed between the cathode and the anode, and a method for making said cathode. The cathode is made of a MnO₂ active material including a plurality of active MnO₂ particles intermixed with a solid, ionically conductive polymer material including a base polymer, a dopant, and a compound including an ion source. The cathode and the electrochemical cell of the present invention are characterized by flat discharge curves.

In the aspects of the invention related to the polymer-MnO₂ composite cathode, the base polymer can be a semicrystalline polymer. The base polymer can be selected from a group which consists of a conjugated polymer or a polymer which can easily be oxidized. Non-limiting examples of the base polymers used in this aspect of the invention include PPS, PPO, PEEK, PPA, etc.

In the aspects of the invention related to the polymer-MnO₂ composite cathode, the dopant is an electron acceptor or oxidant. Non-limiting examples of dopants are DDQ, tetracyanoethylene also known as TCNE, $SO_3$, ozone, transition metal oxides, including MnO₂, or any suitable electron acceptor, etc.

In the aspects of the invention related to the polymer-MnO₂ composite cathode, the compound including the ion source is a salt, a hydroxide, an oxide or other material containing hydroxyl ions or convertible to such materials, including, but not limited to, LiOH, NaOH, KOH, $Li_2O$, $LiNO_3$, etc.

In the aspects of the invention related to the polymer-MnO₂ composite cathode, the MnO₂ active material can be in the form of β-MnO₂ (pyrolusite), ramsdellite, γ-MnO₂, ε-MnO₂, λ-MnO₂ and other MnO₂ phases or mixtures thereof, including, but not limited to, EMD and CMD.

The cathode related to the polymer-MnO₂ composite cathode can be made prepared by mixing a plurality of active MnO₂ particles and a solid, ionically conducting polymer material including a base polymer, a dopant and a compound including an ion source, and heating the mixture to a specific temperature for a specific time. Said heating can optionally be performed while applying pressure.

In one embodiment, the polymer-MnO₂ composite cathode of the present invention can be prepared by compression molding at a temperature of between The mixture is molded and/or extruded at temperatures between 180 and 350° C., and preferably between 190° C. and 350° C., and more preferably between 280° C. and 350° C., and most preferably between 290° C. and 325° C. In other embodiments, the heating is optionally conducted at a pressure of between 150-2000 PSI, and preferably between 150-1000 PSI and more preferably between 150-500 PSI, and most preferably between 150-250 PSI. The MnO₂ active material can be in an amount of between 5 wt. % and 95 wt. % and preferably between 50 wt. % and 90 wt. % relative to the total weight of the composite cathode. The composite cathode can include a filler in the amount of between 5 wt. % and 50 wt. %, and preferably between 10 wt. % and 50 wt. %, and more preferably between 20 wt. % and 40 wt. %, and most preferably between 25 wt. % and 35 wt. % relative to the total weight of the composite cathode. The dopant can be added in the amount corresponding to a base polymer/dopant molar ratio between 2 and 10, and preferably between 2 and 8, and more preferably between 2 and 6, and most preferably between 3 and 5. The composite cathode can include an electrically conductive additive, such as a carbon black component, a natural and/or a synthetic graphite component, a graphene component, an electrically conductive polymer component, a metal particles component, and another component, wherein the electrically conductive component is in the amount of between 5 wt. % and 25 wt. %, and preferably between 15 wt. % and 25 wt. %, and more preferably between 18 wt. % and 22 wt. % relative to the total weight of the composite cathode. The $MnO_2$ active material in the composite cathode can be encapsulated by solid, ionically conducting polymer material of the invention.

In a preferred embodiment, the invention features an alkaline battery including said polymer-$MnO_2$ composite cathode and a Zn anode. The Zn anode can be in the form of slurry including Zn or Zn alloy powder, KOH, gelling agent and optionally other additives. The Zn anode can further include an electrically conductive additive, similar to the composite cathode.

The anode related to the polymer-$MnO_2$ composite of the invention can include Zn, Al, Fe, metal hydride alloys or similar materials. Zn and Al are preferred materials and can be in the form of pure metals or specially designed alloys. The separator can be a traditional non-woven separator used in alkaline batteries. Electrolyte is KOH, NaOH, LiOH etc. solution in water. Alkali concentration can be between 4 and 9 M. The Electrolyte can further contain an electronically conductive additive and/or a functional additive.

IV. Polymer-sulfur Cathode

In addition, the invention relates to a composite polymer-sulfur cathode. The composite polymer-sulfur cathode includes a sulfur component and a solid, ionically conducting polymer material including a base polymer, a dopant and a compound including a source of ions. The composite polymer-sulfur cathode is characterized as having a high specific capacity and a high capacity retention when employed in a secondary lithium or Li-ion sulfur cell. The composite cathode is characterized as having a specific capacity of greater than 200 milliamp-hr/gm, and preferably greater than 500 milliamp-hr/gm, and more preferably greater than 750 milliamp-hr/gm, and most preferably greater than 1000 milliamp-hr/gm. The composite cathode is characterized as having a retention of least 50% and preferably at least 80% for over 500 recharge/discharge cycles. The composite polymer-sulfur cathode of the present invention has direct application to low-cost, large-scale manufacturing enabled by the unique polymer used in this composite electrode. The composite polymer-sulfur cathode of the invention can provide high performance while simultaneously meeting the requirements for producing low-cost batteries.

Notably, sulfur cathodes reduce during discharge to create sequentially lower order polysulfides through the sequence illustrated in the following equation:

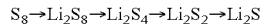

$$S_8 \rightarrow Li_2S_8 \rightarrow Li_2S_4 \rightarrow Li_2S_2 \rightarrow Li_2S$$

The intermediate polysulfides between $Li_2S_8$ and $Li_2S_4$ are soluble in liquid electrolytes. Thus, dissolved polysulfide particles are able to migrate (or "shuttle") across porous separators and react directly with the anode and cathode during cycling. The polysulfide shuttle produces parasitic reactions with the lithium anode and re-oxidation at the cathode, all causing capacity loss. Furthermore, aspects of this shuttle reaction are irreversible, leading to self-discharge and low cycle life that has, until now, plagued lithium sulfur batteries.

The present invention demonstrates a composite polymer-sulfur cathode including a sulfur component and a solid, ionically conducting polymer material. This cathode can be extruded into a flexible, thin film via a roll-to-roll process. Such thin films enable thin, flexible form factors which can be incorporated into novel flexible battery designs. As shown in the examples which follow, this composite polymer-sulfur cathode can include an electrically conductive addition such as, for example, an inexpensive carbon black component, such as Timcal C45, which is already in use for many commercial battery products. In addition to the exemplary carbon black component, the composite polymer-sulfur cathode can include other electrically conductive additives such as, for non-limiting examples, a carbon component including but not limited to carbon fibers, a graphene component, a graphite component, metallic particles or other metal additives, and an electrically conductive polymer.

The engineering properties of the composite polymer-sulfur cathode allow the extrusion of the cathode into a wide range of possible thicknesses, which in turn provides important advantages in terms of flexibility in design in large-scale cathode manufacturing. The composite polymer-sulfur cathode can be extruded as thin as 5 microns and up to thicknesses greater than several 100 microns.

Figure 18:
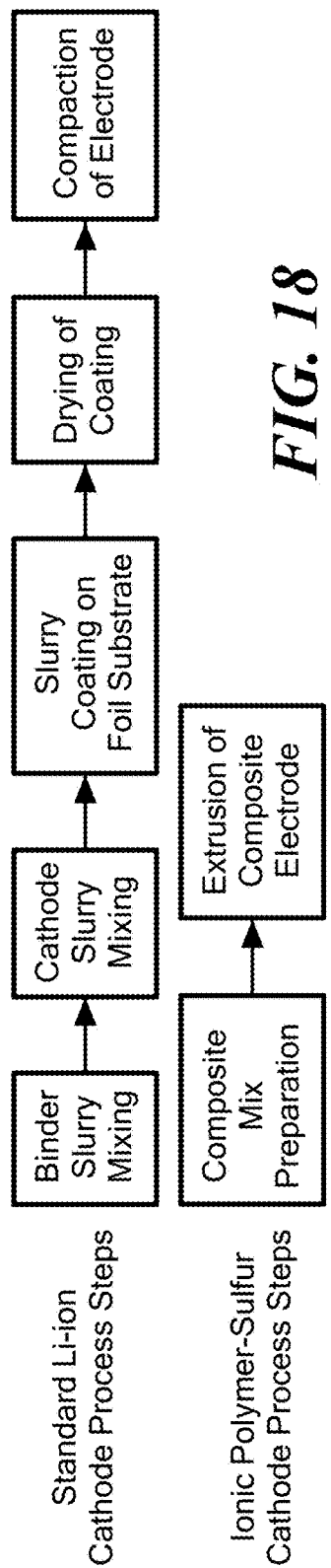
FIG. 18 exemplarily illustrates a comparison of process steps for standard Li-ion cathode manufacturing with those for extrusion of the composite polymer-sulfur cathode of the invention.

A comparison of the process steps necessary for producing standard lithium ion cathodes with those necessary to produce the inventive composite polymer-sulfur cathode is instructive relative to the inherent lower cost of the composite polymer-sulfur cathode manufacturing. FIG. 18 illustrates the process steps needed to manufacture a standard lithium ion cathode compared with the much simpler manufacturing of an extruded composite polymer-sulfur cathode of the invention. The extrusion process for the composite polymer-sulfur cathode is easily scaled-up to high volume manufacturing which provides a significant advantage over existing lithium ion battery, as well as a much lower capital expenditure for factory equipment.

In addition to extrusion, the composite polymer-sulfur cathode can be formed by injection molding, compression molding, or any other process involving heat, or other techniques known by those skilled in the art for engineering plastics.

The composite polymer-sulfur cathode includes a sulfur component and a solid, ionically conducting polymer material including a base polymer, a dopant and a compound including a source of ions, as discussed above.

The base polymer includes liquid crystal polymers and polyphenylene sulfide (PPS), or any semicrystalline polymer with a crystallinity index greater than 30%, or other typical oxygen acceptors.

The dopant includes electron acceptors which activate the ionic conduction mechanism. These electron acceptors can be pre-mixed along with the other ingredients, or supplied in the vapor phase as a post doping process. Typical electron acceptor dopants suitable for use include, but are not limited to: 2,3-dichloro-5,6-dicyano-1,4-benzoquinone (DDQ) ($C_8Cl_2N_2O_2$), Tetracyanoethylene (TCNE) ($C_6N_4$), and sulfur trioxide ($SO_3$).

The compounds including an ion source include, but are not limited to $Li_2O$ and LiOH. Use of composite polymer-sulfur cathodes in Li/Sulfur test cells has shown that the composite polymer-stable cathodes are stable to lithium, sulfur, and organic electrolytes typically used in lithium/sulfur batteries.

The base polymer is a nonflammable polymer which has been shown to self-extinguish and pass the UL-VO Flammability test. The non-flammability of the base polymer is a safety benefit to batteries employing the composite polymer-sulfur cathode. The incorporation of the non-flammable composite polymer-sulfur cathode into a cell with nonflammable electrolyte will further improve the safety of the battery, an important attribute for high energy density batteries.

The sulfur component can include non-reduced and/or reduced forms of sulfur including elemental sulfur. In particular, the composite polymer-sulfur cathode includes a sulfur component including the fully lithiated form of sulfur ($Li_2S$), wherein the $Li_2S$, is a solid. The composite polymer-sulfur cathode can also include a carbon component. The advantage to using the fully lithiated form of sulfur is that it provides a lithium source for a sulfur battery with a Li Ion anode, which, unlike metal Li, must by lithiated during initial charge. Combination of a sulfur cathode with a Li-ion anode provides benefit in preventing the formation of lithium dendrites which can be formed after cycling lithium anodes. Dendrites are caused by a non-uniform plating of lithium onto the lithium metal anode during charging. These dendrites can grow through separator materials and cause internal short circuits between cathode and anode, often leading to high temperatures and compromised safety of the battery. Materials that reversibly incorporate lithium, either through intercalation or alloying, lessen the chance for dendrite formation and have been proposed for use in high safety lithium/sulfur cells. The composite polymer-sulfur cathode can be used with an anode material such as, for example, a carbon-based (petroleum coke, amorphous carbon, graphite, carbon nano tubes, graphene, etc.) material, Sn, SnO, $SnO_2$ and Sn-based composite oxides, including composites with transition metals, such as Co, Cu, Fe, Mn, Ni, etc. Furthermore, silicon has shown promise as a lithium ion anode material, in the elemental form, or as an oxide or composite material, as described for tin. Other lithium alloying materials (for example, Ge, Pb, B, etc.) could also be used for this purpose. Oxides of iron, such as $Fe_2O_3$ or $Fe_3O_4$ and various vanadium oxide materials have also been shown to reversibly incorporate lithium as a Li-ion anode material. Anode materials may be considered in different forms, including amorphous and crystalline, and nano-sized particles as well as nano-tubes.

The composite polymer-sulfur cathode can be combined with a standard liquid electrolyte, a standard nonwoven separator, and/or an electrolyte including a solid, ionically conducting polymer material with no liquid electrolyte. An example of a standard organic electrolyte solution includes a lithium salt, such as lithium bis(trifluoromethane sulfonyl) imide (LiTFSI), dissolved in a mixture of 1,3-dioxolane (DOL) and 1,2-dimethoxyethane (DME). Additives, such as $LiNO_3$, can be added to the electrolyte to improve cell performance. Other lithium salts can be utilized in organic liquid electrolyte, including: $LiPF_6$, $LiBF_4$, $LiAsF_6$, lithium triflate, among others. Additionally, other organic solvents can be used, such as propylene carbonate (PC), ethylene carbonate (EC), diethyl carbonate (DEC), dimethyl carbonate (DMC), ethyl methyl carbonate (EMC), fluoroethylene carbonate (FEC), as a few examples, either alone or as mixtures together or with DOL and DME. Examples of standard nonwoven separators include polypropylene (PP), polyethylene (PE), and combinations of PP/PE films. Other separator materials include polyimide, PTFE, ceramic coated films and glass-mat separators. All of the above materials can be used with the composite polymer-sulfur cathode. Further, the composite polymer-sulfur cathode could also be utilized in a gel-polymer system, where for example, a PVDF-based polymer is swelled with an organic electrolyte.

It is believed that the ability of the composite polymer-sulfur cathode to provide lithium ionic conductivity improves the performance of the cell by limiting the polysulfide shuttle mechanism, while simultaneously providing a sulfur cathode with high voltage. Furthermore, this unique engineering composite polymer-sulfur cathode allows for the large scale, low cost manufacturing necessary for commercial viability of the cathode.

Thus, the unique composite polymer-sulfur cathode has numerous potential benefits to batteries, including:
  Improved safety, under normal and abuse conditions
  Enabling new battery form factors
  Large increase in energy density over existing Li-ion cells
  Prevention of the polysulfide shuttle mechanism, leading to greater charge/discharge reversibility
  Large decrease in manufacturing cost (raw materials, process and capital equipment) leading to improvement in the cost of energy storage V. Alkaline Cells In an aspect, a rechargeable $Zn/MnO_2$ battery for low rate applications that can match or surpass lithium-ion performance while delivering improved safety, robustness, and lower cost is described.

Figure 38:
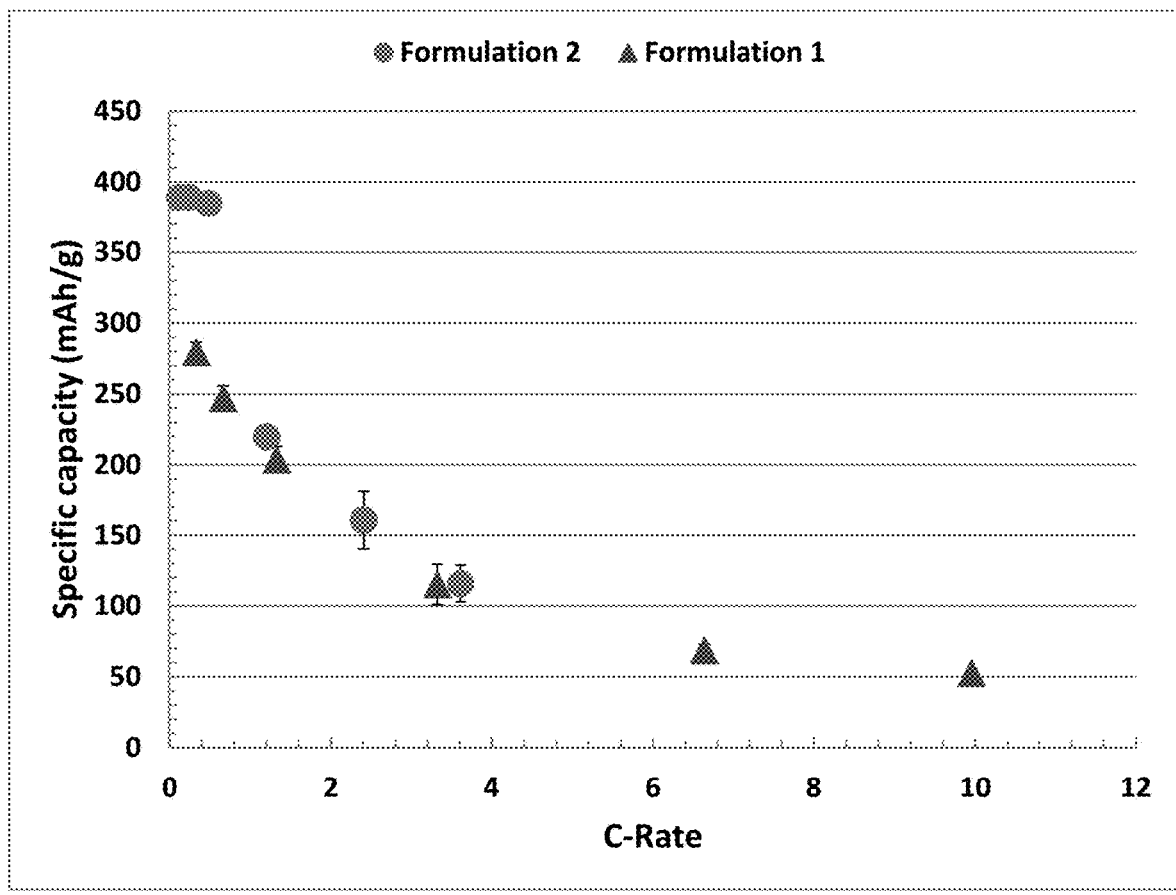
FIG. 38 shows rate profiles of coin cells.

It has been observed that certain cathode formulations comprising the solid ionically conductive polymer material can demonstrate much higher active material utilization at low rates, while displaying steeper decline upon the discharge rate increase. This is illustrated by FIG. 38, which depicts rate profiles of coin cells with cathode formulations potentially useful for high energy cells. Most of such formulations demonstrate specific C/2 capacity of about 300 mAh/g, which is close to the theoretically expected for the single-electron discharge of MnO2 (illustrated by Formulation 1 in FIG. 38). In some cases, cells demonstrate specific capacity exceeding theoretical single-electron discharge. For example, Formulation 2 demonstrated almost 400 mAh/g at C/2 discharge, illustrating deeper discharge of manganese dioxide.

Zinc and polymer content in the anode were optimized, specifically: zinc type and particle size, composition and process to make solid polymer electrolyte for the desired anode performance, and ZnO and other functional additives were introduced to reduce zinc passivation. The combined effect of higher zinc surface area and improved stability result in improved performance and prolonged cycle life. Embedding Zn particles into the polymer matrix prevents shape change, agglomeration and dendrite growth.

Figure 39:
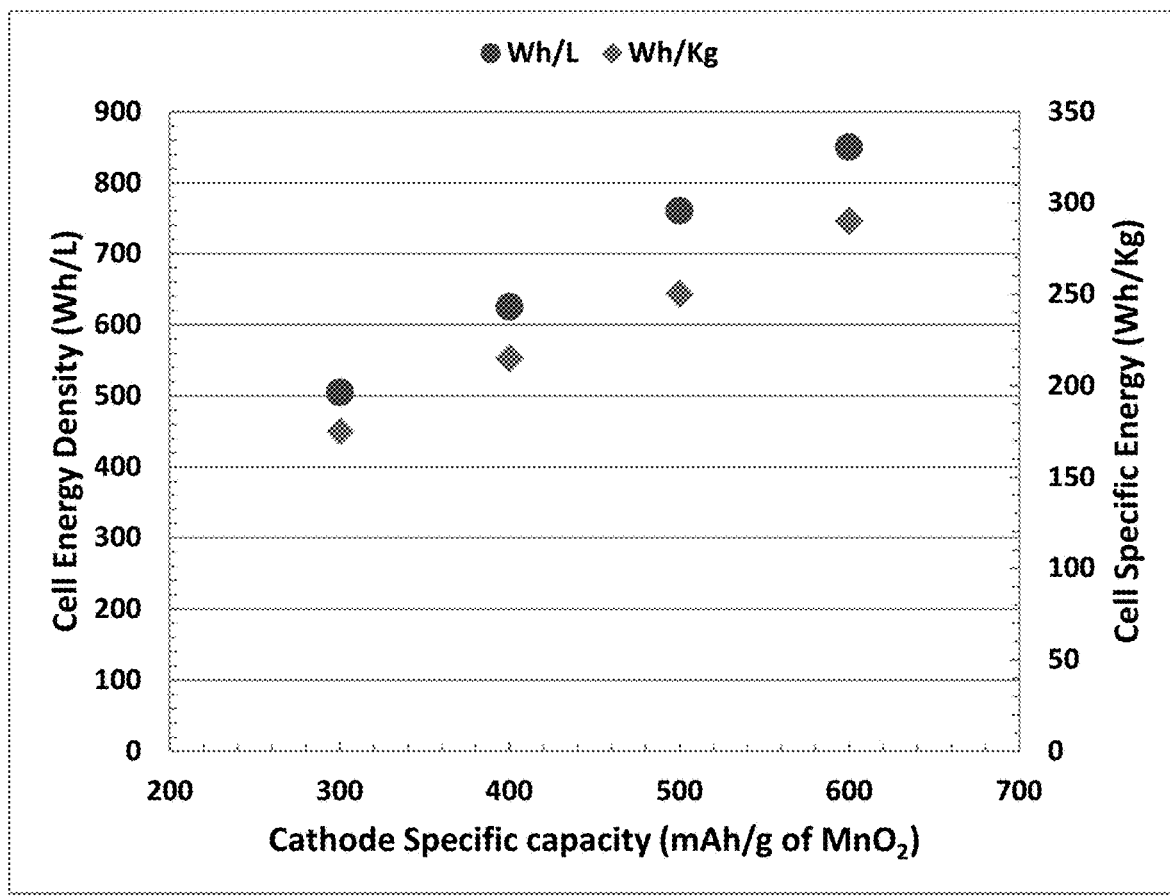
FIG. 39 shows cathode capacity in relation to cell energy density.

The cathode, optimized to increase capacity above 300 mAh/g shows specific MnO2 capacity improvement that has a drastic impact on the cell energy density of pouch cells as illustrated by FIG. 39.

In an aspect, a rechargeable $Zn/MnO_2$ batteries incorporating the solid ionically conducting polymer material for high rate and high temperature applications is described.

Figure 40:
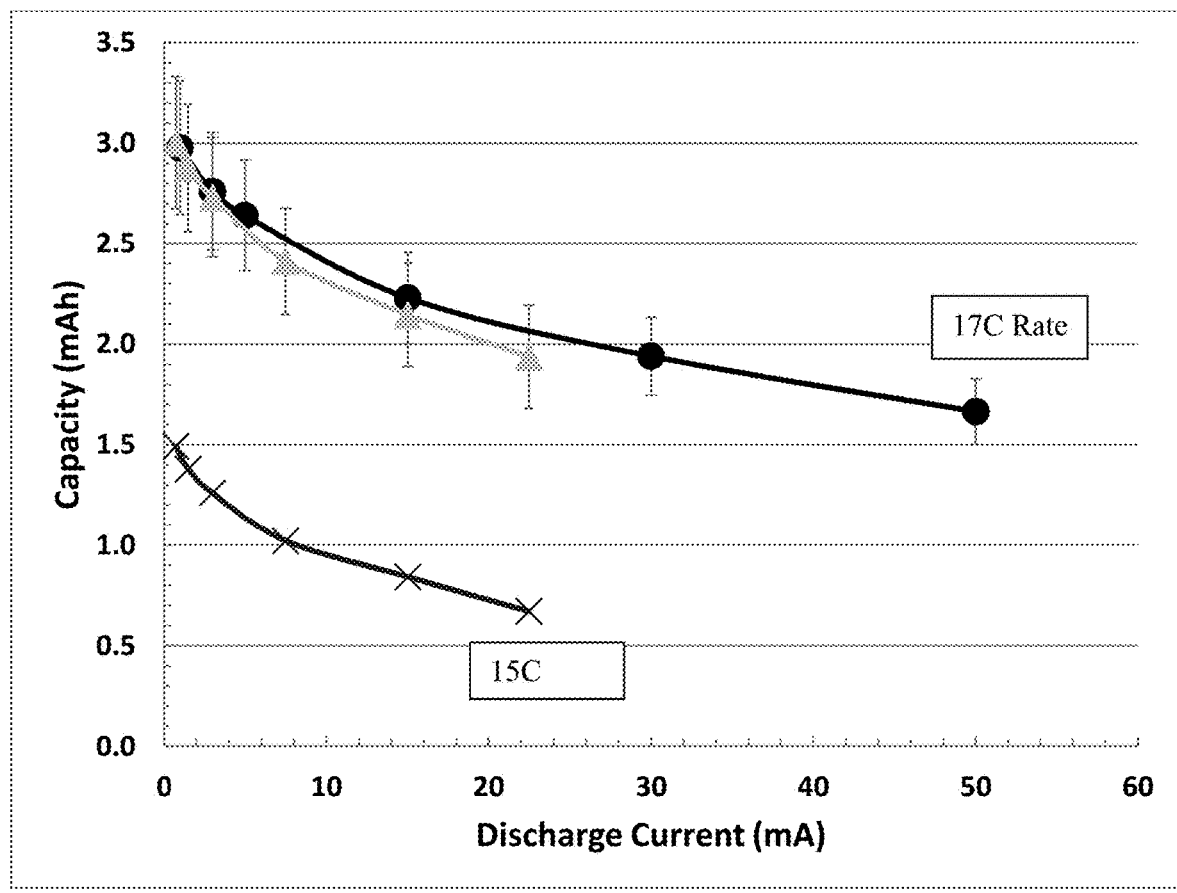
FIG. 40 shows coin cell discharge capacity in relation to discharge current.

Good active material utilization and high-rate performance of coin cells is preserved upon increasing manganese dioxide content 80% by weight or above. Since high active material loadings are essential to achieving high energy density, the significance of this finding is hard to overstate. The improvements in discharge capacity resulting from optimization of the manganese dioxide content are shown in FIG. 40. As can be seen, the optimized cells performed well even at currents as high as 50 mA (extremely high for a coin cell), at which level anode and coin cell hardware limitations may start playing a role.

Cathode densities of 2.5-3.0 g/cc are sufficient to attain high energy density. High-rate performance under these conditions can be limited by a zinc foil anode, rather than the cathode. A zinc anode with increased surface area to replace zinc foil shows improved performance.

To increase the anode rate capability and improve cycle life, the anode is improved by optimizing zinc and anode polymer content, optimizing zinc type and particle size, and introducing ZnO and other functional additives (such as manganese salts) to reduce zinc passivation and corrosion. The combined effect of higher zinc surface area and improved stability results in improved performance at high discharge rates and prolonged cycle life. Further it was found that embedding zinc particles into the polymer matrix prevents shape change, agglomeration and dendrite growth.

Cells matching or surpassing current state-of-the-art Li-ion systems in energy/power density, demonstrating >85% capacity retention at 15 C discharge; safe to operate at 80-100° C.; and having a minimum life of 500 cycles were produced. These packs of Zn/MnO2 cells will not require complicated battery management and charge control circuitry, and additional energy density benefits and cost reduction is expected on the pack level.

EXAMPLE 1

Solid polymer electrolyte was made by mixing PPS base polymer and ion source compound LiOH monohydrate in the proportion of 67% to 33% (by wt.), respectively, and mixed using jet milling. DDQ dopant was added to the resulting mixture in the amount of 1 mole of DDQ per 4.2 moles of PPS. The mixture was heat treated at 325/250° C. for 30 minutes under moderate pressure (500-1000 PSI). After cooling, the resulting material was grinded and placed into NMR fixture.

Figure 19:
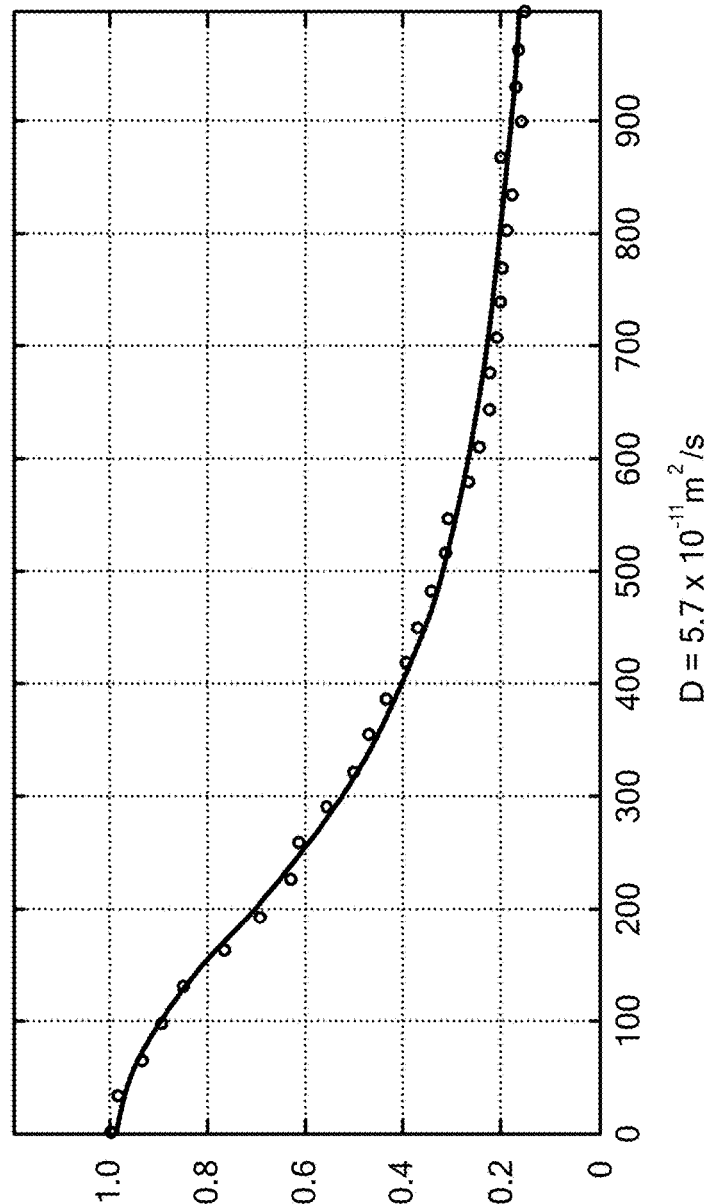
FIG. 19 exemplarily illustrates $OH^-$ diffusivity at room temperature in a solid polymer electrolyte of the invention.
Figure 20:
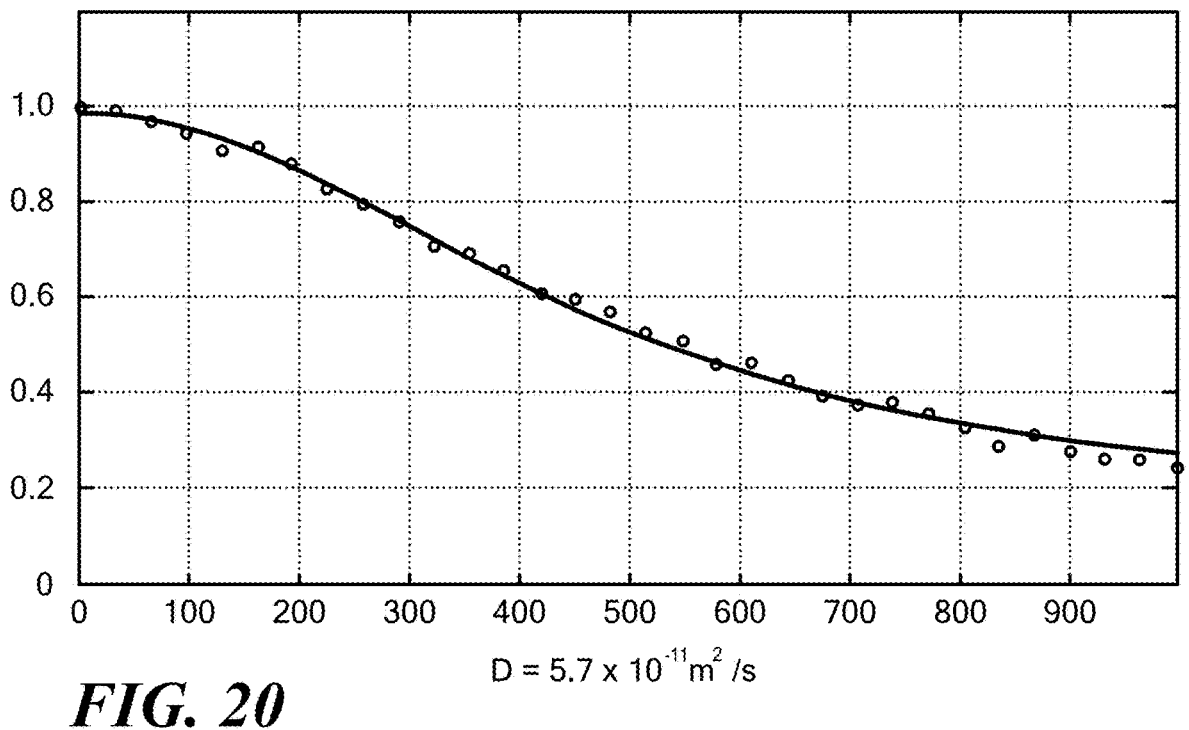
FIG. 20 exemplarily illustrates lithium diffusivity at room temperature in a solid polymer electrolyte of the invention.

Self-diffusion coefficients were determined by using pulsed field gradient solid state NMR technique. The results shown in FIGS. 19 and 20 indicate, respectively, that $Li^+$ and $OH^-$ diffusivity in the solid polymer electrolyte is the highest of any known solid, and over an order of magnitude higher at room temperature compared to recently developed $Li_{10}GeP_2S_{12}$ ceramic at much higher temperatures (140° C.) or the best PEO formulation at 90° C.

EXAMPLE 2

PPS base polymer and ion source compound LiOH monohydrate were added together in the proportion of 67 wt. % to 33 wt. %, respectively, and mixed using jet milling. Cathode was prepared by additionally mixing 50% β-MnO2 from Alfa Aesar, 5% of Bi2O3 and 15% of C45 carbon black. DDQ dopant was added to the resulting mixture in the amount of 1 mole of DDQ per 4.2 moles of PPS.

The mixture was compression molded onto stainless steel mesh (Dexmet) at 325/250° C. for 30 minutes under moderate pressure (500-1000 PSI), yielding cathode disc 1 inch in diameter and about 0.15 mm thick. The resulting disc was punched to 19 mm diameter and used as a cathode to assemble test cells, containing commercial non-woven separator (NKK) and Zn foils anode. 6M LiOH was added as electrolyte.

Figure 21:
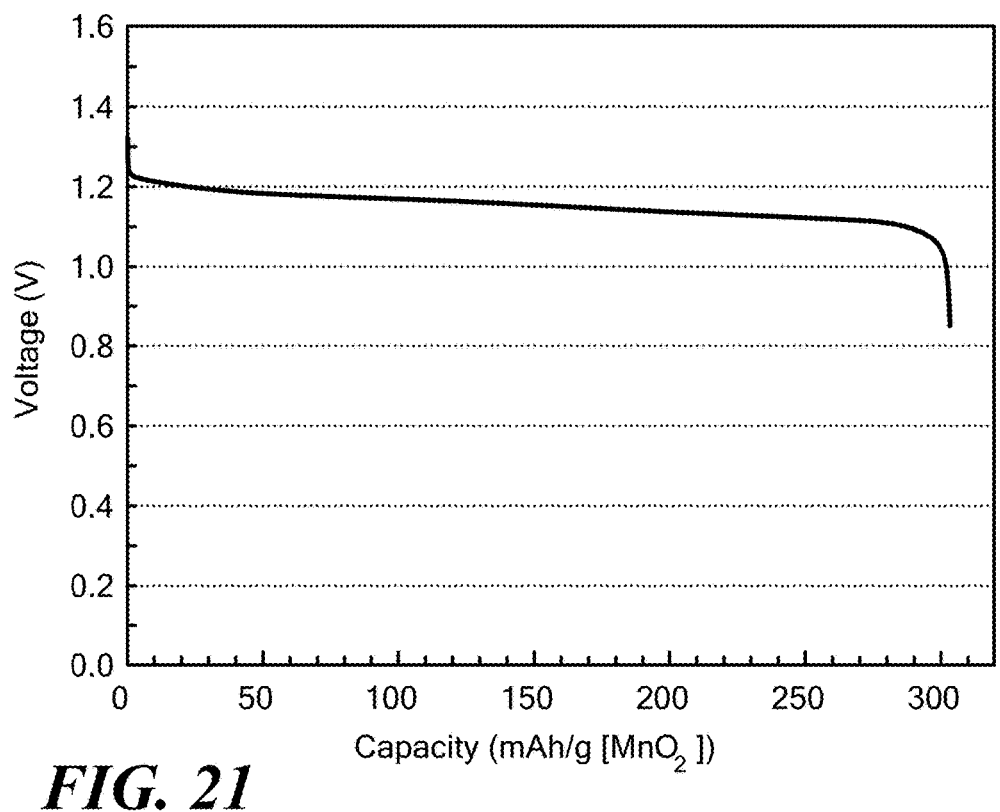
FIG. 21 exemplarily illustrates voltage profile of cell of the invention per example 2 as a function of specific capacity of $MnO_2$ at 0.5 $mA/cm^2$ discharge rate.

Cells were discharged under constant current conditions of 0.5 mA/cm$^2$ using Biologic VSP test system. The specific capacity of $MnO_2$ was 303 mAh/g or close to theoretical 1e$^-$ discharge. FIG. 21 illustrates the voltage profile of the cell per Example 2 as a function of specific capacity of $MnO_2$ at 0.5 mA/cm$^2$ discharge rate.

EXAMPLE 3

PPS base polymer and ion source compound LiOH monohydrate were added together in the proportion of 67% to 33% (by wt.), respectively, and mixed using jet milling. Cathode was prepared by additionally mixing 50% β-MnO$_2$ form Alfa Aesar, 5% of $Bi_2O_3$ and 15% of C45 carbon black. DDQ dopant was added to the resulting mixture in the amount of 1 mole of DDQ per 4.2 moles of PPS.

The mixture was compression molded onto stainless steel mesh (Dexmet) at 325/250 C for 30 minutes under moderate pressure (500-1000 psi), yielding cathode disc 1" in diameter and 1.6-1.8 mm thick.

The resulting cathodes were used to assemble test cells, containing commercial non-woven separator (NKK) and Zn anode slurry extracted from commercial alkaline cells. 6M KOH solution in water was used as electrolyte.

Cells were discharged under constant current conditions using Biologic VSP test system. The specific capacity of $MnO_2$ was close to 600 mAh/g at C/9 discharge rate (35 mA/g), or close to theoretical 2 e$^-$ discharge.

Figure 22:
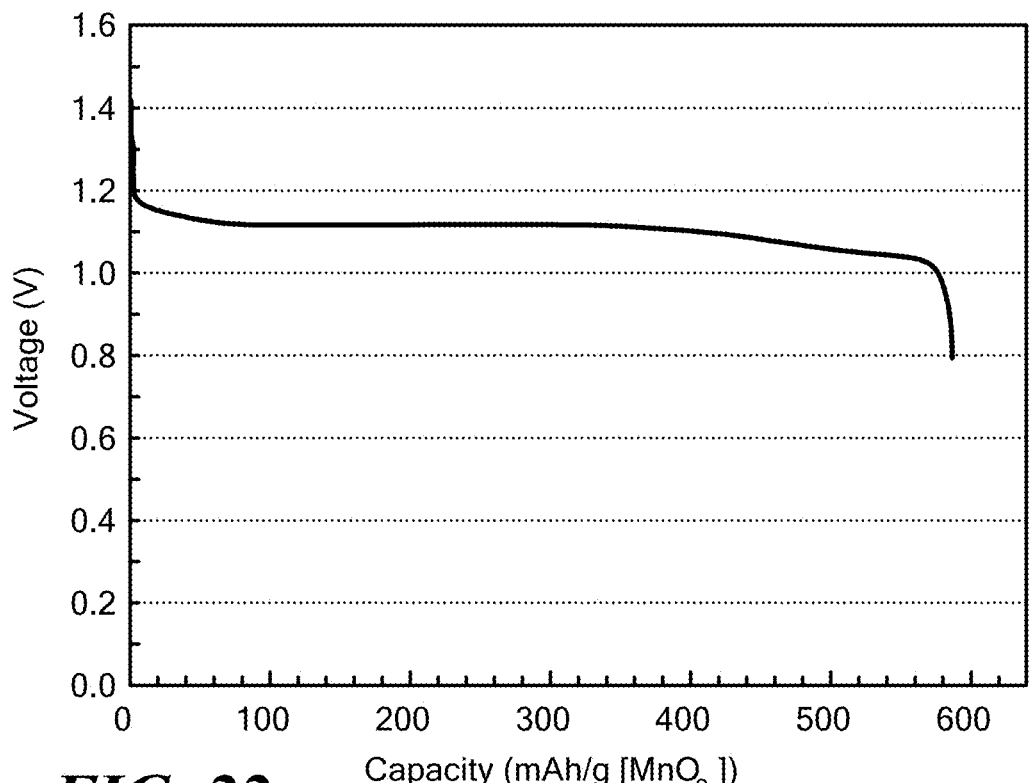
FIG. 22 exemplarily illustrates voltage profile of cell of the invention per example 3 as a function of specific capacity of $MnO_2$ at C/9 rate (35 mA/g)

FIG. 22 shows the voltage profile of the cell per Example 3 as a function of specific capacity of $MnO_2$ at C/9 rate (35 mA/g).

EXAMPLE 4

PPS base polymer and ion source compound LiOH monohydrate were added together in the proportion of 67% to 33% (by wt.), respectively, and mixed using jet milling. Cathode was prepared by additionally mixing 50% β-MnO$_2$ form Alfa Aesar, 5% of $Bi_2O_3$ and 15% of C45 carbon black. DDQ dopant was added to the resulting mixture in the amount of 1 mole of DDQ per 4.2 moles of PPS.

The mixture was compression molded onto stainless steel mesh (Dexmet) at 325/250° C. for 30 minutes under moderate pressure (500-1000 PSI), yielding cathode disc 1inch in diameter and about 0.15 mm thick.

The resulting disc was punched to 19 mm diameter and used as a cathode to assemble test cells, containing commercial non-woven separator (NKK) and Zn foil anode. 6M LiOH was added as electrolyte.

Figure 23:
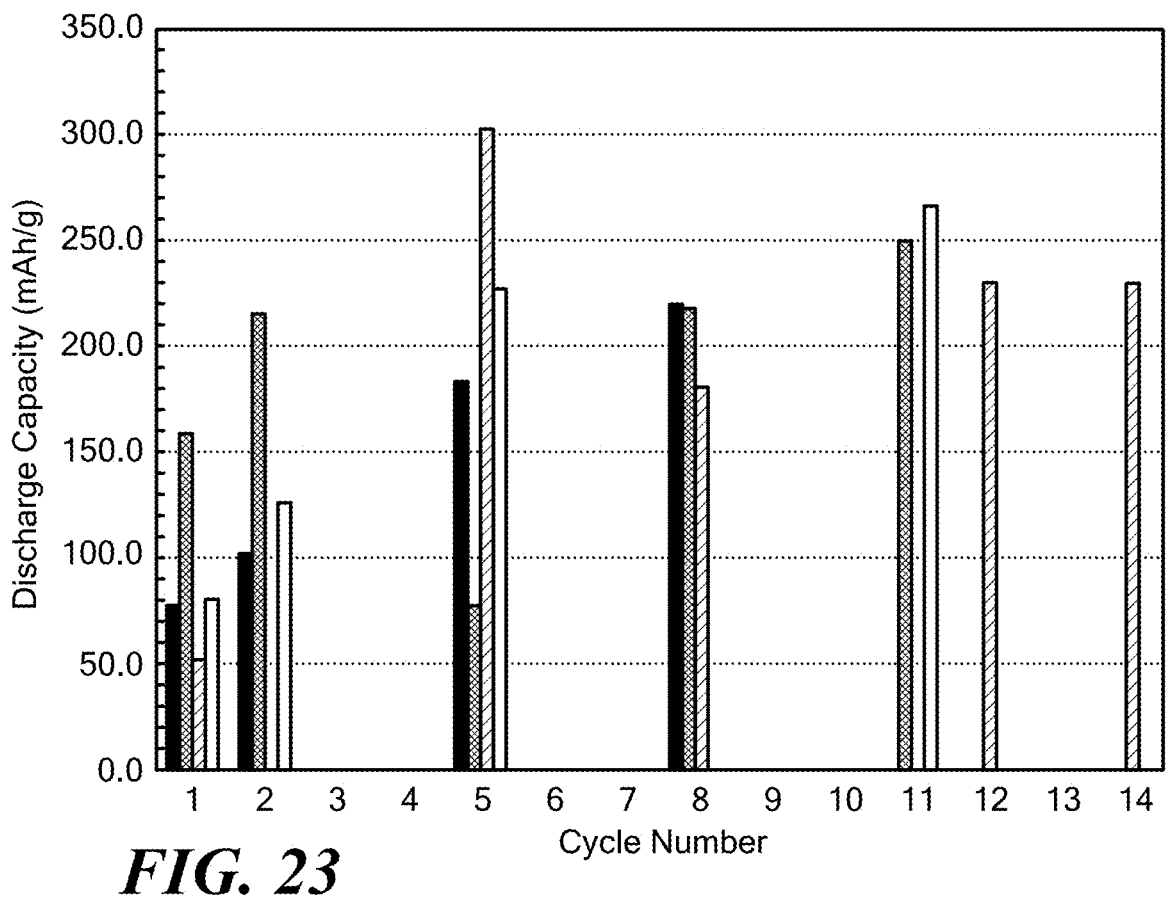
FIG. 23 exemplarily illustrates specific capacity of $MnO_2$ as a function of cycle number in the cells of the invention per example 4.

The cells were discharged and charged using a Biologic VSP test system. Discharge was conducted at 0.5 mA/cm$^2$ current to 0.8 V cut-off. Charge was performed at 0.25 mA/cm$^2$ to 1.65 V, then held at 1.65V for 3 hours or until current declined to 0.02 mA/cm$^2$. Every few cycles passivated Zn anode and separator were replaced with fresh. Specific capacity of $MnO_2$ as a function of cycle number in cells per Example 4 is plotted at FIG. 23. Each column represents separate cell. Only discharges with fresh Zn anode are shown. It is easy to see that $MnO_2$ cathode of present invention is rechargeable. Only discharges with fresh Zn anode are shown.

EXAMPLE 5

Figure 24:
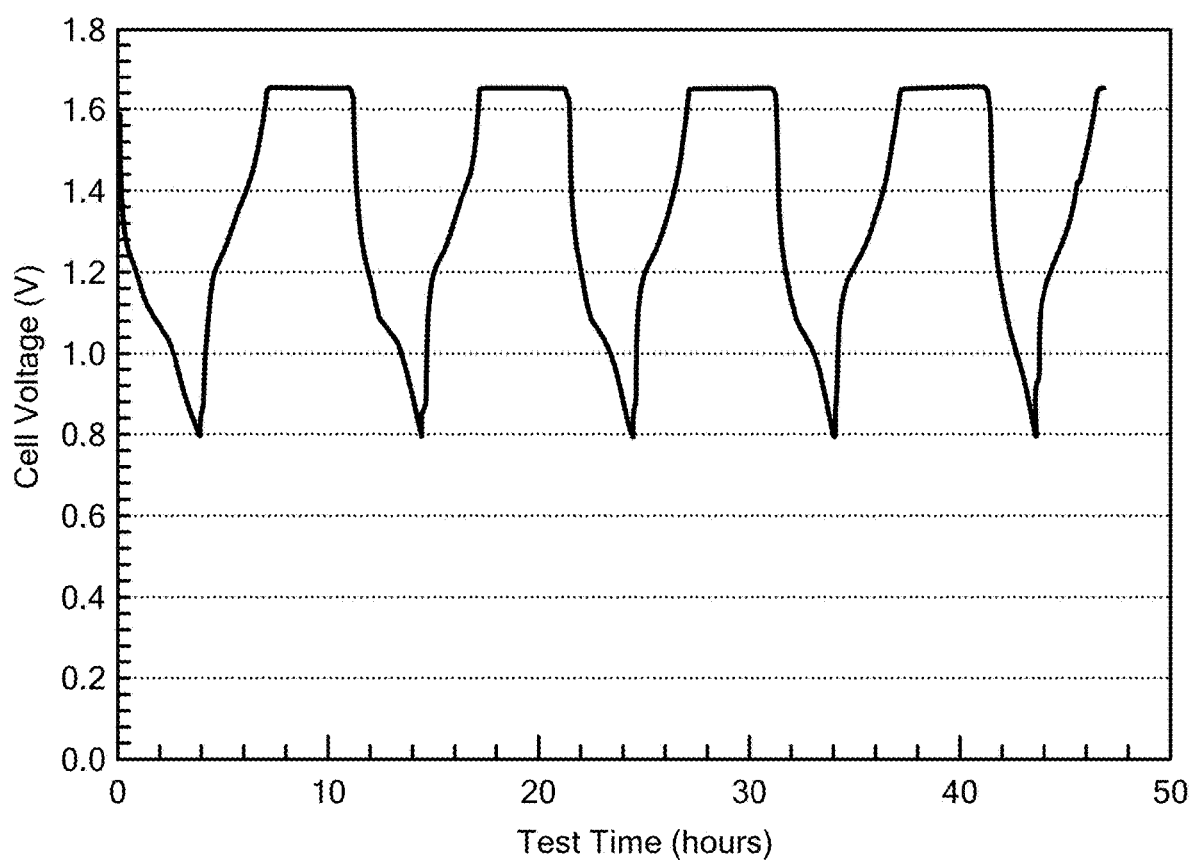
FIG. 24 exemplarily illustrates discharge curve of coin cell of the invention per example 5 as a function of test time.

A 2035 coin cell was assembled using the solid polymer electrolyte of Example 1, the cathode of Example 2 and a Zn foil as anode. The cell was discharged and charged using a Biologic VSP test system. Discharge was conducted at 0.25 mA/cm$^2$ current to 0.8 V cut-off. Charge was performed at 0.25 mA/cm$^2$ to 1.65 V, then held at 1.65V for 3 hours or until current declined to 0.02 mA/cm$^2$. The cell demonstrated reversible behavior during such cycling. FIG. 24 shows the discharge curve of the coin cell per Example 5 as a function of test time.

EXAMPLE 6

PPS base polymer and ion source compound LiOH monohydrate were added together in the proportion of 67% to 33% (by wt.), respectively, and mixed using jet milling. Cathode was prepared by additionally mixing 55% β-$MnO_2$ form Alfa Aesar and 15% of C45 carbon black. DDQ dopant was added to the resulting mixture in the amount of 1 mole of DDQ per 4.2 moles of PPS.

The mixture was compression molded onto stainless steel mesh (Dexmet) at 325/250 C for 30 minutes under moderate pressure (500-1000 psi), yielding cathode disc 1inch in diameter and about 0.15 mm thick.

Figure 25:
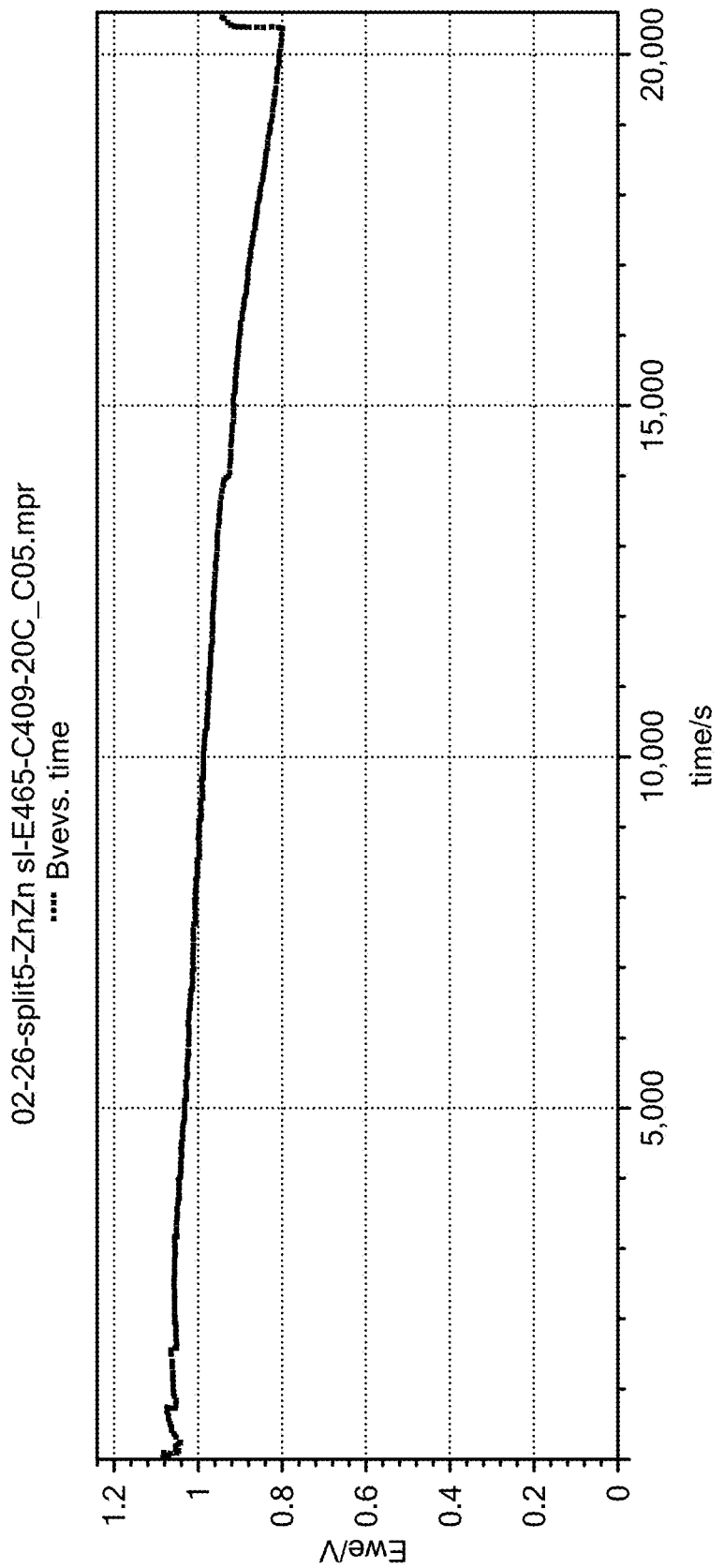
FIG. 25 exemplarily illustrates voltage profile of the cell of the invention per example 6 as a function of test time.

The test cell was assembled using the resulting cathode, electrolyte per Example 1 and anode made of Zn powder. The cell was discharged using Biologic VSP test system at 0.5 mA/$cm^2$ current density to 0.8 V cut-off. Specific capacity of $MnO_2$ was 401 mAh/g or more than theoretical 1-electron discharge. FIG. 25 shows the voltage profile of the cell per Example 6 as a function of test time.

EXAMPLE 7

PPS base polymer and ion source compound LiOH monohydrate were added together in the proportion of 67% to 33% (by wt.), respectively, and mixed using jet milling. Anode was prepared by additionally mixing 60% of Zn powder and 10% of C45 carbon black. DDQ dopant was added to the resulting mixture in the amount of 1 mole of DDQ per 4.2 moles of PPS.

The mixture was compression molded onto stainless steel mesh (Dexmet) at 325/250 C for 30 minutes under moderate pressure (500-1000 psi), yielding cathode disc 1" in diameter and about 0.15 mm thick.

The 2035 coin cell was assembled using the resulting anode, cathode per example 2 and commercial NKK separator, containing saturated LiOH as electrolyte.

The control coin cell was made using Zn foil as anode, cathode per Example 2 and commercial NKK separator containing saturated LiOH as electrolyte.

Figure 26:
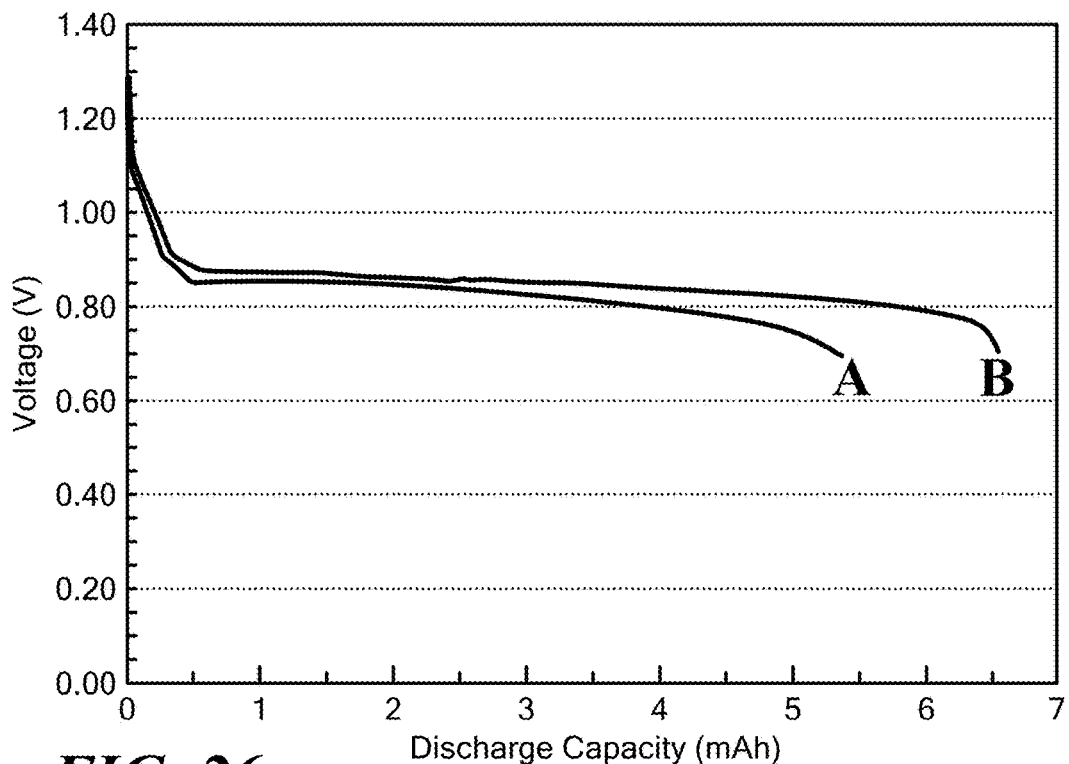
FIG. 26 exemplarily illustrates discharge curve of coin cells of the invention per example 7 as a function of discharge capacity.

The cells were discharged using a Biologic VSP test system at 0.5 mA/$cm^2$ current density. The discharge profile with anode of the present invention shows higher capacity at slightly higher voltage, which can be related to increased surface area of Zn anode and retention of soluble zincates inside the anode structure. FIG. 26 shows the discharge curve of coin cells per Example 7 as a function of discharge capacity. Discharge was conducted at 0.25 mA/$cm^2$ current to 0.7 V cut-off Curve A—cell with anode of the present invention. Curve B—cell with Zn foil anode. FIG. 26 shows the discharge curve of coin cells per Example 7 as a function of discharge capacity. Discharge was conducted at 0.25 mA/$cm^2$ current to 0.7 V cut-off. Curve A—cell with anode of the present invention. Curve B—cell with Zn foil anode.

EXAMPLE 8

PPS base polymer and an ion source compound LiOH monohydrate were added together in the proportion of 67% to 33% (by wt.), respectively, and mixed using jet milling. Anode was prepared by additionally mixing 60% of Al powder and 10% of C45 carbon black. DDQ dopant was added to the resulting mixture in the amount of 1 mole of DDQ per 4.2 moles of PPS. The mixture was compression molded onto stainless steel mesh (Dexmet) at 325/250 C for 30 minutes under moderate pressure (500-1000 psi), yielding cathode disc 1" in diameter and about 0.15 mm thick.

The resulting anode was tested in test cell containing Zn counter electrode and commercial separator containing $ZnSO_4$ electrolyte. Anode made of Al foil was tested as a control.

Figure 27:
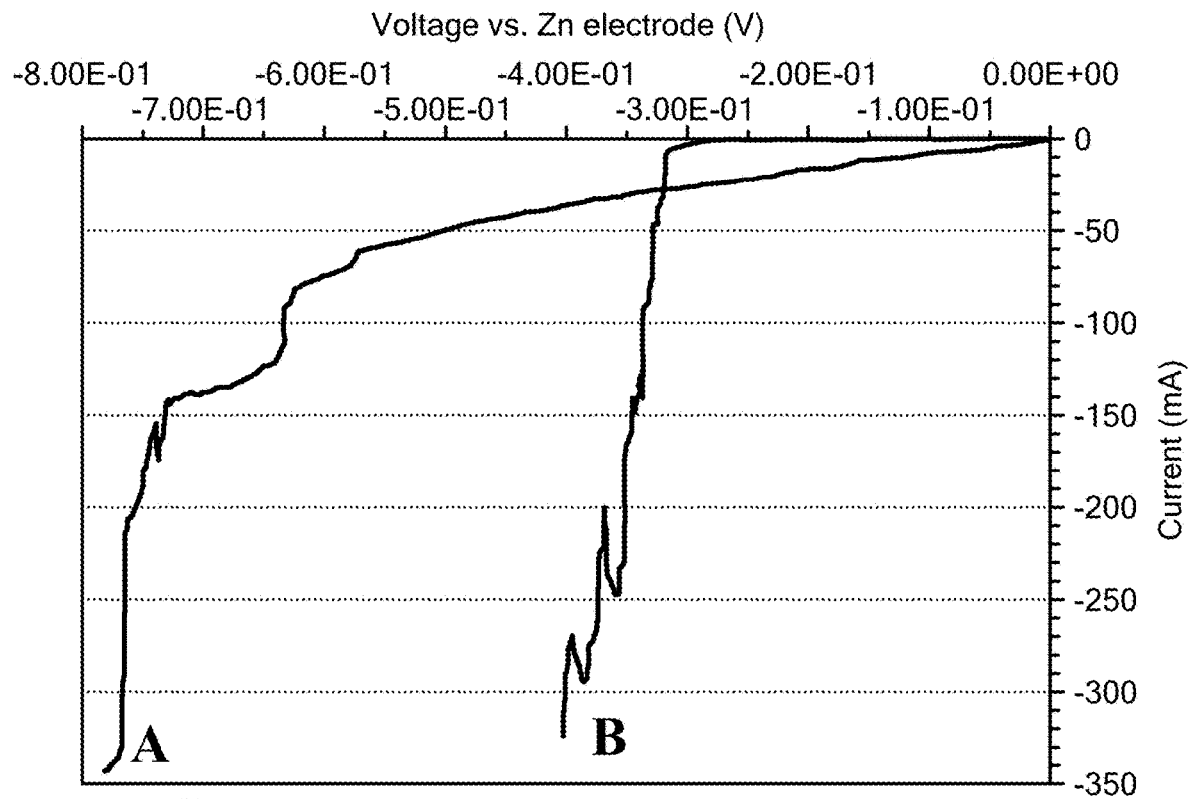
FIG. 27 exemplarily illustrates a potentiodynamic scan at 1 mV/s of anode of the present invention (curve A) and control Al foil (curve B) in $ZnSO_4$ electrolyte. Zn foil was used as counter electrode.

The anode was polarized potentiodynamically at 1 mV/s sweep rate using Biologic VSP test system. FIG. 27 shows a potentiodynamic scan at 1 mV/s of anode of the present invention (curve A) and control Al foil (curve B) in $ZnSO_4$ electrolyte. Anode of the present invention demonstrated corrosion stability improved by 0.5 V compared to Al foil.

COMPARATIVE EXAMPLE 9

Figure 28:
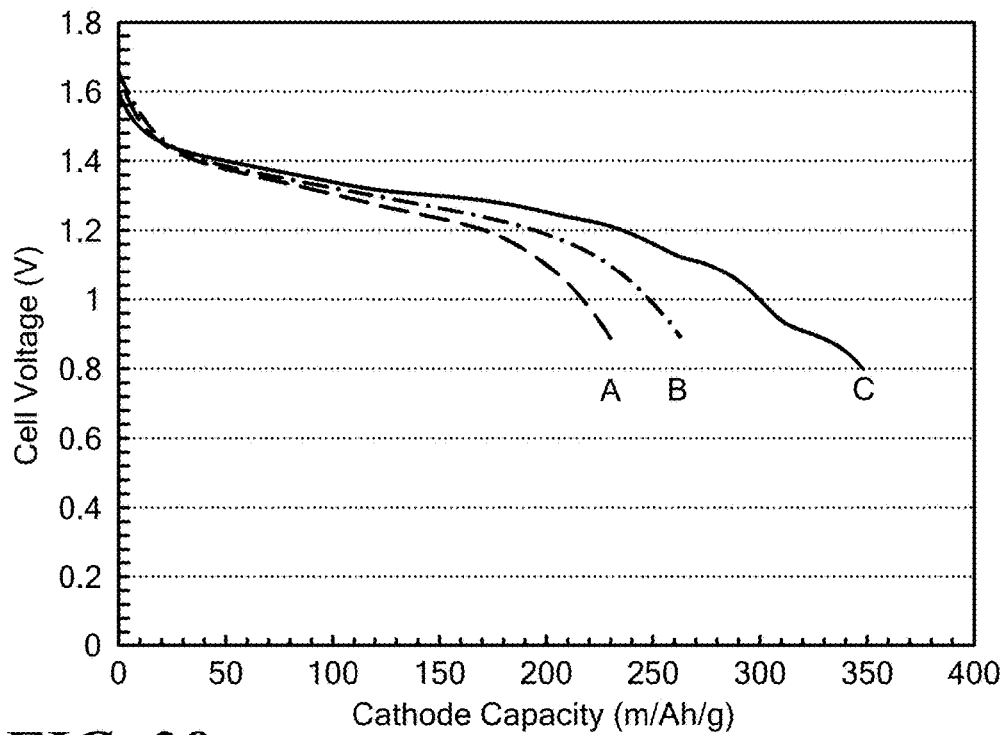
FIG. 28 illustrates specific capacity of Duracell Coppertop AA cell under different constant current discharge rates.

Discharge profile of Duracell Coppertop AA cell at 250 mA discharge was taken from the datasheet. Amount of $MnO_2$ in the cell was calculated by comparison of published specifications and MSDS, yielding between 8.4 and 9.6 g. Simple conversion results in current density between 26 and 30 mA/g. Product of service hours (per datasheet) and discharge current yields total capacity, which can be converted to specific capacity by dividing it by weight of $MnO_2$. Voltage profile of the Coppertop AA cell as a function of specific $MnO_2$ capacity, calculated in such manner, is shown at FIG. 28. Curve A corresponds to maximum amount $MnO_2$ (9.6 g) where specific capacity of Duracell Coppertop AA cell is under constant current discharge at 26 mA/g rate. Curve B corresponds to minimum amount of $MnO_2$ (8.4 g) where specific capacity of Duracell Coppertop AA cell under constant current discharge is at 30 mA/g rate. Curve C shows a specific capacity of Duracell Coppertop AA cell under a constant current discharge rate of 2.2 mA/g. It is easy to see that $MnO_2$ specific capacity, calculated to 0.9 V cut-off, is between 235 and 270 mAh/g. Extrapolation to 0.8 V cut-off will result in slightly better specific capacity between 245 and 275 mAh/g. Discharge curves have typical sloping shape, characteristic to Zn/$MnO_2$ cells. Difference between voltage at 5% depth of discharge and 95% depth of discharge is close to 0.5 V or 30% of initial (5% DOD) [2.1-2.4 V/Ah/g]. Discharging Coppertop cell at extremely low rate of 2.2 mA/g (assuming average amount of $MnO_2$ in the cell) results in appearance of additional plateau (curve C). Total specific capacity was 347 mA/g, corresponding to 1.13-electron discharge. The discharge curve still has typical slopping shape with close to 0.5 V voltage difference between 5 and 95% depth of discharge.

COMPARATIVE EXAMPLE 10

AA cells were purchased in retail store and subjected to 250 mA discharge, corresponding to mid-rate test, using a Maccor 4300 system. Table 10.1 shows performance of commercial AA cells under 250 mA continuous discharge. Total capacity delivered to 0.9 V cut-off is shown in Table 10.1. Assuming amount of $MnO_2$ in the cells is the same as Comparative example 9, the total capacity of the cell can be converted to specific capacity of $MnO_2$. As one can see, under these discharge conditions commercial AA cells deliver between 200 and 280 mAh/g. Even taking into account positive effect of intermittent discharge and extending voltage cut-off to 0.8V, it is a fare statement that commercial alkaline cells operate within 1-electron reduction of $MnO_2$, described by equation (1), and are limited to 308 mAh/g.

TABLE 10.1

| Cell | Total Capacity Ah | Specific Capacity (mAh/g) | |
|---|---|---|---|
| | | Min | Max |
| Rayovac | 2.15 | 224 | 256 |
| Rayovac | 2.11 | 220 | 251 |
| Energizer Max | 1.84 | 191 | 219 |
| Energizer Max | 1.82 | 190 | 217 |
| Duracell Coppertop | 2.15 | 224 | 256 |
| Duracell Coppertop | 2.13 | 222 | 254 |

TABLE 10.1-continued

| | Total Capacity | Specific Capacity (mAh/g) | |
| --- | --- | --- | --- |
| Cell | Ah | Min | Max |
| Duracell Quantum | 2.35 | 244 | 279 |
| Duracell Quantum | 2.33 | 243 | 277 |

COMPARATIVE EXAMPLE 11 PER U.S. PAT. NO. 7,972,726

Figure 29:
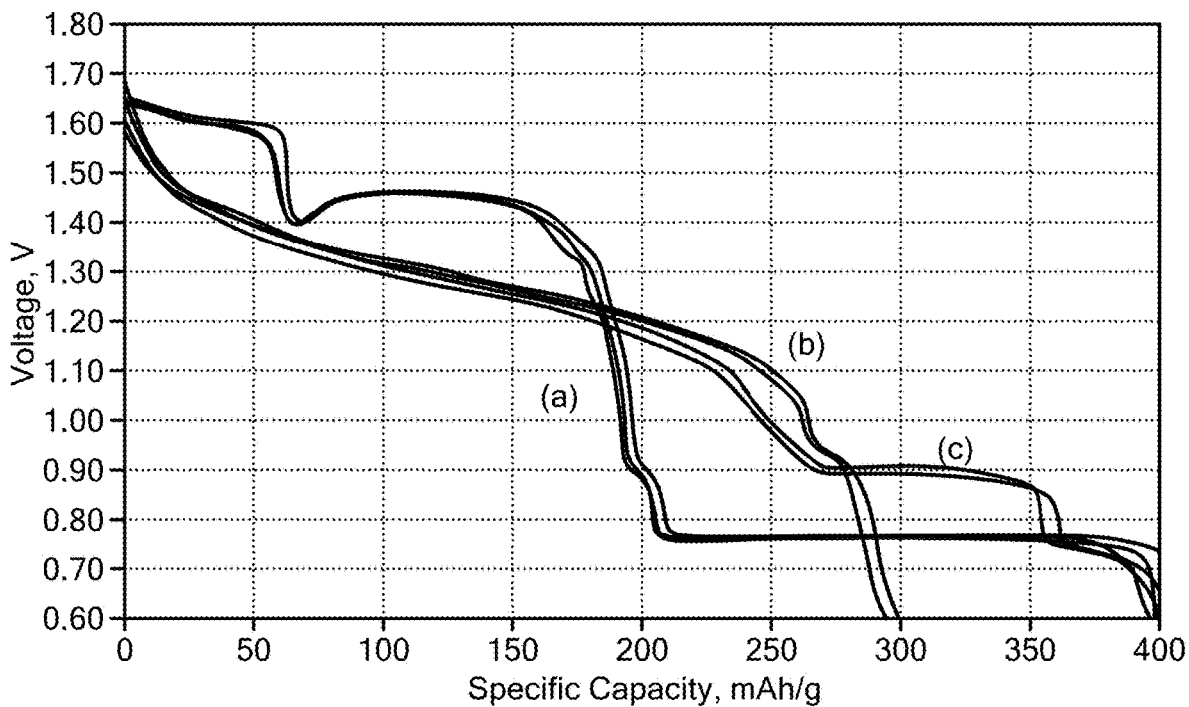
FIG. 29 illustrates discharge curves for alkaline button cells at 10 mA/g rate per prior art.

FIG. 29 shows discharge curves for alkaline button cells with cathodes based on AgBiO$_3$ cathode (curve (a)), EMD (MnO$_2$) cathode (curve (b)) and 1:9 AgBiO$_3$:EMD mixture at 10 mA/g discharge rate (curve (c)), reproduced from U.S. Pat. No. 7,972,726. Under these conditions, discharge profile for EMD (b) is similar to commercial alkaline cell described in comparative example 9 with 0.5 V difference between voltage at 5 and 95% DOD. MnO$_2$ capacity of about 290 mAh/g is consistent with 1-electron discharge. Cathodes made with AgBiO$_3$:EMD mixture displayed additional plateau at about 0.9 V, boosting MnO$_2$ capacity. Best performance was reported with 1:9 AgBiO$_3$:EMD mixture, which delivered 351 mAh/g before 0.8 V cut-off. This corresponds to 1.13-electron discharge of MnO$_2$.

EXAMPLE 12

PPS base polymer and ion source compound LiOH monohydrate were added together in the proportion of 67% to 33% (by wt.), respectively, and mixed using jet milling. Cathode was prepared by additionally mixing 50% β-MnO$_2$ from Alfa Aesar, 5% of Bi$_2$O$_3$ and 15% of C45 carbon black. DDQ dopant was added to the resulting mixture in the amount of 1 mole of DDQ per 4.2 moles of PPS.

The mixture was compression molded onto stainless steel mesh (Dexmet) at 325/250 C for 30 minutes under moderate pressure (500-1000 psi), yielding cathode disc 1" in diameter and 1.6-1.8 mm thick.

The resulting cathodes were used to assemble test cells, containing commercial non-woven separator (NKK) and Zn anode slurry extracted from commercial alkaline cells. 6M KOH solution in water was used as electrolyte.

Figure 30:
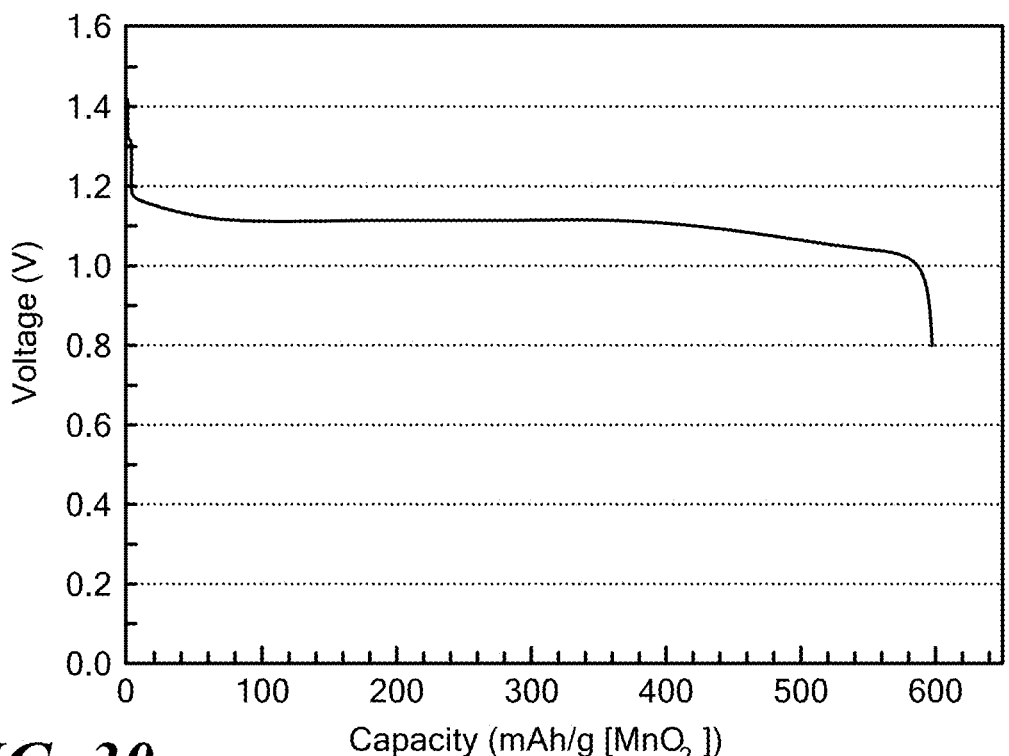
FIG. 30 exemplarily illustrates voltage profile of a cell of the invention per comparative example 12 at 35 mA/g constant current discharge as a function of specific capacity of $MnO_2$ FIG. 31 exemplarily illustrates voltage profile of a cell of the invention per example 13 as a function of specific capacity of $MnO_2$.

Cell was discharged under constant current conditions using Biologic VSP test system. FIG. 30 shows the voltage profile of cell per Example 12 at 35 mA/g constant current discharge as a function of specific capacity of MnO$_2$. The discharge profile, shown at FIG. 30, looks significantly more flat, compared to conventional Zn/MnO$_2$ cells. Voltage difference between 5 and 95% DOD is about 0.1 V or less than 10% of initial. The specific capacity of MnO$_2$ was close to 600 mAh/g or 97% of theoretical 2-electron discharge (616 mAh/g).

EXAMPLE 13

PPS base polymer and ion source compound LiOH monohydrate were added together in the proportion of 67% to 33% (by wt.), respectively, and mixed using jet milling. Cathode was prepared by additionally mixing 50% EMD from Tronox (mixture of γ- and ε-MnO$_2$), 5% of Bi2O3 and 15% of C45 carbon black. DDQ dopant was added to the resulting mixture in the amount of 1 mole of DDQ per 4.2 moles of PPS.

The mixture was compression molded onto stainless steel mesh (Dexmet) at 325/250 C for 30 minutes under moderate pressure (500-1000 psi), yielding cathode disc inch in diameter and 1.6-1.8 mm thick.

The resulting cathodes were used to assemble test cells, containing commercial non-woven separator (NKK) and Zn anode slurry extracted from commercial alkaline cells. 6M KOH solution in water was used as electrolyte.

Figure 31:
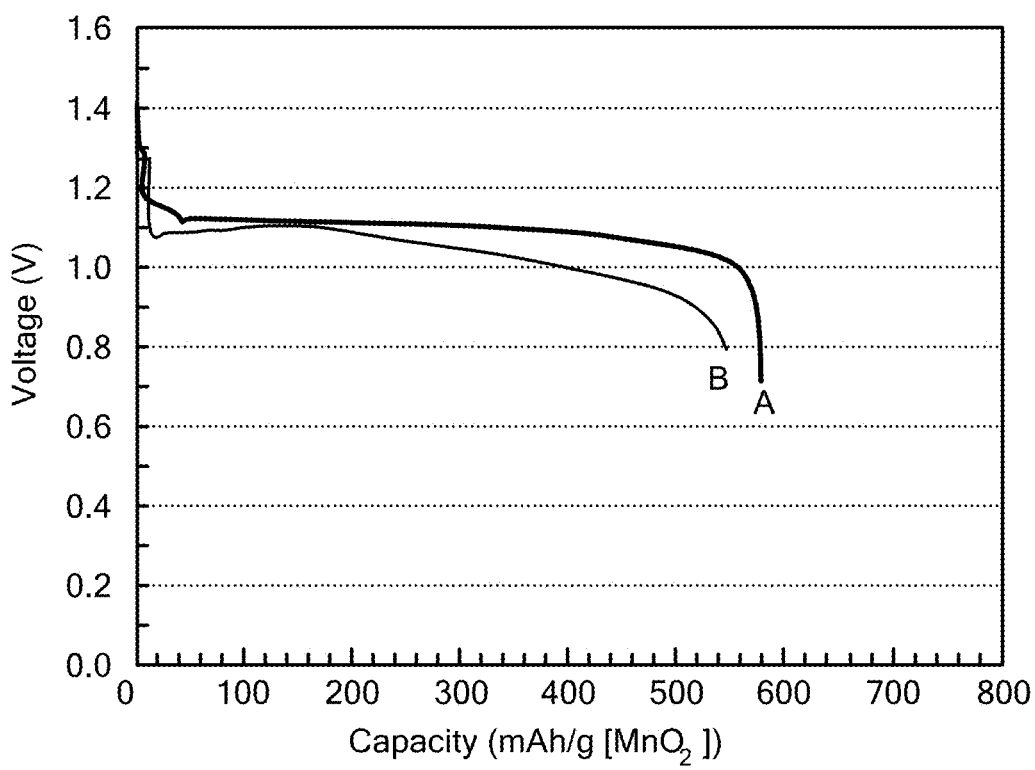

Cells were discharged under constant current conditions using Biologic VSP test system. FIG. 31 shows the voltage profile of the cell per Example 13 as a function of specific capacity of MnO$_2$ at 29 mA/g (Curve A) and 59 mA/g (Curve B). The specific capacity of MnO$_2$ was close to 600 mAh/g at 29 mA/g rate and close to 560 mAh/g at 59 mA/g rate.

EXAMPLE 14

PPS base polymer and ion source compound LiOH monohydrate were added together in the proportion of 67% to 33% (by wt.), respectively, and mixed using jet milling. Cathode was prepared by additionally mixing 80% EMD from Tronox (mixture of γ- and ε-MnO$_2$), 5% of C45 carbon black. DDQ dopant was added to the resulting mixture in the amount of 1 mole of DDQ per 4.2 moles of PPS.

The mixture was compression molded onto stainless steel mesh (Dexmet) at 325/250 C for 30 minutes under moderate pressure (500-1000 psi), yielding cathode disc 1" in diameter and 1.6-1.8 mm thick.

The resulting cathodes were used to assemble test cells, containing commercial non-woven separator (NKK) and Zn anode slurry extracted from commercial alkaline cells. 7M KOH solution in water was used as electrolyte.

Figure 32:
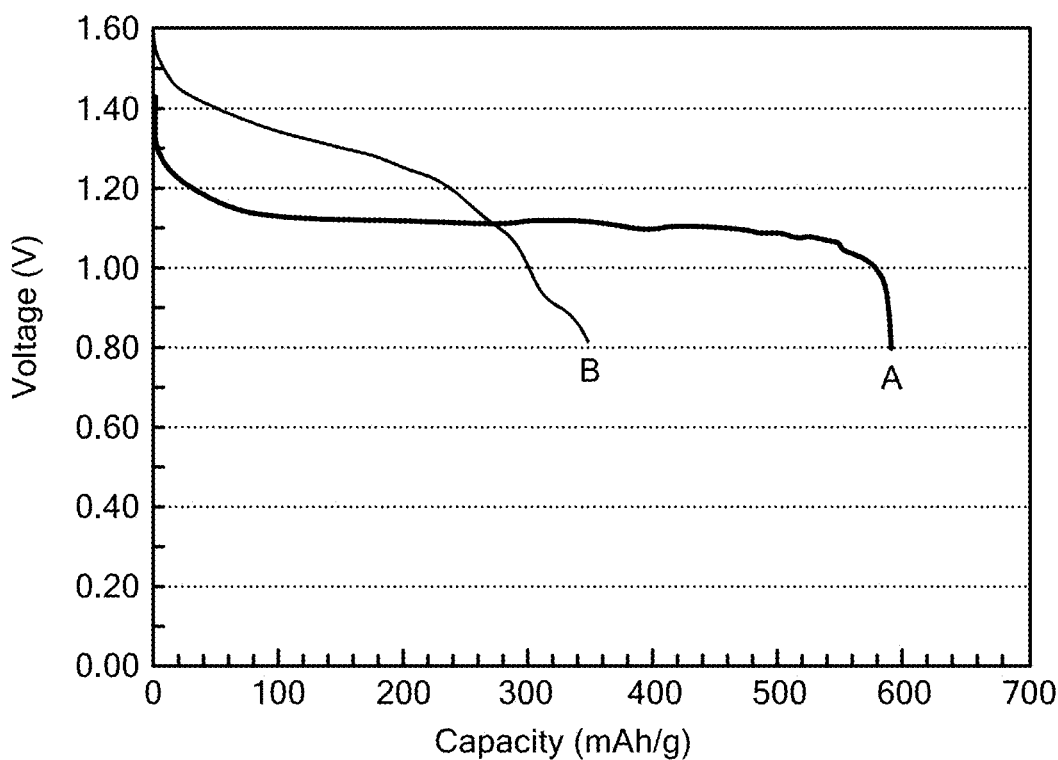
FIG. 32 exemplarily illustrates a voltage profile of cell of the invention per example 14 as a function of specific capacity of $MnO_2$ in comparison with a Duracell Coppertop cell.

The cell was discharged under constant current conditions at a rate of 9 mA/g using Biologic VSP test system. The specific capacity of MnO$_2$ was 590 mAh/g. FIG. 32 shows the voltage profile of cell per Example 14 as a function of specific capacity of MnO$_2$ at 9 mA/g discharge rate (curve A) and Duracell Coppertop cells at 2.2 mA/g (curve B). The voltage difference between 5 and 95% DOD was 0.163V or 13.6% (Curve A). Discharge profile for Duracell Coppertop cell at 2.2 mA/g is shown for comparison (Curve B).

EXAMPLE 15

PPS base polymer and ion source compound LiOH monohydrate were added together in the proportion of 67% to 33% (by wt.), respectively, and mixed using jet milling. Cathode was prepared by additionally mixing 80% EMD from Erachem (mixture of γ- and ε-MnO$_2$), 5% of C45 carbon black. DDQ dopant was added to the resulting mixture in the amount of 1 mole of DDQ per 4.2 moles of PPS.

The mixture was compression molded onto stainless steel mesh (Dexmet) at 325/250 C for 30 minutes under moderate pressure (500-1000 psi), yielding cathode disc 1" in diameter and 1.6-1.8 mm thick.

The resulting cathodes were used to assemble test cells, containing commercial non-woven separator (NKK) and Zn anode slurry extracted from commercial alkaline cells. 7M KOH solution in water was used as electrolyte.

Figure 33:
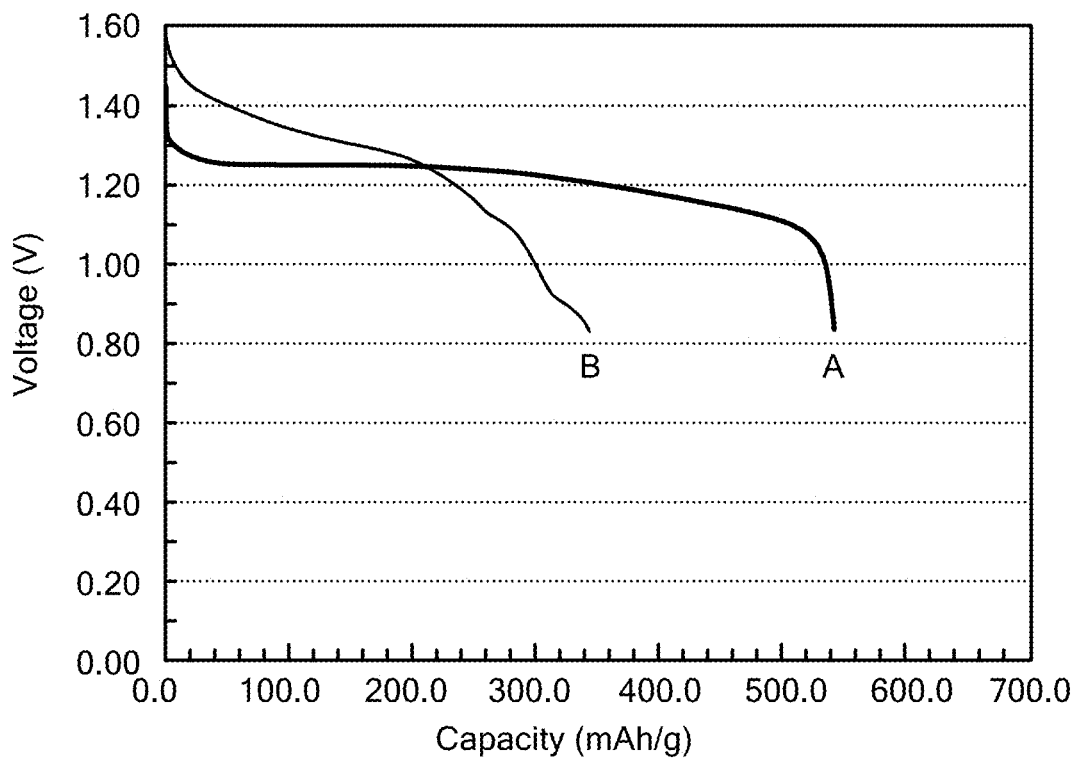
FIG. 33 exemplarily illustrates a voltage profile of a cell of the invention per example 15 as a function of specific capacity of $MnO_2$ in comparison with a Duracell Coppertop cell.

The cell was discharged under constant current conditions at a rate of 9.5 mA/g using Biologic VSP test system. The specific capacity of MnO$_2$ was 541 mAh/g. FIG. 33 shows the voltage difference between 5 and 95% DOD was 0.180V or 14.1% (Curve A). Discharge profile for Duracell Coppertop cell at 2.2 mA/g is shown for comparison (Curve B).

EXAMPLE 16

PPS base polymer and ion source compound LiOH monohydrate were added together in the proportion of 67% to 33% (wt/wt), respectively, and were mixed using jet milling. The mixture was compression molded at 325° C./250° C. for 30 minutes under low pressure. The polymer-sulfur composite cathode was prepared by additionally mixing from 25% to 50% of sulfur powder, 5% to 15% of C45 carbon black, and 0% to 10% $LiNO_3$ with the solid, ionically conducting polymer material. The materials were compression molded onto stainless steel mesh (Dexmet) at 120° C. for 30 minutes, yielding a cathode disc 15 mm in diameter and 0.3 to 0.4 mm thick.

The resulting cathodes were used to assemble test cells in 2035 coin cell hardware. Polypropylene separator (Celgard) 25 microns thick and 19 mm in diameter was used along with lithium foil anode material, 15 mm in diameter. A liquid electrolyte of 1M LiTFSI salt dissolved in a 50/50 (vol/vol) mixture of DOL/DME was used, with 0.5M $LiNO_3$ additive. The cells were assembled in an argon gas filled glovebox, with low oxygen and water levels.

Cells were discharged under constant current conditions (1 mA) using a Maccor 4600 battery test system. Discharge was terminated at a voltage of 1.75 V.

Figure 34:
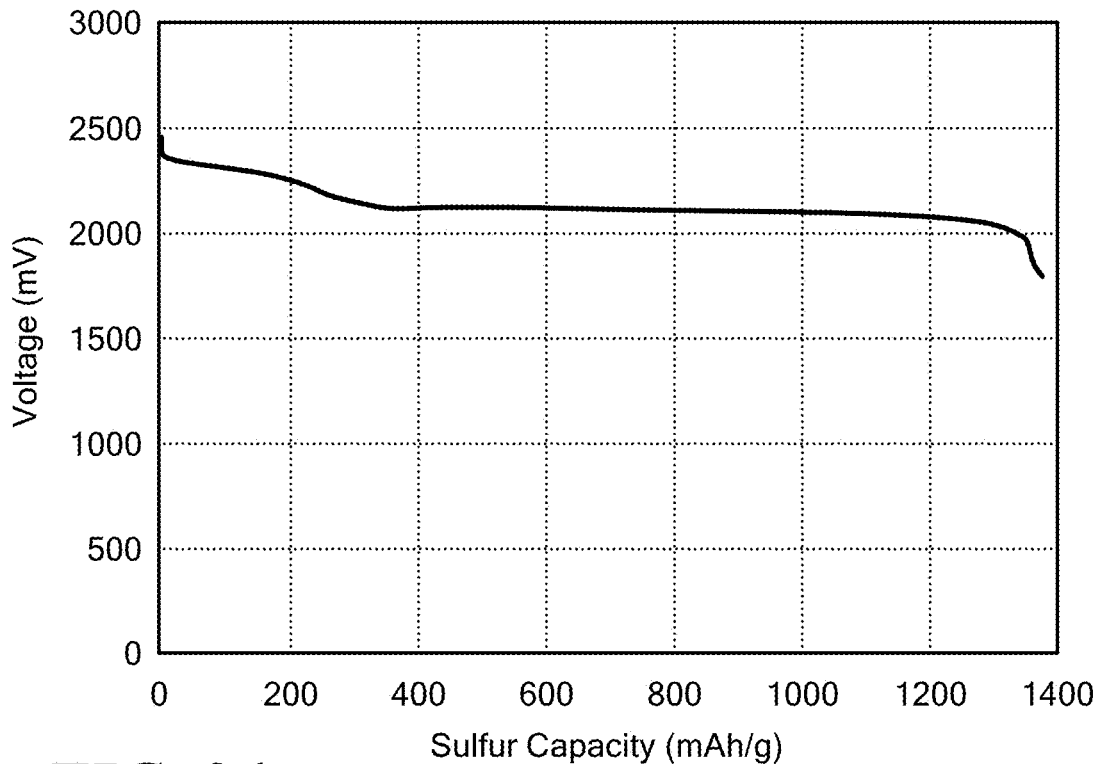
FIG. 34 exemplarily illustrates a first discharge voltage curve for Li/Ionic polymer-sulfur cell of the present invention.

FIG. 34 shows a first discharge voltage curve for a Li/composite polymer-sulfur cathode in a cell of the present invention. The discharge voltage profile for the first cycle is displayed in FIG. 34. It can be seen that the composite polymer-sulfur cathode provides a high initial capacity of >1300 mAh/g, based on the amount of sulfur in the cathode. The cell in FIG. 34 also displays a discharge voltage curve with two plateaus, at ~2.3V and ~2.1V. This shows that the composite polymer-sulfur system enables high capacity, while producing the expected voltage curve for a lithium/sulfur system, consistent with a stable electrochemical couple.

EXAMPLE 17

Composite polymer-sulfur cathodes were manufactured as described in Example 16. These cathodes were assembled into coin cells using lithium metal anodes, polypropylene separator, and 1M LiTFSI in DOL/DME electrolyte with 0.5M $LiNO_3$ additive.

Cells were discharged under constant current conditions (1 mA) using a Maccor 4600 battery test system. Discharge was terminated at a voltage of 1.75 V. Charge was accomplished in two steps, the first at a lower charge rate of 0.2 mA current to a maximum voltage of 2.3 V, and the second charge step at a higher rate of 1 mA current to a maximum voltage of 2.45 V. The overall charge capacity was limited for these test cells. These cells were allowed to cycle several times at room temperature.

Figure 35:
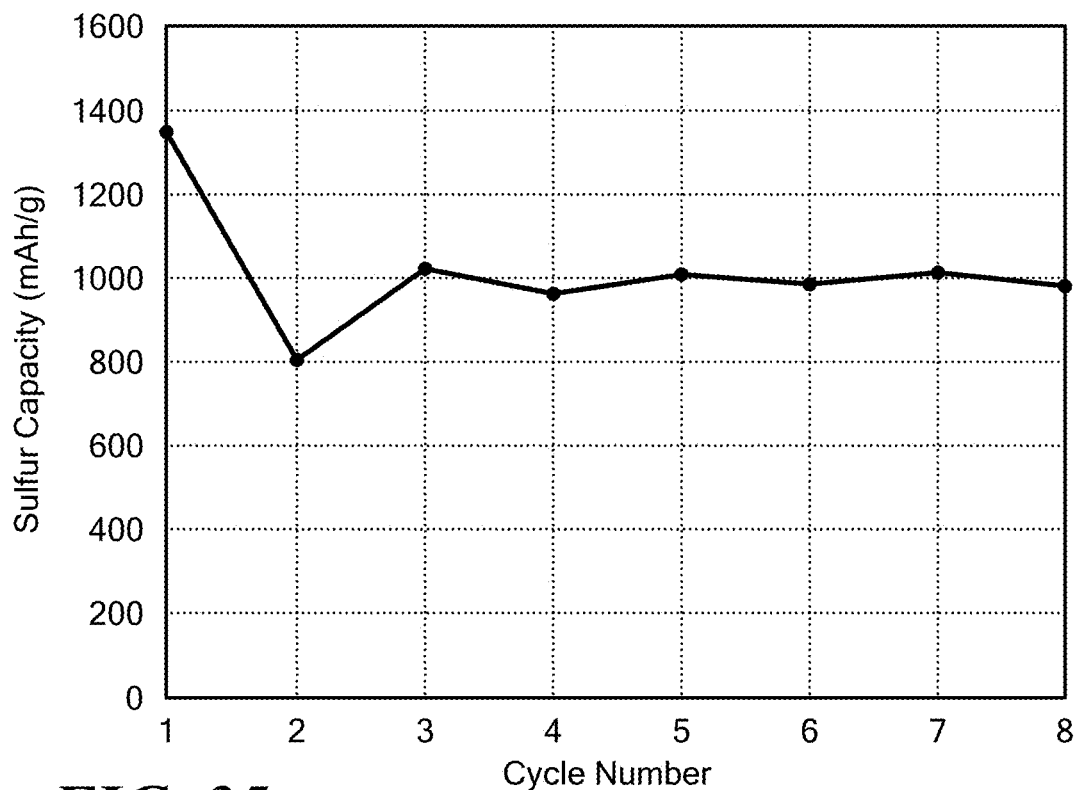
FIG. 35 exemplarily illustrates a discharge capacity curve plotted as a function of cycle number for Li/Ionic polymer-sulfur cell of the present invention.

FIG. 35 shows the discharge capacity curve plotted as a function of cycle number for Li/composite polymer-sulfur cell of the present invention. This graph shows that the composite polymer-sulfur cathode will support reversible charge/discharge, with high reversible capacity of at least 1000 mAh/g based on the amount of sulfur in the cathode.

COMPARATIVE EXAMPLE 18

Figure 36:
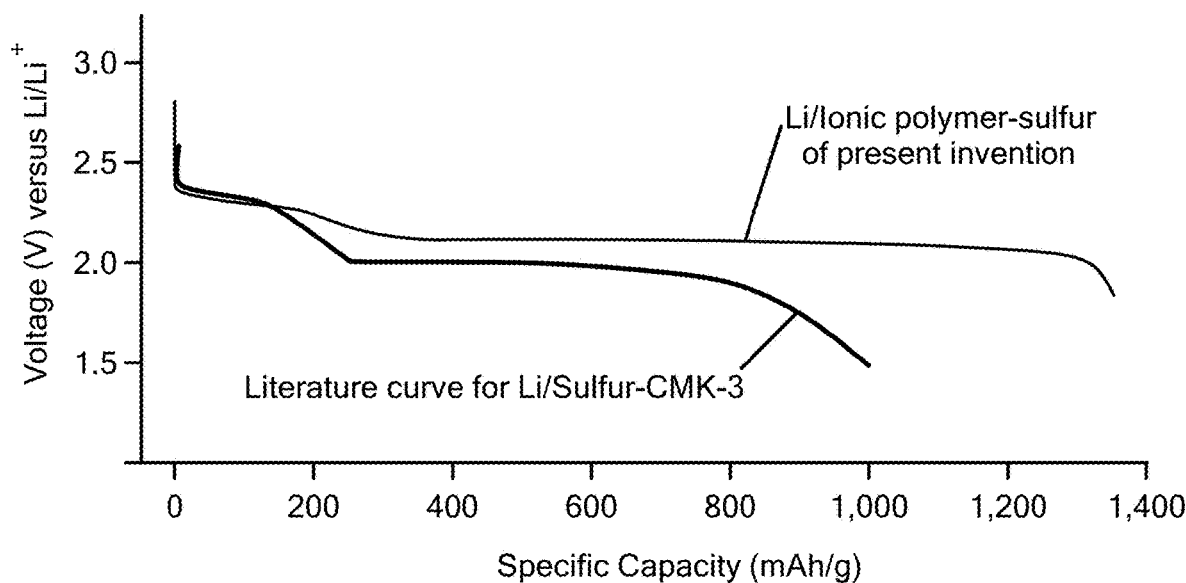
FIG. 36 exemplarily illustrates a comparison of first discharge for literature example Li/Sulfur-CMK-3 with Li/Ionic polymer-sulfur of present invention.

A noteworthy example of a highly ordered interwoven composite electrode is presented in the literature [Ji, X.; Lee, K. T.; Nazar, L. F. *Nature Materials* 2009, 8, 500-506]. This composite cathode utilized CMK-3 mesoporous carbon with sulfur entrenched in the pores through heat treatment at 155° C. FIG. 36 compares the first discharge for literature example Li/Sulfur-CMK-3 with Li/composite polymer-sulfur of present invention.

The composite cathode in this example was slurry-cast from cyclopentanone onto a carbon coated aluminum current collector. The cathode utilized 84 wt % CMK-3/S composite, 8 wt % Super-S carbon and 8 wt % PVDF binder. The electrolyte was composed of 1.2 M $LiPF_6$ in ethyl methyl sulphone, and Li metal was used as the anode. In comparison, the results for the composite polymer-sulfur cathode of the invention, as described in Example 16, are plotted on the same graph. It is apparent that the composite polymer-sulfur cathode of the invention gives as good, or better, results than literature examples of composite sulfur cathodes.

COMPARATIVE EXAMPLE 19

Figure 37:
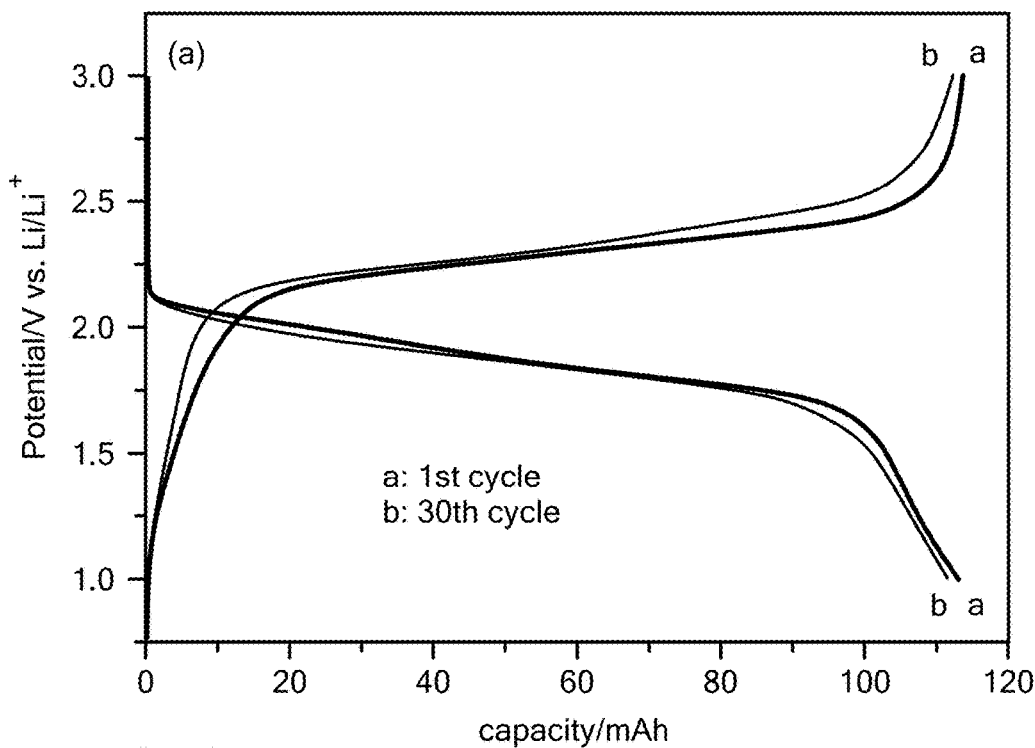
FIG. 37 illustrates a charge/discharge voltage curves for a Li/sulfur-poly(pyridinopyridine) cell from the prior art.

The use of sulfur-conductive polymer composites as cathodes for lithium batteries has been demonstrated. In one case, polyacrylonitrile (PAN) is sulfurized to form a conductive and chemically active cathode material. The sulfurization of the polymer takes place at a relatively high temperature of ~300° C. An example of the discharge curve for this material is shown in FIG. 37, which was displayed in U.S. Patent Application 2014/0045059 [He, X.-M., et. al.]. FIG. 37 shows the typical voltage signature seen for Li/Sulfur-Polyacrylonitrile (S/PAN) cells. These cells are typified by a single sloping voltage plateau, with an average voltage below 2.0 V. In comparison to the voltage curve observed in FIG. 4 for the Li/composite polymer-sulfur cathode in a cell of the invention, it can be seen that the S/PAN cells display significantly lower voltage throughout discharge, which results in a lower energy density, based on Watt-hours. Thus, the voltage behavior displayed by the composite polymer polymer-sulfur cathode of the invention is superior to that of the sulfurized PAN-based cathodes.

EXAMPLE 20

Solid polymer electrolyte samples were made by mixing SRT802 (Liquid Crystal Polymer) polymer with lithium hydroxide monohydrate, as a compound comprising ion source, in a proportion 2:1, respectively (by weight). DDQ was used a dopant. Weight ratio of polymer to dopant was 2:1. Mixtures were heat treated at 325/250° C. for 30 minutes under moderate pressure (500-1000 PSI). The ionic surface conductivity of the samples were measured using standard AC-EIS. Samples were sandwiched between stainless steel blocking electrodes and placed in test fixture. AC-impedance was recorded in the range from 800 KHz to 100 Hz using Biologic VSP test system to determine the electrolyte conductivity. Six samples were prepared and tested. Average conductivity was $3.7 \times 10^{-4}$ S/cm with about 19% standard deviation. The results are shown in the following Table 20.1.

TABLE 20.1

| Sample | Conductivity (S/cm) |
| --- | --- |
| 1 | 3.42E−04 |
| 2 | 4.78E−04 |
| 3 | 4.09E−04 |

TABLE 20.1-continued

| Sample | Conductivity (S/cm) |
|---|---|
| 4 | 2.69E−04 |
| 5 | 3.46E−04 |
| 6 | 4.04E−04 |
| Average | 3.75E−04 |
| Standard Deviation | 7.18E−05 |
| Standard Deviation % | 19.2% |

EXAMPLE 21

Solid polymer electrolyte samples were made by mixing SRT900 (Liquid Crystal Polymer) polymer with lithium hydroxide monohydrate, as a compound comprising ion source, in a proportion 2:1, respectively (by weight). DDQ was used a dopant. Weight ratio of polymer to dopant was 2:1. Mixtures were heat treated at 325/250 C for 30 minutes under moderate pressure (500-1000 psi). Samples were sandwiched between stainless steel electrodes and placed in test fixture. AC-impedance was recorded in the range from 800 KHz to 100 Hz using Biologic VSP test system to determine the electrolyte conductivity. Six samples were prepared and tested. Average conductivity was $1.5 \times 10^{-3}$ S/cm with about 25% standard deviation. The results are shown in the following Table 21.1

TABLE 21.1

| Sample | Conductivity (S/cm) |
|---|---|
| 1 | 1.14E−03 |
| 2 | 1.39E−03 |
| 3 | 1.59E−03 |
| 4 | 1.31E−03 |
| 5 | 1.20E−03 |
| 6 | 2.13E−03 |
| Average | 1.46E−03 |
| Standard Deviation | 3.63E−04 |
| Standard Deviation % | 24.9% |

EXAMPLE 22

Polymer electrolyte samples were made by mixing polymer and compound comprising ion source in various proportions. DDQ was used a dopant. Molar ratio of polymer to dopant was 4.2. Mixtures were heat treated at 325/250 C for 30 minutes under moderate pressure (500-1000 psi). Samples were sandwiched between stainless steel electrodes and placed in test fixture. AC-impedance was recorded in the range from 800 KHz to 100 Hz using Biologic VSP test system to determine the electrolyte conductivity.

Results are shown in the table below. High observed conductivity suggests that the polymer electrolyte can conduct multiple ions, including to $Li^+$, $K^+$, $Na^+$, $Ca^{2+}$, $Mg^{2+}$, $Al^{3+}$, $OH^-$ and $Cl^-$.

| Ion Source | Ion Source Wt. % | Conductivity (S/cm) |
|---|---|---|
| $Li_2O$ | 33% | 1.9E−04 |
| $Na_2O$ | 33% | 4.2E−05 |
| MgO | 33% | 6.3E−07 |
| $CaCl_2$ | 33% | 6.2E−03 |
| $MgCl_2$ | 20% | 8.0E−03 |
| $AlCl_3$ | 15% | 2.4E−03 |
| NaOH | 50% | 1.3E−04 |
| KOH | 50% | 2.2E−04 |

Ability to conduct ions other than $Li^+$ opens new applications for the polymer electrolyte. Sodium- and potassium-based energy storage systems are viewed as alternative to Li-ion, driven primarily by low cost and relative abundance of the raw materials.

Calcium, magnesium and aluminum conductivity is important developing multivalent intercalation systems, potentially capable of increasing energy density beyond capabilities of Li-ion batteries. There is also a possibility to utilize such materials to create power sources with metal anodes, more stable and less costly than lithium.

Hydroxyl conductivity is crucial for numerous alkaline chemistries, including $Zn/MnO_2$, Ni/Zn, Ni—Cd, Ni—MH, Zn-air, Al-air. Polymer electrolytes conducting hydroxyl ions can be also used in alkaline fuel cells and super capacitors.

EXAMPLE 23

Solid Ionically Conductive Polymer Material:
Polyphenylene sulphide "PPS" (base polymer) and tetrachloro-1,4-benzoquinone "chloranil" are mixed and heated to form a solid intermediate polymer material, that when mixed with a compound including a source of ions forms the solid ionically conductive polymer material. The compound comprises 10-50% by weight of the base polymer. The heating step raises the temperature of the reactants to 250-350° C., and takes from about 10 minutes to 8 hours to overnight. In an aspect, the solid ionically conductive polymer material or its intermediate or its reactants can be mixed with additives (e.g. electrically conductive carbons) to form a composite that is both ionically conductive and provides the functional attribute of the additive (e.g. electrical conductivity).

Zn Anode:
Zinc powder (pure powder or zinc powder alloyed with bismuth, indium, calcium, aluminum and other alloying agents known in the art) is mixed with solid intermediate polymer material, lithium hydroxide, conductive carbon additive (e.g C45 or KS6L graphite by Tincal, EC600—a high surface area carbon from AkzoNobel, etc), additives zinc oxide and/or other corrosion-resistive additives. PVDF or Kynar PVDF is used as binder, with NMP as a solvent. A mixer (e.g. Thinky) can be used and if used to mix the mixture is mixed until a homogeneous slurry is obtained (e.g. 10-30 min at 2000 rpm). The slurry is then casted by a doctor blade technique onto a current collector (stainless steel, titanium or nickel foil), which has a thin layer of graphite primer pre-coated. Electrodes were then dried at 80-120° C. for 2-12 hours, calendared and sliced into desired dimensions for coin cells or pouch cells.

$MnO_2$ Cathode:
EMD MnO2 powder mixed with conductive additive (e.g. C45, KS6L graphite, EC600 high surface area carbon, etc), solid intermediate polymer material, and the ionic compound lithium hydroxide. PVDF (Polyvinylidene fluoride) or Kynar PVDF is used as binder, with NMP (N-Methyl-2-pyrrolidone) as solvent. A Thinky brand mixer is used to mix the mixture for 10-30 min at 2000 rpm until a homogeneous slurry is obtained. The slurry is then casted by a doctor blade technique onto a current collector (stainless steel, titanium or nickel foil), which has a thin layer of graphite primer pre-coated. Electrodes were then dried at 80-120° C. for 2-12 hours, calendared and sliced into desired dimensions for coin cells or pouch cells. Overall, the solid ionically conductive polymer material comprises about 2-30 weight % of the total cathode weight, and the active (EMD in this case) is about 20-80 wt %, carbon is about 3-30 wt %, and liquid electrolyte Electrolyte:

Various electrolytes can be used. In an aspect the electrolyte formulation is an aqueous solution containing 36 wt. % potassium hydroxide with zinc oxide as an additive. In an aspect, a 1-3 molar concentration of zinc sulfate salt, with the addition of additives 0.5-4 wt. % of manganese sulfate (or other Mn(ii) salts) is used. These aqueous electrolytes can be added to 0.5-2 wt. % of a gelling agent, e.g. poly(ethylene glycol) di-acid (or other gelling agents known in the art). In an aspect, the solid ionically conductive polymer material is used as the electrolyte, a separator is not required, and a small amount of KOH solution or other liquid electrolyte solution can be optionally added to the anode or cathode.

Figure 41:
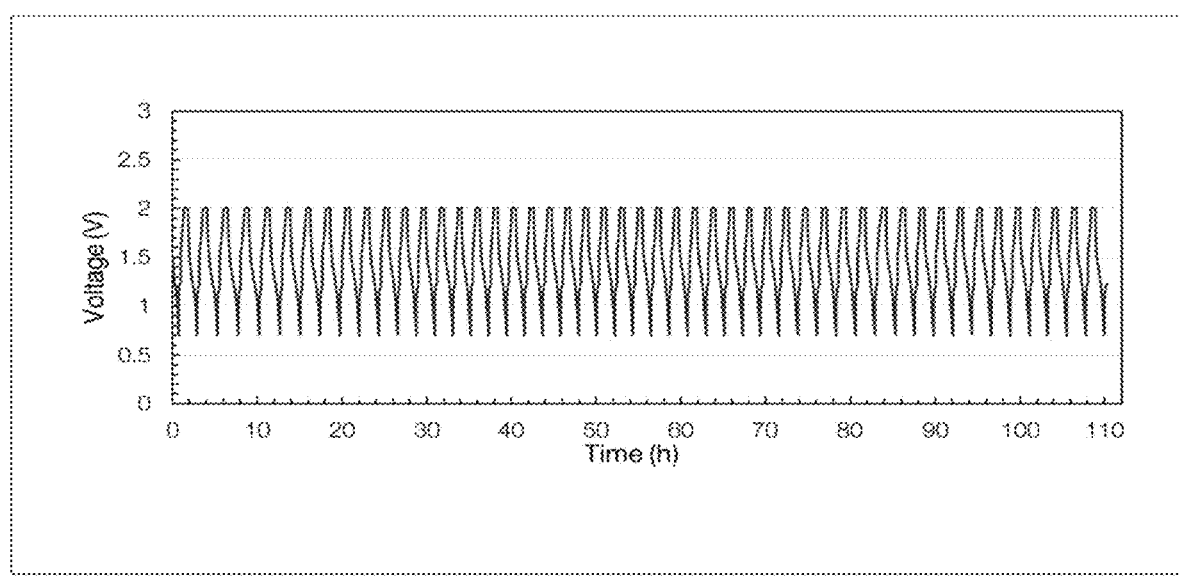
FIG. 41 shows a plot of voltage over time for one cell embodiment.

Cell Construction:

CR2032 coin cells, bobbin cylindrical cell, and single-layer and multi-layer pouch cells have all been made using the same cathode and anode combination. Cell assembly steps are the same as commonly used in the industry, including electrode slurry, closing, crimping, Use a coin cell as an example, a cathode and an anode are sandwiched between a layer of non-woven separator that soaked with the above described zinc sulfate liquid electrolyte as described above. FIG. 41 shows the typical charge-discharge profiles of a rechargeable Zn—$MnO_2$ battery in a CR2032 coin cell format.

Although this construction is described as a secondary cell, it has been found useful as a primary battery also.

Referring to Table 23.1, there is shown multiple constructions using the solid ionically conducting polymer material. Listed are a primary construction, three (1-3) secondary alkaline constructions including a solid-state formulation, and a zinc air construction.

Secondary formulation (1) corresponds to FIG. 41 and associated discussion.

Secondary formulation (2) corresponds to FIGS. 38-40 and associated discussion. Liquid potassium hydroxide electrolyte was added. Procedure for cathode and anode making did not involve the use of a mechanical mixer or slurry casting. Anodes and cathodes contained no binder (no PVDF) and did not need NMP solvent.

While the present invention has been described in conjunction with preferred embodiments, one of ordinary skill, after reading the foregoing specification, will be able to effect various changes, substitutions of equivalents, and other alterations to that set forth herein. It is therefore intended that the protection granted by Letters Patent hereon be limited only by the definitions contained in the appended claims and equivalents thereof.

What is claimed is:

1. An electrochemical cell for producing electrical energy via an electrochemical reaction comprising:
   an anode; and
   a cathode;
   wherein at least one of the anode and the cathode comprise a solid ionically conducting polymer material;
   wherein the solid ionically conducting polymer material can ionically conduct hydroxyl ions, whereby the solid ionically conducting polymer material can conduct hydroxyl ions during said electrochemical reaction; and
   wherein the solid ionically conducting polymer material has a crystallinity index of at least or greater that about 30%.

2. An electrochemical cell for producing electrical energy via an electrochemical reaction comprising:
   an anode; and
   a cathode;
   wherein at least one of the anode and the cathode comprise a solid ionically conducting polymer material;
   wherein the solid ionically conducting polymer material can ionically conduct hydroxyl ions, whereby the solid ionically conducting polymer material can conduct hydroxyl ions during said electrochemical reaction;
   wherein the anode comprises the solid ionically conducting polymer material and further comprises an anode electrochemically active material; and
   wherein the solid ionically conducting polymer material and the anode electrochemically active material are mixed, whereby the solid ionically conducting polymer material can ionically conduct hydroxyl ions to the anode electrochemically active material.

3. The cell of claim 2, wherein at least a portion of the solid ionically conducting polymer material is in contact with the anode electrochemically active material.

4. An electrochemical cell for producing electrical energy via an electrochemical reaction comprising:
   an anode; and
   a cathode;
   wherein at least one of the anode and the cathode comprise a solid ionically conducting polymer or material;
   wherein the solid ionically conducting polymer material can ionically conduct hydroxyl ions, whereby the solid ionically conducting polymer material can conduct hydroxyl ions during said electrochemical reaction;
   wherein the cathode comprises the solid ionically conducting polymer material and further comprises a cathode electrochemically active material; and
   wherein the solid ionically conducting polymer material and the cathode electrochemically active material are mixed, whereby the solid ionically conducting polymer material can ionically conduct hydroxyl ions to the cathode electrochemically active material.

5. The cell of claim 4, wherein at least a portion of the solid ionically conducting polymer material is in contact with the cathode electrochemically active material.

6. An electrochemical cell for producing electrical energy via an electrochemical reaction comprising:
   an anode; and
   a cathode;
   wherein at least one of the anode and the cathode comprise a solid ionically conducting polymer material;
   wherein the solid ionically conducting polymer material can ionically conduct hydroxyl ions, whereby the solid ionically conducting polymer material can conduct hydroxyl ions during said electrochemical reaction;
   wherein the cathode comprises the solid ionically conducting polymer material; and
   wherein the amount of the solid ionically conducting polymer material ranges between 1 and 40 weight percent of the cathode.

* * * * *